US012737991B2

(12) United States Patent
Shelton, IV et al.

(10) Patent No.: US 12,737,991 B2
(45) Date of Patent: Sep. 15, 2026

(54) UTILIZATION OF SURGICAL DATA VALUES AND SITUATIONAL AWARENESS TO CONTROL THE OVERLAY IN SURGICAL FIELD VIEW

(71) Applicant: Cilag GmbH International, Zug (CH)

(72) Inventors: Frederick E. Shelton, IV, Hillsboro, OH (US); Shane R. Adams, Lebanon, OH (US); Matthew D. Cowperthwait, Cincinnati, OH (US); Kevin M. Fiebig, Cincinnati, OH (US); Jason L. Harris, Lebanon, OH (US); Cory G. Kimball, Hamilton, OH (US); Monica L. Z. Rivard, Cincinnati, OH (US); Leonardo N. Rossoni, Rahway, NJ (US); Risto Kojcev, Santa Clara, CA (US); Felix J. Bork, Schnürpflingen (DE)

(73) Assignee: Cilag GmbH International, Zug (CH)

( * ) Notice: Subject to any disclaimer, the term of this patent is extended or adjusted under 35 U.S.C. 154(b) by 657 days.

(21) Appl. No.: 17/688,597

(22) Filed: Mar. 7, 2022

(65) Prior Publication Data

US 2022/0331048 A1 Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.

| | |
|---|---|
| ***G06T 11/00*** | (2006.01) |
| ***A61B 34/00*** | (2016.01) |

(Continued)

(52) U.S. Cl.

CPC .............. *G06T 11/00* (2013.01); *A61B 34/20* (2016.02); *A61B 34/25* (2016.02); *A61B 34/30* (2016.02);

(Continued)

(58) Field of Classification Search

CPC ......... A61B 34/20; A61B 34/25; A61B 34/30; A61B 34/76; A61B 90/36; A61B 2090/365

See application file for complete search history.

(56) References Cited

U.S. PATENT DOCUMENTS

| | | | |
|---|---|---|---|
| 916,085 | A | 3/1909 | Wood |
| 4,171,700 | A | 10/1979 | Farin |

(Continued)

FOREIGN PATENT DOCUMENTS

| | | | |
|---|---|---|---|
| CA | 3 003 058 | A1 | 5/2017 |
| CN | 112603496 | A | 4/2021 |

(Continued)

OTHER PUBLICATIONS

"ATM-MPLS Network Interworking Version 2.0, af-aic-0178.001" ATM Standard, The ATM Forum Technical Committee, published Aug. 2003.

(Continued)

*Primary Examiner* — Jeffery A Brier

(74) *Attorney, Agent, or Firm* — Condo Roccia Koptiw LLP

(57) ABSTRACT

A surgical visualization system is disclosed including an imaging device, a display configured to show a livestream of a surgical field of a surgical procedure, and a control module configured to detect surgical data, assign display priority values to the surgical data, determine a display arrangement of the surgical data based on the display priority values, and present the surgical data on the display in accordance with (Continued)

the display arrangement. The livestream is captured by the imaging device.

20 Claims, 28 Drawing Sheets

(51) Int. Cl.

| | |
|---|---|
| ***A61B 34/10*** | (2016.01) |
| ***A61B 34/20*** | (2016.01) |
| ***A61B 34/30*** | (2016.01) |
| ***A61B 34/32*** | (2016.01) |
| ***A61B 90/00*** | (2016.01) |
| ***G06F 3/14*** | (2006.01) |
| ***G06F 3/147*** | (2006.01) |
| ***G06T 7/00*** | (2017.01) |
| ***G06T 7/20*** | (2017.01) |
| ***G06T 19/00*** | (2011.01) |
| ***G06V 20/20*** | (2022.01) |
| ***G08B 21/18*** | (2006.01) |
| ***G16H 20/40*** | (2018.01) |
| ***G16H 40/67*** | (2018.01) |
| ***H04L 9/40*** | (2022.01) |
| ***H04L 67/12*** | (2022.01) |
| ***H04W 24/10*** | (2009.01) |
| ***H04W 76/14*** | (2018.01) |

(52) U.S. Cl.

CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2034/252* (2016.02); *A61B 2034/254* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(56) References Cited

U.S. PATENT DOCUMENTS 4,849,752 A 7/1989 Bryant
D303,787 S 10/1989 Messenger et al.
D327,061 S 6/1992 Soren et al.
5,189,277 A 2/1993 Boisvert et al.
5,204,669 A 4/1993 Dorfe et al.
5,318,563 A 6/1994 Malis et al.
5,325,270 A 6/1994 Wenger et al.
5,425,375 A 6/1995 Chin et al.
D379,346 S 5/1997 Mieki
5,690,504 A 11/1997 Scanlan et al.
5,693,042 A 12/1997 Boiarski et al.
5,724,468 A 3/1998 Leone et al.
6,049,467 A 4/2000 Tamarkin et al.
6,055,458 A 4/2000 Cochran et al.
D431,811 S 10/2000 Nishio et al.
6,179,136 B1 1/2001 Kluge et al.
6,269,411 B1 7/2001 Reasoner
6,288,606 B1 9/2001 Ekman et al.
6,416,471 B1 7/2002 Kumar et al.
6,501,485 B1 * 12/2002 Dash .................. H04N 1/00466 715/965
6,546,270 B1 4/2003 Goldin et al.
6,584,358 B2 6/2003 Carter et al.
6,611,793 B1 8/2003 Burnside et al.
6,731,514 B2 5/2004 Evans
6,760,218 B2 7/2004 Fan
6,839,238 B2 1/2005 Derr et al.
6,843,657 B2 1/2005 Driscoll et al.
6,913,471 B2 7/2005 Smith
7,009,511 B2 3/2006 Mazar et al.
7,044,949 B2 5/2006 Orszulak et al.
7,074,205 B1 7/2006 Duffy et al.
7,134,994 B2 11/2006 Alpert et al.
7,171,784 B2 2/2007 Eenigenburg
7,217,269 B2 5/2007 El-Galley et al.
7,252,664 B2 8/2007 Nasab et al.
7,331,699 B2 2/2008 Gawalkiewicz et al.
7,344,532 B2 3/2008 Goble et al.
7,353,068 B2 4/2008 Tanaka et al.
7,408,439 B2 8/2008 Wang et al.
D579,876 S 11/2008 Novotney et al.
D583,328 S 12/2008 Chiang
7,496,418 B2 2/2009 Kim et al.
D589,447 S 3/2009 Sasada et al.
7,500,747 B2 3/2009 Howell et al.
7,518,502 B2 4/2009 Austin et al.
7,563,259 B2 7/2009 Takahashi
7,601,149 B2 10/2009 DiCarlo et al.
7,637,907 B2 12/2009 Blaha
7,656,671 B2 2/2010 Liu et al.
7,757,028 B2 7/2010 Druke et al.
D631,252 S 1/2011 Leslie
7,932,826 B2 4/2011 Fritchie et al.
7,945,065 B2 5/2011 Menzl et al.
7,945,342 B2 5/2011 Tsai et al.
7,982,776 B2 7/2011 Dunki-Jacobs et al.
7,995,045 B2 8/2011 Dunki-Jacobs
8,019,094 B2 9/2011 Hsieh et al.
8,086,008 B2 12/2011 Coste-maniere et al.
D655,678 S 3/2012 Kobayashi et al.
D657,368 S 4/2012 Magee et al.
8,239,066 B2 8/2012 Jennings et al.
D667,838 S 9/2012 Magee et al.
D675,164 S 1/2013 Kobayashi et al.
D676,392 S 2/2013 Gassauer
D678,196 S 3/2013 Miyauchi et al.
D678,304 S 3/2013 Yakoub et al.
8,423,182 B2 4/2013 Robinson et al.
D687,146 S 7/2013 Juzkiw et al.
8,504,136 B1 8/2013 Sun et al.
8,540,709 B2 9/2013 Allen
8,567,393 B2 10/2013 Hickle et al.
D704,839 S 5/2014 Juzkiw et al.
8,795,001 B1 8/2014 Lam et al.
8,819,581 B2 8/2014 Nakamura et al.
D716,333 S 10/2014 Chotin et al.
8,917,513 B1 12/2014 Hazzard
8,920,186 B2 12/2014 Shishikura
8,923,012 B2 12/2014 Kaufman et al.
8,968,296 B2 3/2015 McPherson
8,986,288 B2 3/2015 Konishi
9,017,326 B2 4/2015 Dinardo et al.
D729,267 S 5/2015 Yoo et al.
9,055,870 B2 6/2015 Meador et al.
9,065,394 B2 6/2015 Lim et al.
9,129,054 B2 9/2015 Nawana et al.
9,160,853 B1 10/2015 Daddi et al.
9,168,054 B2 10/2015 Turner et al.
9,168,085 B2 10/2015 Juzkiw et al.
9,168,091 B2 10/2015 Janssen et al.
9,198,711 B2 12/2015 Joseph
9,220,570 B2 12/2015 Kim et al.
9,226,766 B2 1/2016 Aldridge et al.

(56) References Cited

U.S. PATENT DOCUMENTS 9,226,791 B2 1/2016 Mccarthy et al.
9,237,921 B2 1/2016 Messerly et al.
9,265,429 B2 2/2016 St. Pierre et al.
9,277,961 B2 3/2016 Panescu et al.
9,277,969 B2 3/2016 Brannan et al.
9,281,615 B1 3/2016 Plaza et al.
9,320,646 B2 4/2016 Todd et al.
9,345,481 B2 5/2016 Hall et al.
9,345,900 B2 5/2016 Wu et al.
9,351,653 B1 5/2016 Harrison
9,427,255 B2 8/2016 Griffith et al.
9,463,646 B2 10/2016 Payne et al.
9,474,565 B2 10/2016 Shikhman et al.
D772,252 S 11/2016 Myers et al.
9,486,271 B2 11/2016 Dunning
9,491,895 B2 11/2016 Steeves et al.
9,503,681 B1 11/2016 Popescu et al.
9,532,827 B2 1/2017 Morgan et al.
9,600,031 B2 3/2017 Kaneko et al.
9,603,277 B2 3/2017 Morgan et al.
D783,675 S 4/2017 Yagisawa et al.
D784,270 S 4/2017 Bhattacharya
9,629,176 B2 4/2017 Guo et al.
9,666,974 B2 5/2017 Bopp
9,713,503 B2 7/2017 Goldschmidt
9,715,271 B2 7/2017 Kaestner
9,750,563 B2 9/2017 Shikhman et al.
9,770,103 B2 9/2017 Cochran et al.
9,773,093 B2 9/2017 Bernini et al.
9,782,214 B2 10/2017 Houser et al.
9,788,907 B1 10/2017 Alvi et al.
9,804,977 B2 10/2017 Ghosh et al.
9,867,670 B2 1/2018 Brannan et al.
9,892,564 B1 2/2018 Cvetko et al.
9,907,196 B2 2/2018 Susini et al.
9,935,794 B1 4/2018 Cao et al.
9,971,395 B2 5/2018 Chenault et al.
9,974,595 B2 5/2018 Anderson et al.
9,987,068 B2 6/2018 Anderson et al.
9,987,072 B2 6/2018 McPherson
10,028,402 B1 7/2018 Walker
10,039,589 B2 8/2018 Virshek et al.
D832,211 S 10/2018 Ladd et al.
10,098,527 B2 10/2018 Weisenburgh, II et al.
10,105,470 B2 10/2018 Reasoner et al.
10,109,835 B2 10/2018 Yang
D834,541 S 11/2018 You et al.
10,117,702 B2 11/2018 Danziger et al.
10,128,612 B1 11/2018 Casto
10,136,954 B2 11/2018 Johnson et al.
10,137,245 B2 11/2018 Melker et al.
10,147,148 B2 12/2018 Wu et al.
10,166,019 B2 1/2019 Nawana et al.
10,166,061 B2 1/2019 Berry et al.
10,170,205 B2 1/2019 Curd et al.
10,201,365 B2 2/2019 Boudreaux et al.
10,262,453 B2 4/2019 Mountney et al.
10,339,496 B2 7/2019 Matson et al.
10,357,184 B2 7/2019 Crawford et al.
10,386,990 B2 8/2019 Shikhman et al.
10,441,345 B2 10/2019 Aldridge et al.
10,449,004 B2 10/2019 Ferro et al.
10,475,244 B2 11/2019 Cvetko et al.
10,493,287 B2 12/2019 Yoder et al.
10,499,847 B2 12/2019 Latimer et al.
10,499,996 B2 12/2019 de Almeida Barreto
10,523,122 B2 12/2019 Han et al.
10,531,579 B2 1/2020 Hsiao et al.
D876,466 S 2/2020 Kobayashi et al.
10,561,753 B2 2/2020 Thompson et al.
10,602,007 B2 3/2020 Takano
10,610,310 B2 4/2020 Todd et al.
10,624,667 B2 4/2020 Faller et al.
10,624,691 B2 4/2020 Wiener et al.
10,675,100 B2 6/2020 Frushour
10,687,884 B2 6/2020 Wiener et al.
10,729,502 B1 8/2020 Wolf et al.
10,743,872 B2 8/2020 Leimbach et al.
10,758,309 B1 9/2020 Chow et al.
10,758,310 B2 9/2020 Shelton, IV et al.
10,772,673 B2 9/2020 Allen, IV et al.
10,878,966 B2 12/2020 Wolf et al.
10,881,399 B2 1/2021 Shelton, IV et al.
10,898,256 B2 1/2021 Yates et al.
10,925,598 B2 2/2021 Scheib et al.
10,932,705 B2 3/2021 Muhsin et al.
10,932,772 B2 3/2021 Shelton, IV et al.
10,950,982 B2 3/2021 Regnier et al.
10,987,176 B2 4/2021 Poltaretskyi et al.
10,989,724 B1 4/2021 Holmes et al.
11,000,270 B2 5/2021 Scheib et al.
11,006,100 B1 5/2021 Douglas
D924,139 S 7/2021 Jayme
11,056,244 B2 7/2021 Shelton, IV et al.
11,058,497 B2 7/2021 Altmann et al.
11,065,079 B2 7/2021 Wolf et al.
11,071,595 B2 7/2021 Johnson et al.
D928,725 S 8/2021 Oberkircher et al.
D928,726 S 8/2021 Asher et al.
11,083,489 B2 8/2021 Fujii et al.
11,114,199 B2 9/2021 Moctezuma De La Barrera
11,116,587 B2 9/2021 Wolf et al.
D939,545 S 12/2021 Oberkircher et al.
11,218,822 B2 1/2022 Morgan et al.
11,259,793 B2 3/2022 Scheib et al.
11,259,875 B2 3/2022 Boutin et al.
11,272,839 B2 3/2022 Al-Ali et al.
11,284,963 B2 3/2022 Shelton, IV et al.
11,296,540 B2 4/2022 Kirleis et al.
11,298,128 B2 4/2022 Messerly et al.
11,304,763 B2 4/2022 Shelton, IV et al.
11,314,846 B1 4/2022 Colin et al.
11,341,726 B2 5/2022 Tsuda et al.
11,350,978 B2 6/2022 Henderson et al.
11,369,366 B2 6/2022 Scheib et al.
11,382,699 B2 7/2022 Wassall et al.
11,382,700 B2 7/2022 Calloway et al.
11,419,604 B2 8/2022 Scheib et al.
11,424,027 B2 8/2022 Shelton, IV
11,432,877 B2 9/2022 Nash et al.
11,464,581 B2 10/2022 Calloway
11,471,206 B2 10/2022 Henderson et al.
11,478,820 B2 10/2022 Bales, Jr. et al.
11,504,192 B2 11/2022 Shelton, IV et al.
11,510,720 B2 11/2022 Morgan et al.
11,510,750 B2 11/2022 Dulin et al.
11,823,374 B2 11/2023 Schneider et al.
11,836,863 B2 12/2023 Flexman et al.
12,349,861 B2 7/2025 Charles et al.
2001/0029315 A1 10/2001 Sakurai et al.
2003/0078631 A1 4/2003 Nelson et al.
2003/0199794 A1 10/2003 Sakurai et al.
2003/0199864 A1 10/2003 Eick
2004/0030328 A1 2/2004 Eggers et al.
2004/0059323 A1 3/2004 Sturm et al.
2004/0111045 A1 6/2004 Sullivan et al.
2004/0164983 A1 8/2004 Khozai
2005/0010209 A1 1/2005 Lee et al.
2005/0013459 A1 1/2005 Maekawa
2005/0113823 A1 5/2005 Reschke et al.
2005/0165390 A1 7/2005 Mauti et al.
2005/0229110 A1 10/2005 Gegner et al.
2005/0251233 A1 11/2005 Kanzius
2006/0082542 A1 4/2006 Morita et al.
2006/0085049 A1 4/2006 Cory et al.
2006/0136622 A1 6/2006 Rouvelin et al.
2006/0149418 A1 7/2006 Anvari
2006/0256516 A1 11/2006 Cho
2007/0076363 A1 4/2007 Liang et al.
2007/0211930 A1 9/2007 Dolwick et al.
2007/0282321 A1 12/2007 Shah et al.
2008/0072896 A1 3/2008 Setzer et al.
2008/0129465 A1 6/2008 Rao
2008/0249377 A1 10/2008 Molducci et al.

(56) References Cited

U.S. PATENT DOCUMENTS

2008/0316304 A1 12/2008 Claus et al.
2009/0036884 A1 2/2009 Gregg et al.
2009/0131929 A1 5/2009 Shimizu
2009/0192524 A1 7/2009 Itkowitz et al.
2009/0216091 A1 8/2009 Arndt
2009/0234352 A1 9/2009 Behnke et al.
2010/0036405 A1 2/2010 Giordano et al.
2010/0042010 A1 2/2010 Dekker et al.
2010/0053213 A1 3/2010 Ishida et al.
2010/0069939 A1 3/2010 Konishi
2010/0076453 A1 3/2010 Morris et al.
2010/0092006 A1 4/2010 Rosen
2010/0120266 A1 5/2010 Rimborg
2010/0198200 A1 8/2010 Horvath
2010/0312239 A1 12/2010 Sclig
2011/0105895 A1 5/2011 Kornblau et al.
2011/0118748 A1 5/2011 Itkowitz
2011/0125149 A1 5/2011 El-Galley et al.
2011/0130689 A1 6/2011 Cohen et al.
2011/0190588 A1 8/2011 Mckay
2011/0245630 A1 10/2011 St. Pierre et al.
2011/0273465 A1 11/2011 Konishi et al.
2011/0298814 A1 12/2011 Mathew et al.
2011/0306840 A1 12/2011 Allen et al.
2012/0029304 A1 2/2012 Medina et al.
2012/0082036 A1 4/2012 Abedi et al.
2012/0116380 A1 5/2012 Madan et al.
2012/0132661 A1 5/2012 Gu et al.
2013/0031201 A1 1/2013 Kagan et al.
2013/0038707 A1 2/2013 Cunningham et al.
2013/0176220 A1 7/2013 Merschon et al.
2013/0197357 A1 8/2013 Green et al.
2013/0197503 A1 8/2013 Orszulak
2013/0267975 A1 10/2013 Timm et al.
2013/0268283 A1 10/2013 Vann et al.
2013/0303851 A1 11/2013 Griffith et al.
2013/0321159 A1 12/2013 Schofield et al.
2014/0009894 A1 1/2014 Yu
2014/0052150 A1 2/2014 Taylor et al.
2014/0058714 A1 2/2014 Boyer
2014/0087573 A1 3/2014 Kroeckel
2014/0155721 A1 6/2014 Hauck et al.
2014/0179997 A1 6/2014 Von Grunberg et al.
2014/0194683 A1 7/2014 Nakaguchi
2014/0221740 A1 8/2014 Kawula et al.
2014/0226572 A1 8/2014 Thota et al.
2014/0262598 A1 9/2014 Miki et al.
2014/0263552 A1 9/2014 Hall et al.
2014/0343358 A1 11/2014 Hameed et al.
2015/0019259 A1* 1/2015 Qureshi ................ G16H 40/20
705/3
2015/0057575 A1 2/2015 Tsusaka et al.
2015/0070388 A1 3/2015 Sheaffer et al.
2015/0190189 A1 7/2015 Yates et al.
2015/0265369 A1 9/2015 Garbey et al.
2015/0272575 A1 10/2015 Leimbach et al.
2015/0289929 A1 10/2015 Toth et al.
2016/0045247 A1 2/2016 Heim et al.
2016/0058286 A1 3/2016 Joshua et al.
2016/0066184 A1 3/2016 Bhargav-Spantzel et al.
2016/0074096 A1 3/2016 Lieu
2016/0120591 A1 5/2016 Smith et al.
2016/0174897 A1 6/2016 Sherman
2016/0225192 A1 8/2016 Jones et al.
2016/0287312 A1 10/2016 Tegg et al.
2016/0287337 A1 10/2016 Aram et al.
2017/0000553 A1 1/2017 Wiener et al.
2017/0090507 A1 3/2017 Wiener et al.
2017/0189096 A1 7/2017 Danziger et al.
2017/0202595 A1 7/2017 Shelton, IV
2017/0209225 A1 7/2017 Wu
2017/0251305 A1 8/2017 Fathollahi
2017/0252091 A1 9/2017 Honda
2017/0258526 A1 9/2017 Lang
2017/0296036 A1 10/2017 Newman
2017/0296213 A1 10/2017 Swensgard et al.
2017/0319259 A1 11/2017 Dunning
2017/0333275 A1 11/2017 Itkowitz et al.
2017/0360466 A1 12/2017 Brown et al.
2017/0367766 A1 12/2017 Mahfouz
2018/0014872 A1 1/2018 Dickerson
2018/0032130 A1 2/2018 Meglan
2018/0042659 A1 2/2018 Rupp et al.
2018/0043037 A1 2/2018 Dalma-weiszhausz et al.
2018/0049795 A1 2/2018 Swayze et al.
2018/0065248 A1 3/2018 Barral et al.
2018/0078216 A1 3/2018 Baker et al.
2018/0082480 A1 3/2018 White et al.
2018/0092699 A1 4/2018 Finley
2018/0099161 A1 4/2018 Honda
2018/0168741 A1 6/2018 Swayze et al.
2018/0173323 A1 6/2018 Harvey et al.
2018/0221005 A1 8/2018 Hamel et al.
2018/0228528 A1 8/2018 Fraasch et al.
2018/0228555 A1 8/2018 Charron et al.
2018/0235441 A1 8/2018 Huang et al.
2018/0243573 A1 8/2018 Yoder et al.
2018/0262916 A1 9/2018 Polley et al.
2018/0263557 A1 9/2018 Kahlman
2018/0289338 A1 10/2018 Meador et al.
2018/0317826 A1 11/2018 Muhsin et al.
2018/0333207 A1 11/2018 Moctezuma De la Barrera
2018/0368930 A1 12/2018 Esterberg et al.
2019/0006047 A1 1/2019 Gorek et al.
2019/0035153 A1 1/2019 Dange
2019/0038362 A1 2/2019 Nash et al.
2019/0069957 A1 3/2019 Barral et al.
2019/0104919 A1* 4/2019 Shelton, IV ........... A61B 18/00
2019/0117326 A1 4/2019 Wada
2019/0125361 A1 5/2019 Shelton, IV et al.
2019/0125451 A1 5/2019 Srimohanarajah et al.
2019/0125454 A1 5/2019 Stokes et al.
2019/0125455 A1 5/2019 Shelton, IV et al.
2019/0125457 A1 5/2019 Parihar et al.
2019/0125459 A1 5/2019 Shelton et al.
2019/0183576 A1 6/2019 Fahim et al.
2019/0183591 A1* 6/2019 Johnson ................ B25J 9/1666
2019/0200844 A1 7/2019 Shelton, IV et al.
2019/0200906 A1 7/2019 Shelton, IV et al.
2019/0200981 A1 7/2019 Harris et al.
2019/0200987 A1 7/2019 Shelton, IV et al.
2019/0201046 A1 7/2019 Shelton, IV et al.
2019/0201102 A1 7/2019 Shelton, IV et al.
2019/0201114 A1 7/2019 Shelton, IV et al.
2019/0201116 A1 7/2019 Shelton, IV et al.
2019/0201117 A1 7/2019 Yates et al.
2019/0201127 A1 7/2019 Shelton, IV et al.
2019/0201136 A1 7/2019 Shelton, IV et al.
2019/0201137 A1 7/2019 Shelton, IV et al.
2019/0201140 A1 7/2019 Yates et al.
2019/0201158 A1 7/2019 Shelton, IV et al.
2019/0205001 A1 7/2019 Messerly et al.
2019/0206004 A1 7/2019 Shelton, IV et al.
2019/0206562 A1 7/2019 Shelton, IV et al.
2019/0206563 A1 7/2019 Shelton, IV et al.
2019/0206565 A1* 7/2019 Shelton, IV ........... A61B 90/90
2019/0206569 A1 7/2019 Shelton et al.
2019/0224434 A1 7/2019 Silver et al.
2019/0236840 A1 8/2019 Zuckerman et al.
2019/0247141 A1 8/2019 Batchelor et al.
2019/0278262 A1 9/2019 Taylor et al.
2019/0279524 A1 9/2019 Stoyanov et al.
2019/0282307 A1 9/2019 Azizian et al.
2019/0290297 A1 9/2019 Haider et al.
2019/0348169 A1 11/2019 Gibby et al.
2019/0371012 A1 12/2019 Flexman et al.
2020/0004487 A1 1/2020 Hanajima et al.
2020/0015895 A1 1/2020 Frielinghaus et al.
2020/0015898 A1 1/2020 Scheib et al.
2020/0015899 A1 1/2020 Scheib et al.
2020/0015900 A1 1/2020 Scheib et al.
2020/0015902 A1 1/2020 Scheib et al.
2020/0015906 A1 1/2020 Scheib et al.
2020/0015907 A1 1/2020 Scheib

(56) References Cited

U.S. PATENT DOCUMENTS

2020/0015914 A1 1/2020 Scheib et al.
2020/0015924 A1 1/2020 Scheib et al.
2020/0038120 A1 2/2020 Ziraknejad et al.
2020/0078070 A1 3/2020 Henderson et al.
2020/0078071 A1 3/2020 Asher
2020/0078076 A1 3/2020 Henderson et al.
2020/0078078 A1 3/2020 Henderson et al.
2020/0078080 A1 3/2020 Henderson et al.
2020/0078081 A1 3/2020 Jayme et al.
2020/0078082 A1 3/2020 Henderson et al.
2020/0078083 A1 3/2020 Sprinkle et al.
2020/0078089 A1 3/2020 Henderson et al.
2020/0078110 A1 3/2020 Henderson et al.
2020/0078111 A1 3/2020 Oberkircher et al.
2020/0078112 A1 3/2020 Henderson et al.
2020/0078113 A1 3/2020 Sawhney et al.
2020/0078114 A1 3/2020 Asher et al.
2020/0078115 A1 3/2020 Asher et al.
2020/0078116 A1 3/2020 Oberkircher et al.
2020/0078117 A1 3/2020 Henderson et al.
2020/0078118 A1 3/2020 Henderson et al.
2020/0078119 A1 3/2020 Henderson et al.
2020/0078120 A1 3/2020 Aldridge et al.
2020/0081585 A1 3/2020 Petre et al.
2020/0090808 A1 3/2020 Carroll et al.
2020/0093357 A1 3/2020 Scott et al.
2020/0100825 A1 4/2020 Henderson et al.
2020/0100830 A1 4/2020 Henderson et al.
2020/0106220 A1 4/2020 Henderson et al.
2020/0159313 A1 5/2020 Gibby et al.
2020/0237031 A1 7/2020 Daniels et al.
2020/0237452 A1 7/2020 Wolf et al.
2020/0246084 A1 8/2020 Azizian
2020/0268469 A1 8/2020 Wolf et al.
2020/0268472 A1 8/2020 Wolf et al.
2020/0305924 A1 10/2020 Carroll
2020/0305945 A1 10/2020 Morgan et al.
2020/0315707 A1 10/2020 Venkataraman
2020/0315734 A1 10/2020 El Amm
2020/0322516 A1 10/2020 Doser et al.
2020/0342228 A1 10/2020 Prevrhal et al.
2020/0359892 A1 11/2020 Rollins et al.
2020/0384287 A1 12/2020 Hetz
2020/0405529 A1 12/2020 Taylor et al.
2021/0000564 A1 1/2021 Amanatullah et al.
2021/0015343 A1 1/2021 Uyama et al.
2021/0093390 A1 4/2021 Poltaretskyi et al.
2021/0121246 A1 4/2021 Gudalo
2021/0128254 A1 5/2021 Geric et al.
2021/0158779 A1 5/2021 Singh
2021/0169578 A1 6/2021 Calloway et al.
2021/0169581 A1 6/2021 Calloway et al.
2021/0174956 A1 6/2021 Mcginley et al.
2021/0192759 A1 6/2021 Lang
2021/0193681 A1 6/2021 Baek
2021/0196381 A1 7/2021 Eckert et al.
2021/0196383 A1 7/2021 Shelton, IV et al.
2021/0196425 A1 7/2021 Shelton et al.
2021/0203889 A1 7/2021 Fung et al.
2021/0205020 A1 7/2021 Shelton, IV et al.
2021/0212717 A1 7/2021 Yates et al.
2021/0236755 A1 8/2021 King et al.
2021/0259789 A1 8/2021 Wright et al.
2021/0264680 A1 8/2021 Cvetko, Ph.D et al.
2021/0267664 A1 9/2021 Lennartz et al.
2021/0306691 A1 9/2021 Thomas et al.
2021/0307861 A1 10/2021 Hufford et al.
2021/0313052 A1 10/2021 Makrinich et al.
2021/0333864 A1 10/2021 Harvey et al.
2021/0346092 A1 11/2021 Redmond et al.
2021/0369394 A1 12/2021 Braido et al.
2021/0385889 A1 12/2021 Patel
2022/0032442 A1 2/2022 Sheffield et al.
2022/0104896 A1 4/2022 Shelton, IV et al.
2022/0104897 A1 4/2022 Shelton, IV et al.
2022/0104911 A1 4/2022 Shelton, IV et al.
2022/0104912 A1 4/2022 Shelton, IV et al.
2022/0142573 A1 5/2022 Li et al.
2022/0151704 A1 5/2022 Nikou
2022/0155910 A1 5/2022 Jeong
2022/0160428 A1 5/2022 Murray et al.
2022/0188545 A1 6/2022 Nagar et al.
2022/0237878 A1 7/2022 Tartz et al.
2022/0257333 A1 8/2022 Haider
2022/0261056 A1 8/2022 Motoi et al.
2022/0283631 A1 9/2022 Peng
2022/0287676 A1 9/2022 Steines et al.
2022/0313338 A1 10/2022 Carroll et al.
2022/0313341 A1 10/2022 Wiener et al.
2022/0313342 A1 10/2022 Leuck et al.
2022/0313357 A1 10/2022 Geresy et al.
2022/0313369 A1 10/2022 Oberkircher et al.
2022/0313370 A1 10/2022 Morgan et al.
2022/0313371 A1 10/2022 Morgan et al.
2022/0313372 A1 10/2022 Herman et al.
2022/0313373 A1 10/2022 Morgan et al.
2022/0317750 A1 10/2022 Jayme et al.
2022/0317751 A1 10/2022 Samuel et al.
2022/0318179 A1 10/2022 Morgan et al.
2022/0319685 A1 10/2022 Vachon et al.
2022/0319693 A1 10/2022 Oberkircher et al.
2022/0321059 A1 10/2022 Samuel et al.
2022/0322523 A1 10/2022 Jayme et al.
2022/0331013 A1 10/2022 Shelton, IV et al.
2022/0331047 A1 10/2022 Shelton, IV et al.
2022/0331049 A1 10/2022 Shelton, IV et al.
2022/0331050 A1 10/2022 Shelton, IV et al.
2022/0331051 A1 10/2022 Shelton, IV et al.
2022/0331052 A1 10/2022 Shelton, IV et al.
2022/0331053 A1 10/2022 Kimball et al.
2022/0331054 A1 10/2022 Kimball et al.
2022/0331056 A1 10/2022 Shelton, IV et al.
2022/0334787 A1 10/2022 Jogan et al.
2022/0335604 A1 10/2022 Vanosdoll et al.
2022/0335660 A1 10/2022 Shelton, IV et al.
2022/0335696 A1 10/2022 Shelton, IV et al.
2022/0336078 A1 10/2022 Wise et al.
2022/0336097 A1 10/2022 Shelton, IV et al.
2022/0337891 A1 10/2022 Burnley et al.
2022/0338049 A1 10/2022 Ross et al.
2022/0387128 A1 12/2022 Bail et al.
2023/0038130 A1 2/2023 Cvetko et al.
2023/0061534 A1 3/2023 Stopek
2023/0071306 A1 3/2023 Miller et al.
2023/0072423 A1 3/2023 Osborn et al.
2023/0121709 A1 4/2023 Xu et al.
2023/0157757 A1 5/2023 Braido et al.
2023/0157762 A1 5/2023 Braido et al.
2024/0130795 A1 4/2024 Clayton et al.
2024/0138931 A1 5/2024 Lefauconnier
2024/0176441 A1 5/2024 Yang et al.
2024/0325085 A1 10/2024 Ryan et al.

FOREIGN PATENT DOCUMENTS

EP 0408160 A1 1/1991
EP 0473987 A1 3/1992
EP 0929263 B1 7/1999
EP 1006892 B1 6/2009
EP 2942023 A2 11/2015
EP 3053279 A1 8/2016
EP 3387982 A1 10/2018
JP 2000-271145 A 10/2000
JP 2001029353 A 2/2001
JP 2006-149560 A 6/2006
JP 2007-007041 A 1/2007
JP 2007-029232 A 2/2007
JP 2021-045341 A 3/2021
WO WO-0112089 A1 2/2001
WO WO-2008053485 A1 5/2008
WO 2014/010177 A1 1/2014
WO WO-2014031800 A1 2/2014
WO WO-2014071184 A1 5/2014
WO WO-2015047693 A1 4/2015

(56) References Cited

FOREIGN PATENT DOCUMENTS

| | | | |
|---|---|---|---|
| WO | 2016/013636 | A1 | 1/2016 |
| WO | 2016154557 | A1 | 9/2016 |
| WO | WO-2017058617 | A2 | 4/2017 |
| WO | 2017/099153 | A1 | 6/2017 |
| WO | 2017/221367 | A1 | 12/2017 |
| WO | WO-2018116247 | A1 | 6/2018 |
| WO | WO-2019215354 | A1 | 11/2019 |
| WO | 2020112217 | A1 | 6/2020 |
| WO | 2020180917 | A1 | 9/2020 |
| WO | WO-2021044136 | A1 | 3/2021 |
| WO | 2021/146313 | A1 | 7/2021 |

OTHER PUBLICATIONS

IEEE Std 802.3-2012 (Revision of IEEE Std 802.3-2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

Vávra et al., "Recent Development of Augmented Reality in Surgery: A Review", Journal of Healthcare Engineering, vol. 2017, Article ID 4574172, Aug. 21, 2017, pp. 1-9.

International Search Report and Written Opinion received for PCT Application No. PCT/IB2022/053360, Mailed on Jul. 4, 2022, 12 pages.

International Search Report and Written Opinion received for PCT Application No. PCT/IB2022/053362, Mailed on Jul. 1, 2022, 13 pages.

International Search Report and Written Opinion received for PCT Application No. PCT/IB2022/053363, Mailed on Jun. 30, 2022, 14 pages.

International Search Report and Written Opinion received for PCT Application No. PCT/IB2022/053364, Mailed on Jul. 8, 2022, 11 pages.

International Search Report and Written Opinion received for PCT Application No. PCT/IB2022/053365, Mailed on Jul. 4, 2022, 16 pages.

International Search Report and Written Opinion received for PCT Application No. PCT/IB2022/053369, Mailed on Jul. 13, 2022, 12 pages.

International Search Report and Written Opinion received for PCT Application No. PCT/IB2022/053370, Mailed on Jul. 15, 2022, 14 pages.

International Search Report and Written Opinion received for PCT Application No. PCT/IB2022/053371, Mailed on Jul. 5, 2022, 12 pages.

International Search Report and Written Opinion received for PCT Application No. PCT/IB2022/053377, Mailed on Jun. 22, 2022, 12 pages.

International Search Report and Written Opinion received for PCT Application No. PCT/IB2022/053378, Mailed on Jul. 7, 2022, 13 pages.

Invitation to Pay Additional Fees received for PCT Application No. PCT/IB2022/053375, Mailed on Jul. 15, 2022, 11 pages.

International Search Report and Written Opinion received for PCT Application No. PCT/IB2022/053375, Mailed on Oct. 4, 2022, 22 pages.

Kaushik et al., "Emerging Thermal Technology Enabled Augmented Reality", Advanced Functional Materials, vol. 31, No. 39, Feb. 17, 2021., pp. 1-27.

Zherdeva et al., "Virtual Scalpel Simulation in the VR and AR Environments", Proceedings Of SPIE, vol. 11310, Feb. 19, 2020, 7 pages.

* cited by examiner

5200

| WHAT THE HUB KNOWS | THORACIC PROCEDURE | NOT A WEDGE PROCEDURE | CONFIRM PATIENT | VATS | CONFIRM PATIENT IS IN O.R. | PATIENT UNDER | PROCEDURE BEGINS | CONFIRM LOBECTOMY vs. SEGMENTECTOMY LAP PORTION STARTS |
|---|---|---|---|---|---|---|---|---|
| TYPE OF DATA | SELECT PATIENT DATA | SCAN PRODUCTS | UNQUE ID | SMOKE EVAC. DATA INSUFFLATION DATA SCOPE DATA | EKG DATA | EKG, BP AND VENTILATOR DATA | VENTILATOR DATA | SCOPE DATA |
| | 5202 | 5204 | 5206 | 5208 | 5210 | 5212 | 5214 | 5216 |
| PROCEDURE STEP | PULL ELECTRONIC MEDICAL RECORDS | SCAN INCOMING SUPPLIES | SCAN PATIENT BAND | TURN ON HUB AUXILIARY EQUIPMENT | ATTACH EKG | INDUCE ANESTHESIA | COLLAPSE LUNG | SCOPE IMAGE |

| WHAT THE HUB KNOWS | DISSECT TO MOBILIZE LUNG | LIGATE ARTERY & VEIN | TRANSECT PARENCHYMA | DISSECT NODES LEAK TEST | PATIENT ENERGENCE | PATIENT TRANSFER TO RECOVERY ROOM |
|---|---|---|---|---|---|---|
| TYPE OF DATA | GENERATOR DATA | STAPLER DATA | STAPLER & CATRIDGE DATA | GENERATOR DATA | VENTILATOR DATA | LOSS OF EKG DATA LOSS OF BP DATA |
| | 5218 | 5220 | 5222 | 5224 | 5226 | 5228 |
| PROCEDURE STEP | DISSECTION | LIGATION | SEGMENTECTOMY | NODE DISSECTION | REVERSE ANESTHESIA | REMOVE MONITORS |

FIG. 11

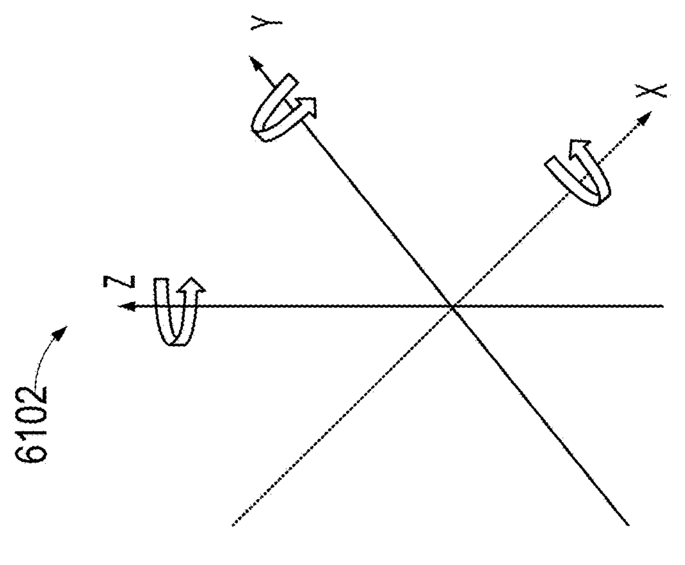
FIG. 22C
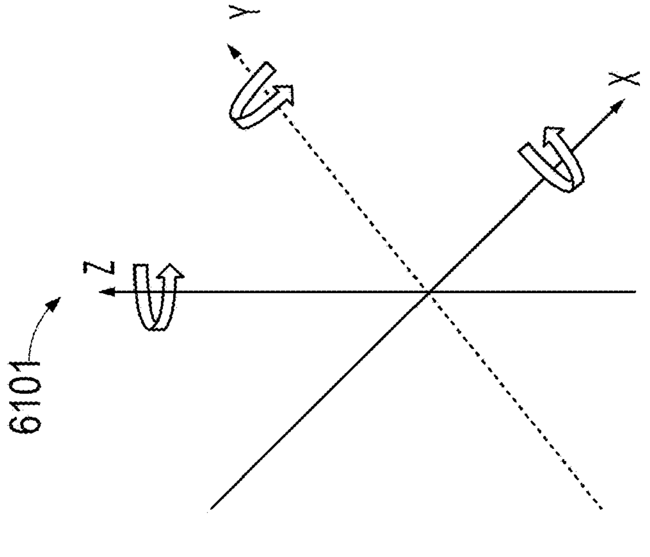
FIG. 22B
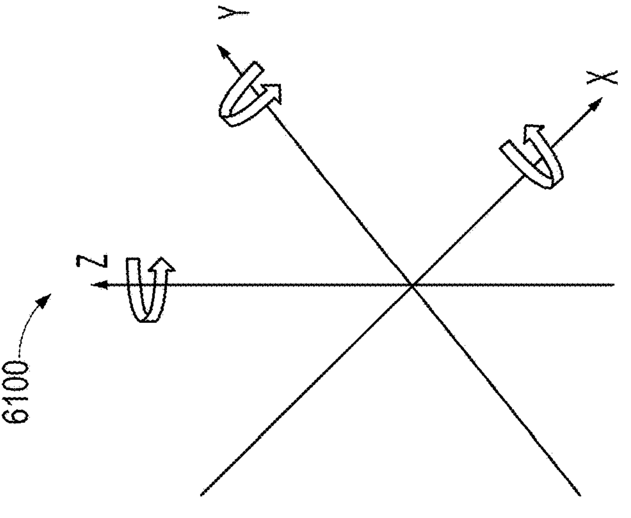
FIG. 22A

6130
T
6131
6132''
End Effector

6130
T
6131
6132'
End Effector

6130
T
6131
6132
End Effector

UTILIZATION OF SURGICAL DATA VALUES AND SITUATIONAL AWARENESS TO CONTROL THE OVERLAY IN SURGICAL FIELD VIEW

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices including energy, staplers, or combined energy and staplers. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various instances, the present disclosure provides a surgical visualization system including an imaging device, a display configured to show a livestream of a surgical field of a surgical procedure, and a control module configured to detect surgical data, assign display priority values to the surgical data, determine a display arrangement of the surgical data based on the display priority values, and present the surgical data on the display in accordance with the display arrangement. The livestream is captured by the imaging device.

In various instances, the present disclosure provides a surgical visualization system disclosing an imaging device, a display configured to show a livestream of a surgical field of a surgical procedure, and a control module, configured to detect first surgical data, generate a first visual representation of the first surgical data for presenting the first surgical data on the display, detect second surgical data, generate a second visual representation of the second surgical data for presenting the second surgical data on the display, detect a display conflict between the first surgical data and the second surgical data, determine a resolution of the display conflict in favor of one of one of the first visual representation and the second visual representation based on at least one of the first surgical data and the second surgical data, and determine a display arrangement of the first visual representation and the second visual representation in accordance with the resolution. The livestream is captured by the imaging device.

FIGURES

The various aspects described herein, both as to organization and methods of operation, together with further objects and advantages thereof, may best be understood by reference to the following description, taken in conjunction with the accompanying drawings as follows.

FIG. 11 illustrates a timeline of a situational awareness surgical procedure, according to one aspect of this disclosure.

FIGS. 22A-22C illustrate display arrangements, in accordance with at least one aspect of the present disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Figure 1:
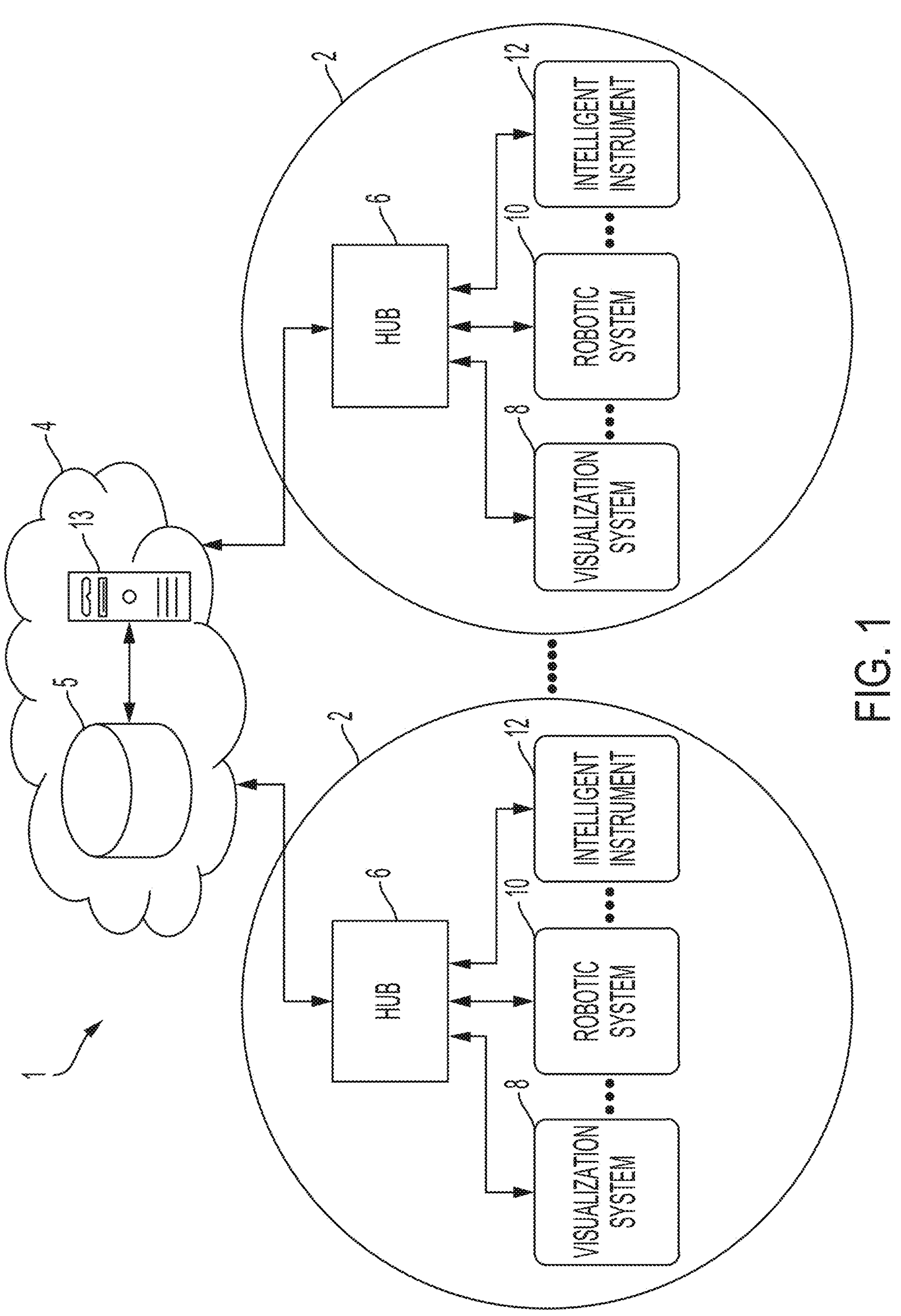
FIG. 1 is a block diagram of a computer-implemented interactive surgical system, according to one aspect of this disclosure.

Applicant of the present application owns the following U.S. patent applications filed concurrently herewith, the disclosures of each of which is herein incorporated by reference in its entirety:

- U.S. patent application Ser. No. 17/688,589, titled METHOD FOR INTRAOPERATIVE DISPLAY FOR SURGICAL SYSTEMS;
- U.S. patent application Ser. No. 17/688,605, titled SELECTIVE AND ADJUSTABLE MIXED REALITY OVERLAY IN SURGICAL FIELD VIEW;
- U.S. patent application Ser. No. 17/688,615, titled RISK BASED PRIORITIZATION OF DISPLAY ASPECTS IN SURGICAL FIELD VIEW;
- U.S. patent application Ser. No. 17/688,626, titled SYSTEMS AND METHODS FOR CONTROLLING SURGICAL DATA OVERLAY;
- U.S. patent application Ser. No. 17/688,633, titled SYSTEMS AND METHODS FOR CHANGING DISPLAY OVERLAY OF SURGICAL FIELD VIEW BASED ON TRIGGERING EVENTS;
- U.S. patent application Ser. No. 17/688,638, titled CUSTOMIZATION OF OVERLAID DATA AND CONFIGURATION;
- U.S. patent application Ser. No. 17/688,641, titled CUSTOMIZATION OF OVERLAID DATA AND CONFIGURATION;
- U.S. patent application Ser. No. 17/688,646, titled COOPERATIVE OVERLAYS OF INTERACTING INSTRUMENTS WHICH RESULT IN BOTH OVERLAYS BEING EFFECTED;
- U.S. patent application Ser. No. 17/688,651, titled ANTICIPATION OF INTERACTIVE UTILIZATION OF COMMON DATA OVERLAYS BY DIFFERENT USERS;
- U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN;
- U.S. patent application Ser. No. 17/688,655, titled SYSTEM AND METHOD FOR TRACKING A PORTION OF THE USER AS A PROXY FOR NON-MONITORED INSTRUMENT;
- U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;
- U.S. patent application Ser. No. 17/688,660, titled COOPERATION AMONG MULTIPLE DISPLAY SYSTEMS TO PROVIDE A HEALTHCARE USER CUSTOMIZED INFORMATION;
- U.S. patent application Ser. No. 17/688,663, titled INTRAOPERATIVE DISPLAY FOR SURGICAL SYSTEMS;
- U.S. patent application Ser. No. 17/688,667, titled ADAPTATION AND ADJUSTABILITY OR OVERLAID INSTRUMENT INFORMATION FOR SURGICAL SYSTEMS;
- U.S. patent application Ser. No. 17/688,671, titled MIXED REALITY FEEDBACK SYSTEMS THAT

COOPERATE TO INCREASE EFFICIENT PERCEPTION OF COMPLEX DATA FEEDS.

Applicant of this application owns the following U.S. patent applications, the disclosure of each of which is herein incorporated by reference in its entirety:

- U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;
- U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
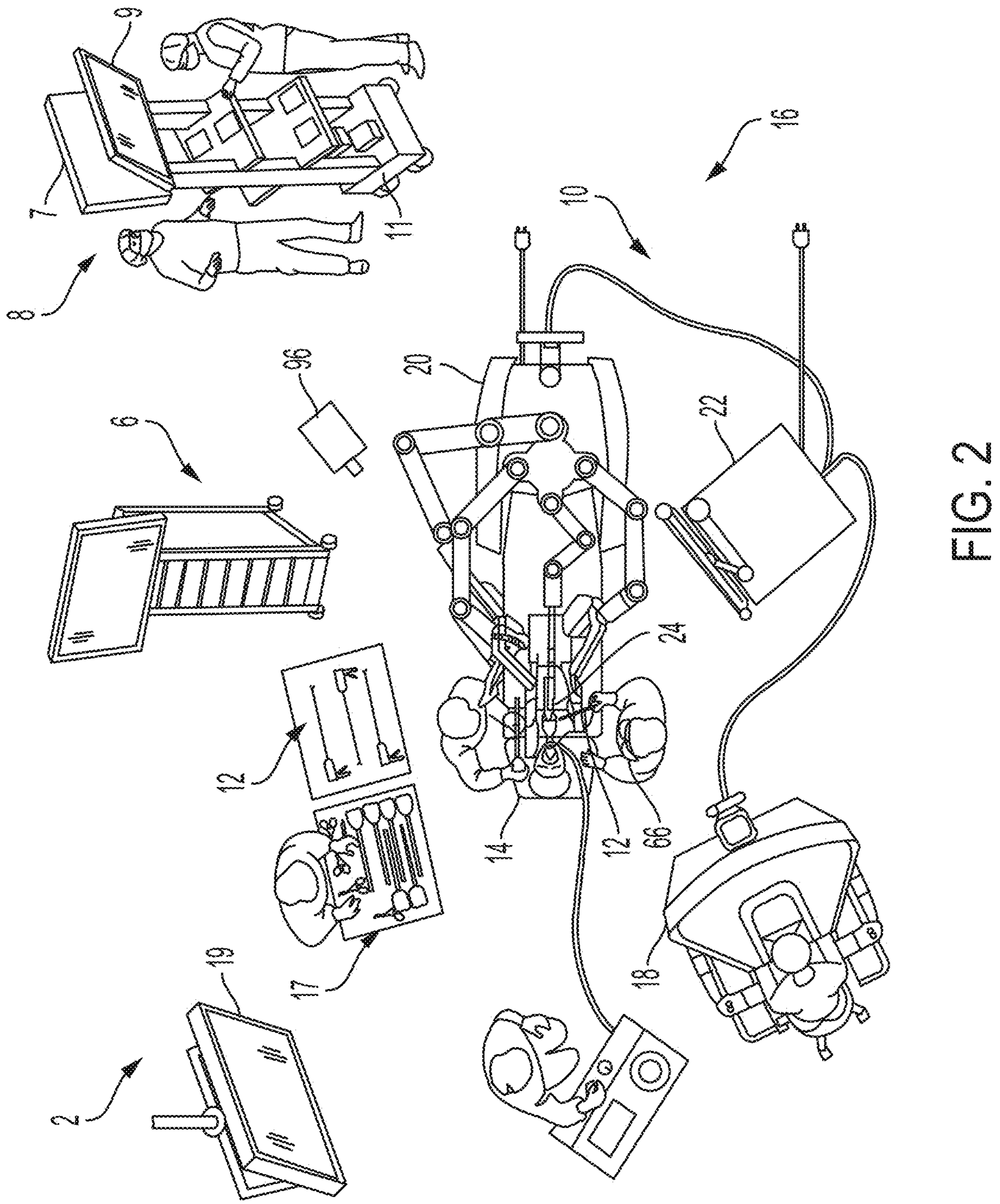
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
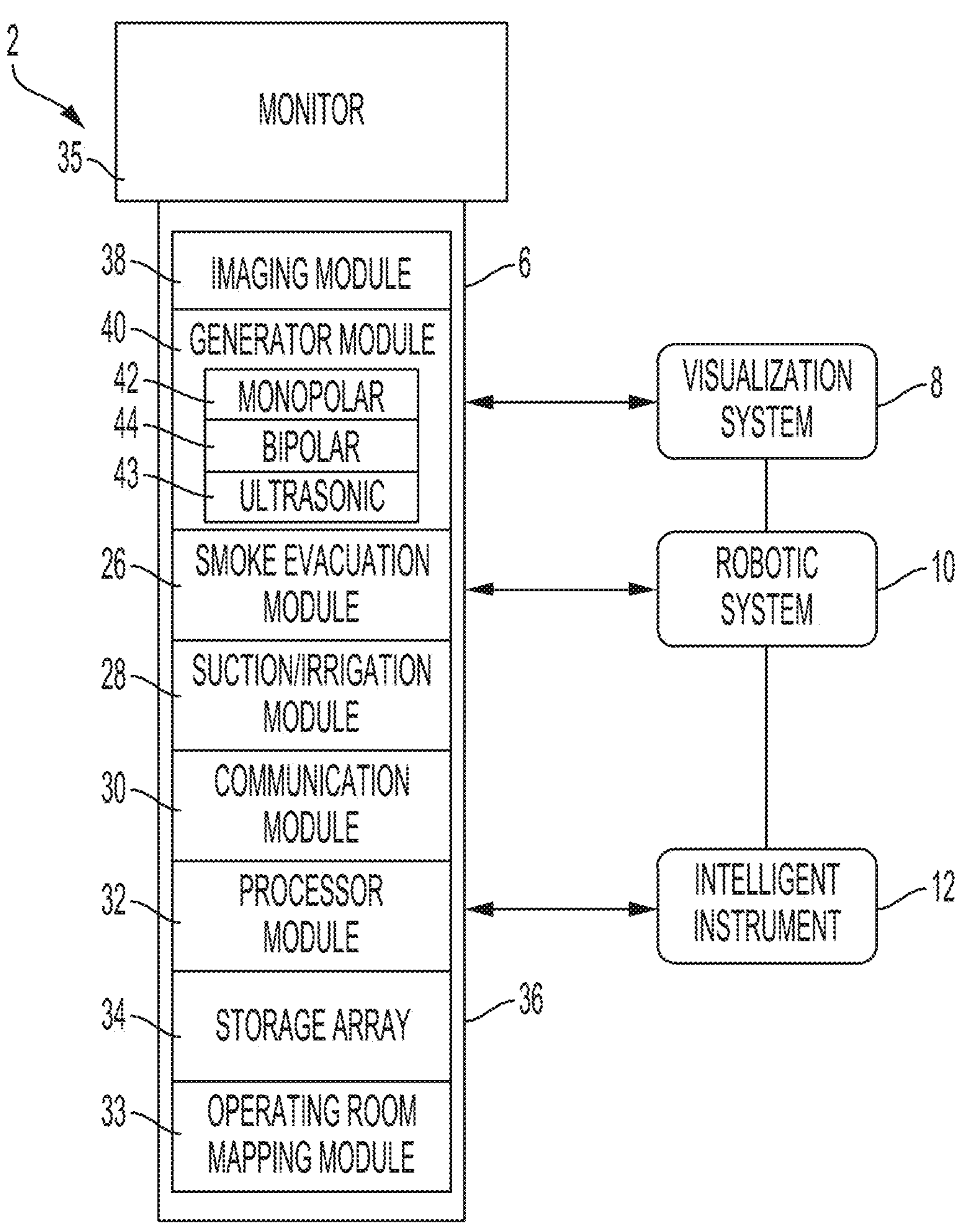
FIG. 3 is a surgical hub paired with a visualization system, a robotic system, and an intelligent instrument, according to one aspect of this disclosure.
Figure 10:
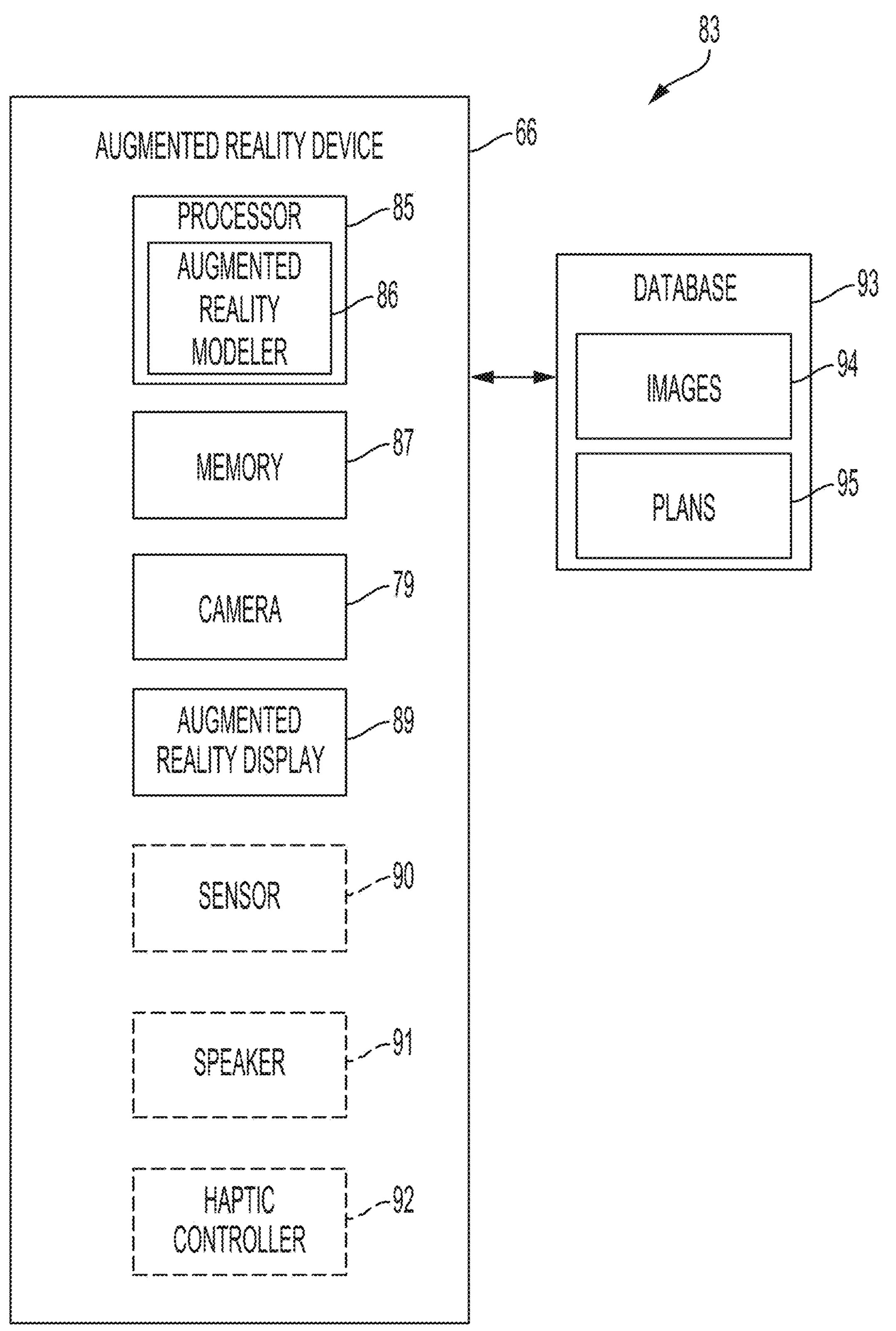
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
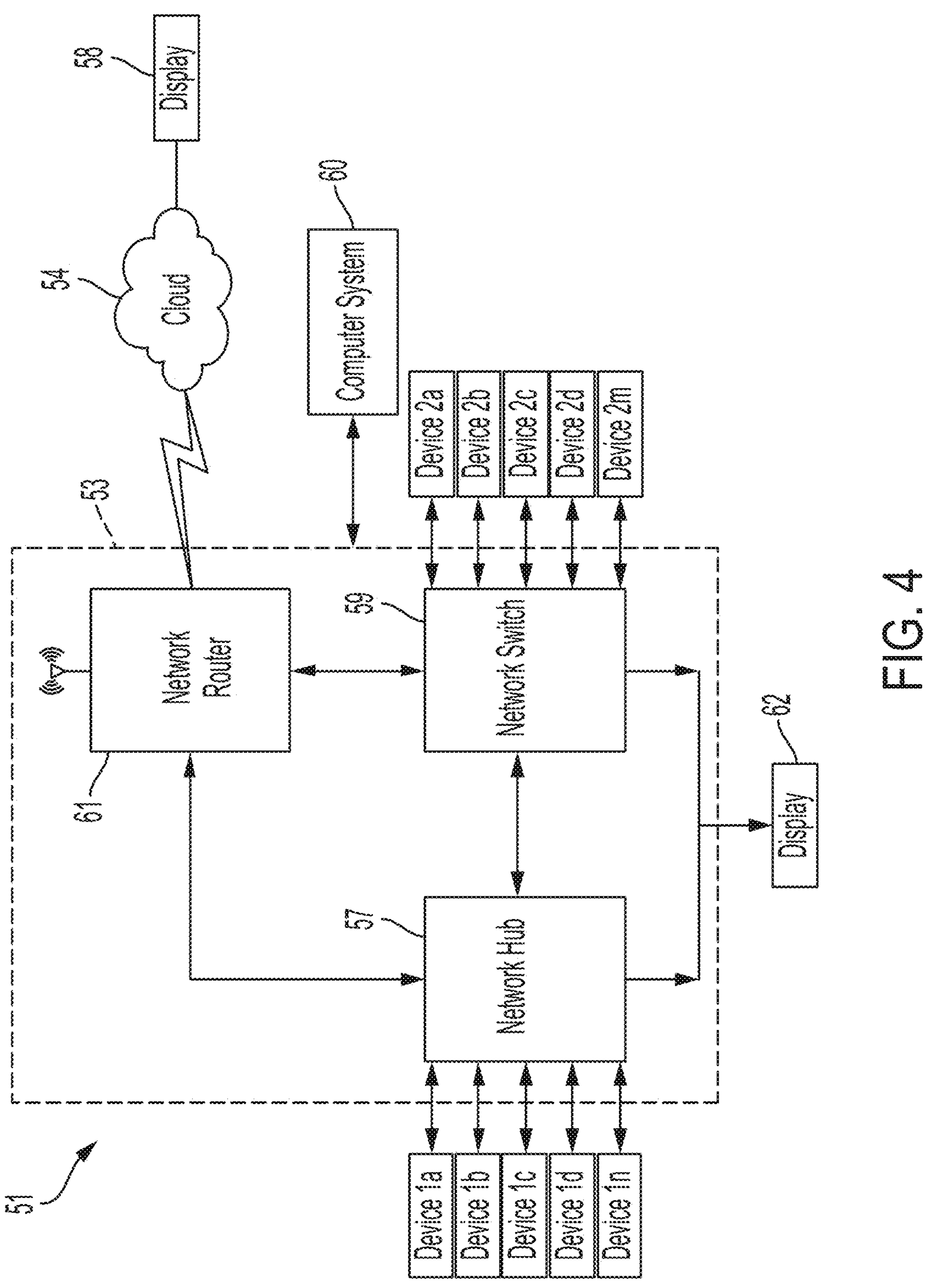
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1*a*-1*n* in the operating theater may be coupled to the modular communication hub 53. The network hub 57 and/or the network switch 59 may be coupled to a network router 61 to connect the devices 1*a*-1*n* to the cloud 54 or the local computer system 60. Data associated with the devices 1*a*-1*n* may be transferred to cloud-based computers via the router for remote data processing and manipulation. The operating theater devices 1*a*-1*n* may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
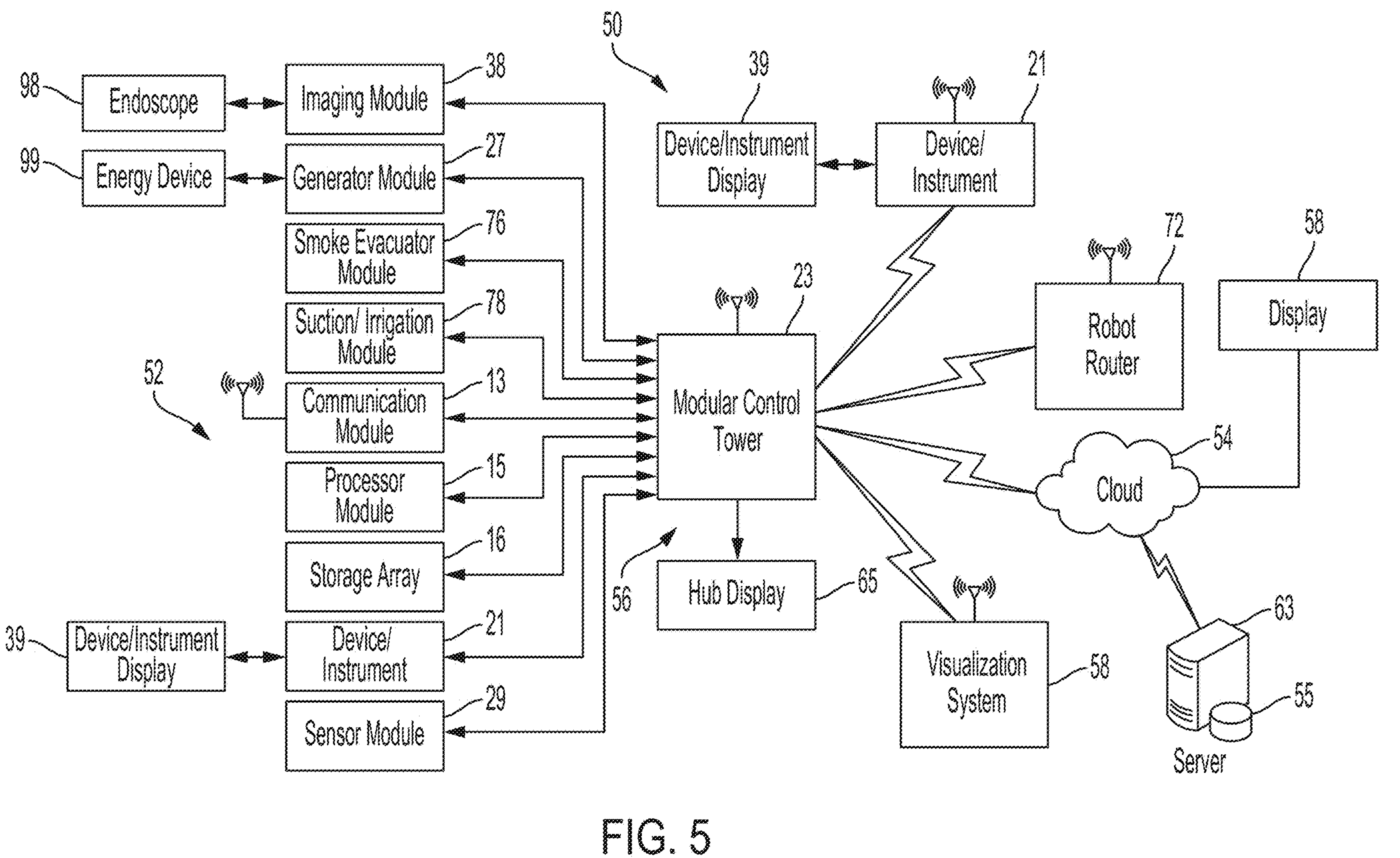
FIG. 5 illustrates a computer-implemented interactive surgical system, according to one aspect of this disclosure.
Figure 6:
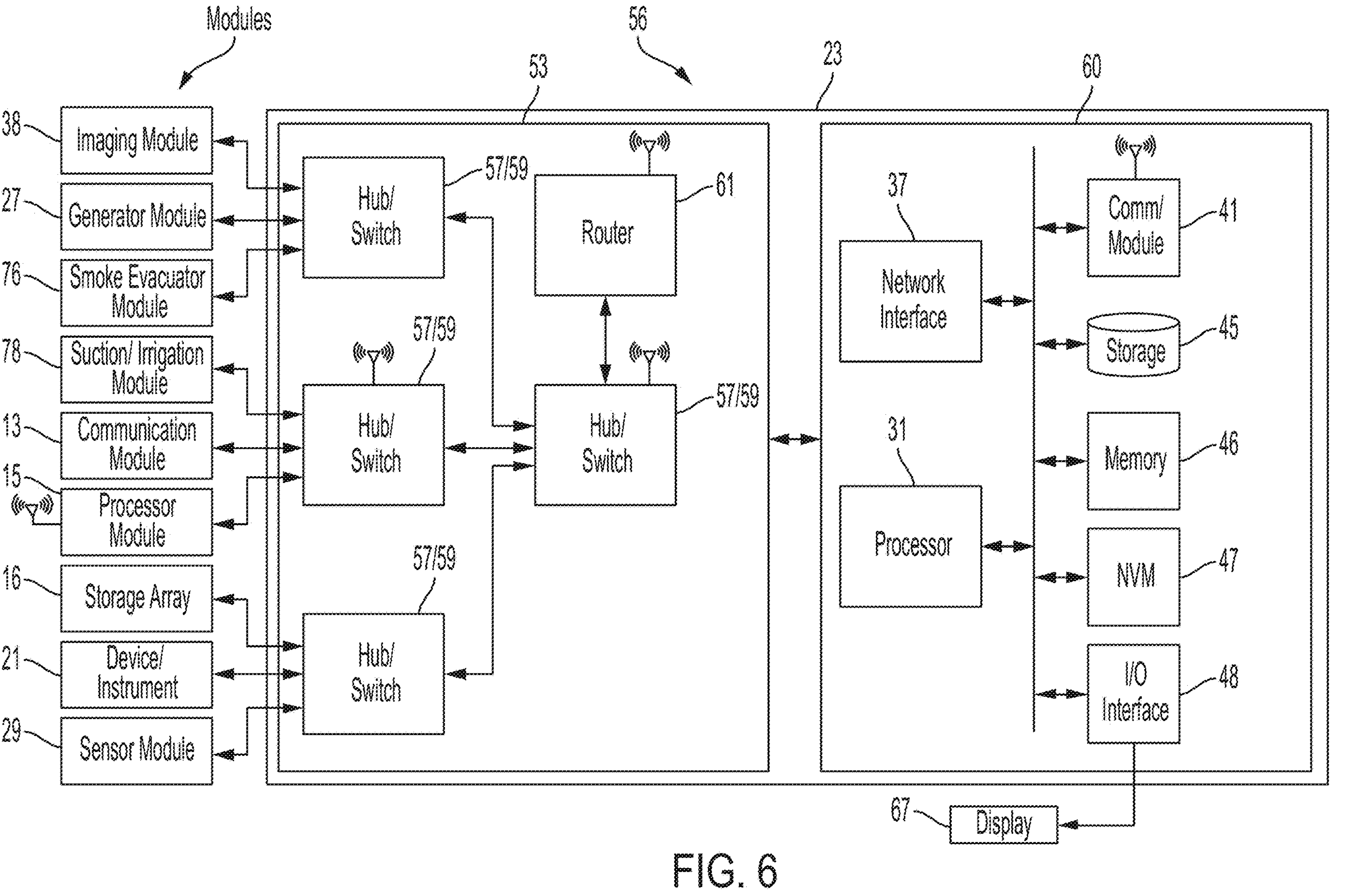
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics processing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

Figure 7:
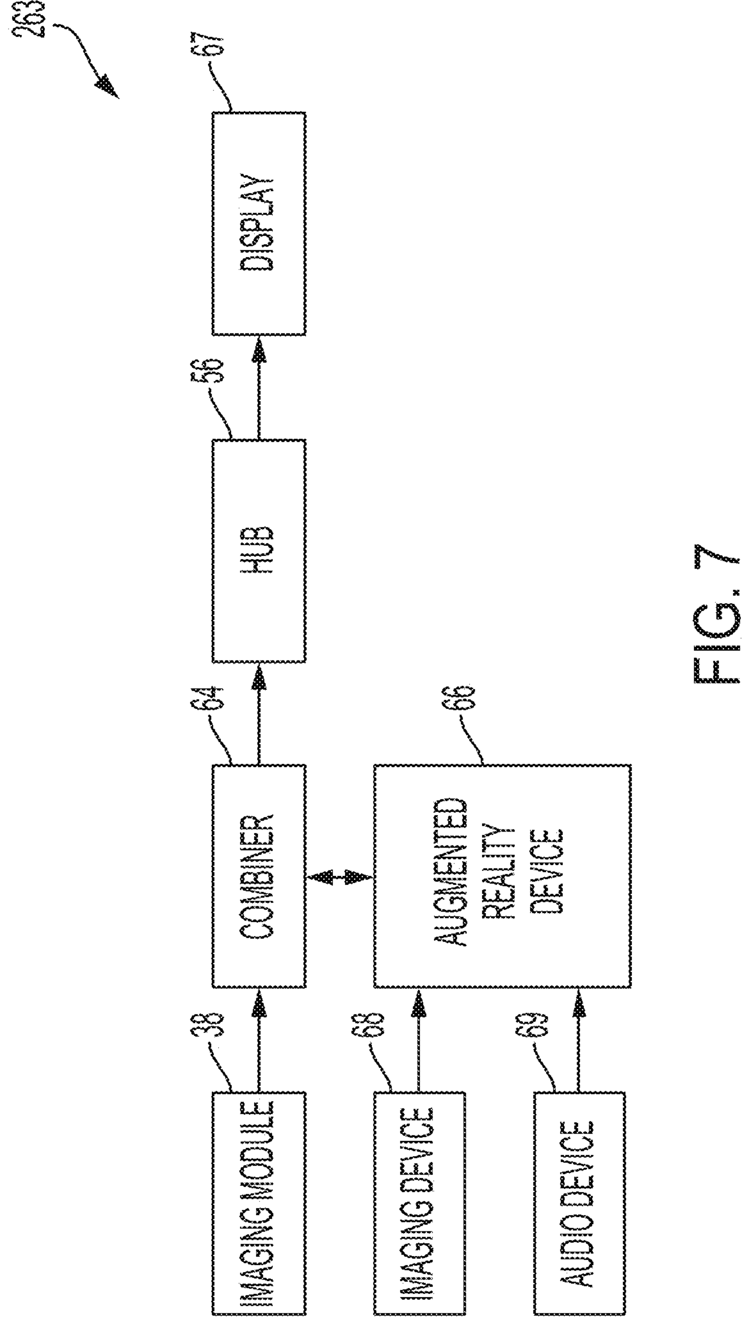
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality (AR) system 263 comprising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
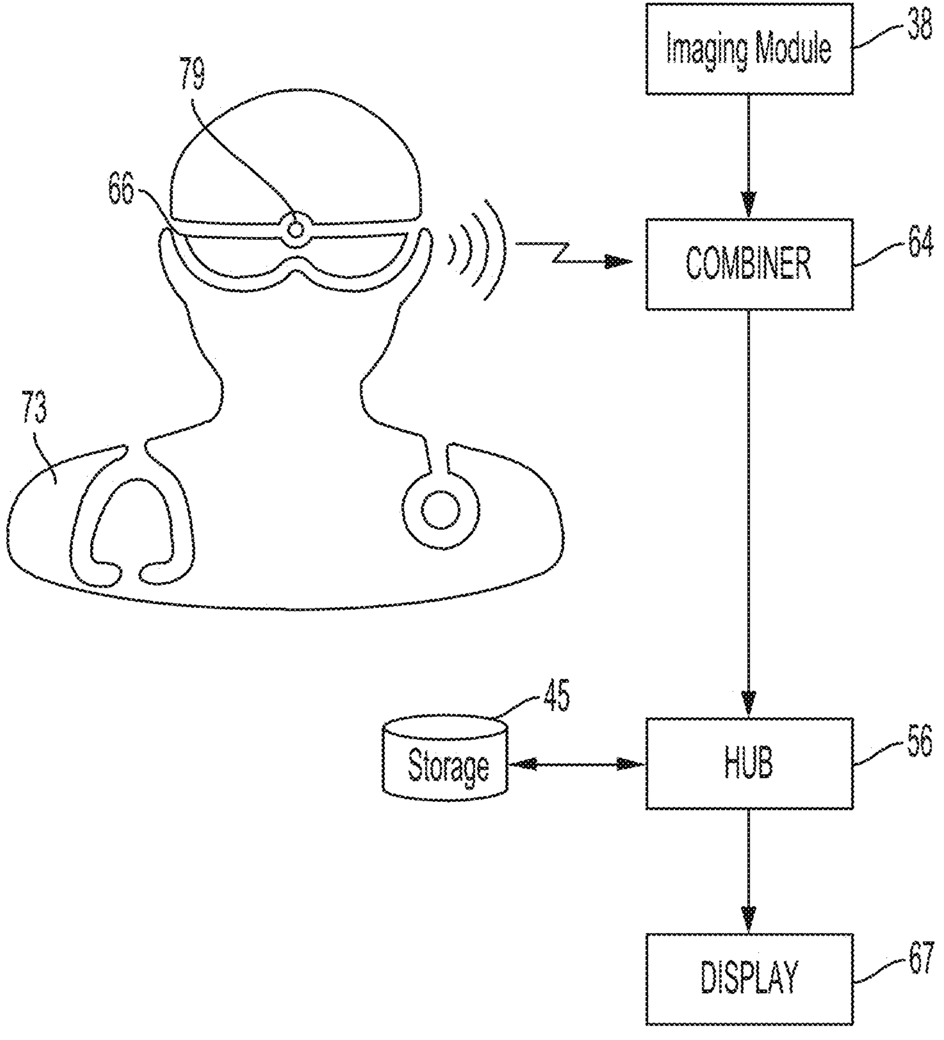
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure—ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
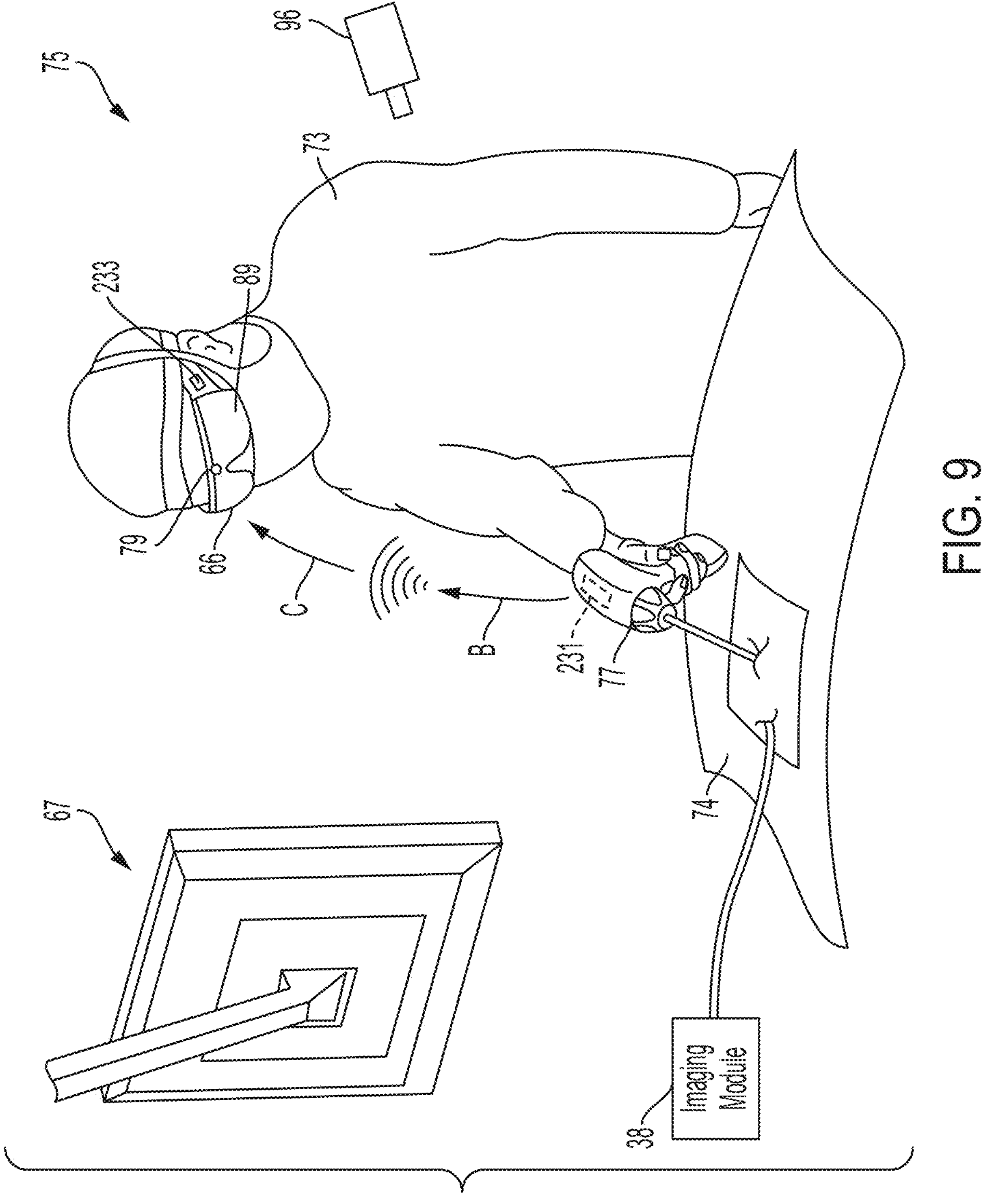
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see different virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the preoperative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 86, the patient data can also be utilized by a situationally aware surgical hub 5104 to generate control adjustments for the paired modular devices 5102.

Surgical displays (e.g. displays 7, 9, 19, 35, 62, 65, 66, 67, and 89) play an important function within the operating room, by provide useful information to a clinician (e.g. surgeon, surgical staff) that can used to, among other things, assess the progress of a surgical procedure, determine subsequent steps to take in the surgical procedure, monitor patent vital signs, etc. The displays need to be large enough such that this information being provided can be seen, yet not so large as to be overbearing and obstruct workflow or movement in a crowded operating room.

For example, an imaging device, such as one of the many imaging devices described elsewhere herein, is used to capture a livestream of a surgical field during a surgical procedure. A display shows this livestream captured by the imaging device such that the clinician can view the surgical field during the surgical procedure.

During the course of the surgical procedure, information that is relevant to or associated with the surgical procedure can be overlaid onto the livestream on the display. For example, an electrocardiogram (EKG) monitors a patient's heart rate during the surgical procedure and the monitored heart rate is overlaid on the livestream such that the clinician can ensure that the patient is stable.

Various other sensors, detectors, modules, etc. monitor other parameters over the course of the surgical procedure and information associated with these parameters can also be overlaid onto the display. However, some overlaid information may be of more significance than other overlaid information. As an example, when a clinician is manipulating tissue with an end effector of a surgical instrument, information regarding how much force is being applied to the tissue with the end effector is relevant to monitor so as to ensure the tissue isn't being unintentionally damaged.

However, owing the amount of information being overlaid on the display, more important information, such as a force being applied to the tissue, may be overlooked or missed by the clinician. This abundance of competing information can cause the surgeon to become overwhelmed with information that may be detrimental to their ability to adequately perform the surgical procedure, which can prove costly to the patient. Accordingly, there is a need to prioritize, control and/or limit the amount of data that is being overlaid on the display.

Figure 12:
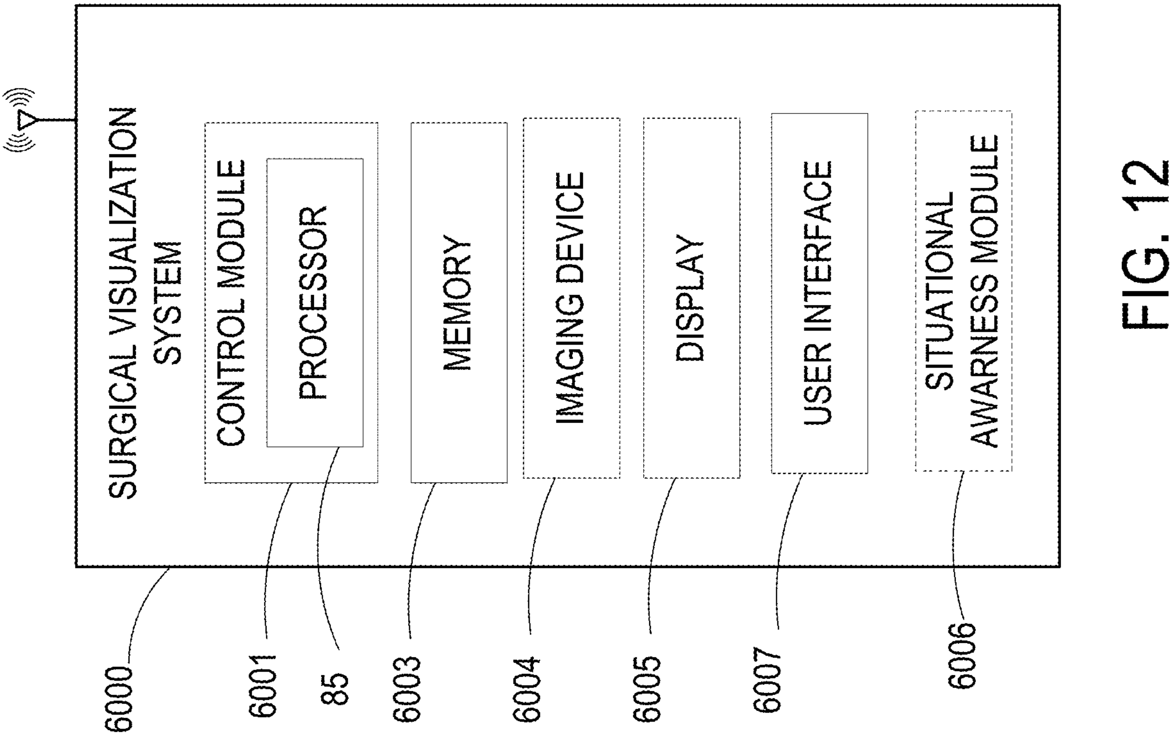
FIG. 12 illustrates a surgical visualization system, in accordance with at least one aspect of this disclosure.

FIG. 12 illustrates a surgical visualization system 6000, in accordance with at least one aspect of this disclosure. Various components of the surgical visualization system 6000 are similar in many respect to components of other systems described elsewhere in the present disclosure and, as such, are not repeated herein at the same level of detail for brevity. In some implementations the system 6000 is a standalone system. In other implementations, the system 6000 is integrated in, or used in conjunction with, the computer-implemented interactive surgical system 1.

The surgical visualization system 6000 includes a control module 6001 configured to perform various techniques described herein, for example, by using one or more processors or processing circuitry such as the processor 85. In some implementations, the system 6000 can include, be used in conjunction with, or be communication with the augmented reality device 84, for example. The system 6000 may further include storage medium such as, for example, a memory 6003, an imaging device 6004 such as, for example, the camera 88, and a display 6005. The system 6000 may further include one or more speakers 91, haptic controllers 92, and/or sensors 90 (see FIG. 10). The display 6005 can include, for example, the AR display 89, a VR display, a projector, a heads-up display, a screen, and/or any other suitable device for portraying visual content.

In some implementations, the system 6000 is incorporated into the computer-implemented interactive surgical system 50, for example. In some implementations the system 6000 is in operable communication with one or more hubs, systems, networks, servers, and/or databases that can deliver surgical data to the system 6000. For example, the system 6000 can be in operable communication with cloud 54 that may include a remote server 63, robot hub 72, surgical hub 56, devices/instruments 21, and/or modular control tower 23 via wired or wireless communication standards or protocols, as described herein. In some implementations, the system 6000 includes a situational awareness module 6006 similar to that described in connection was the surgical hub 5104. The situational awareness module 6006 can be trained to extrapolate contextual information about a surgical procedure based on a multitude of perioperative data received through sensor input and/or user input.

Figure 13:
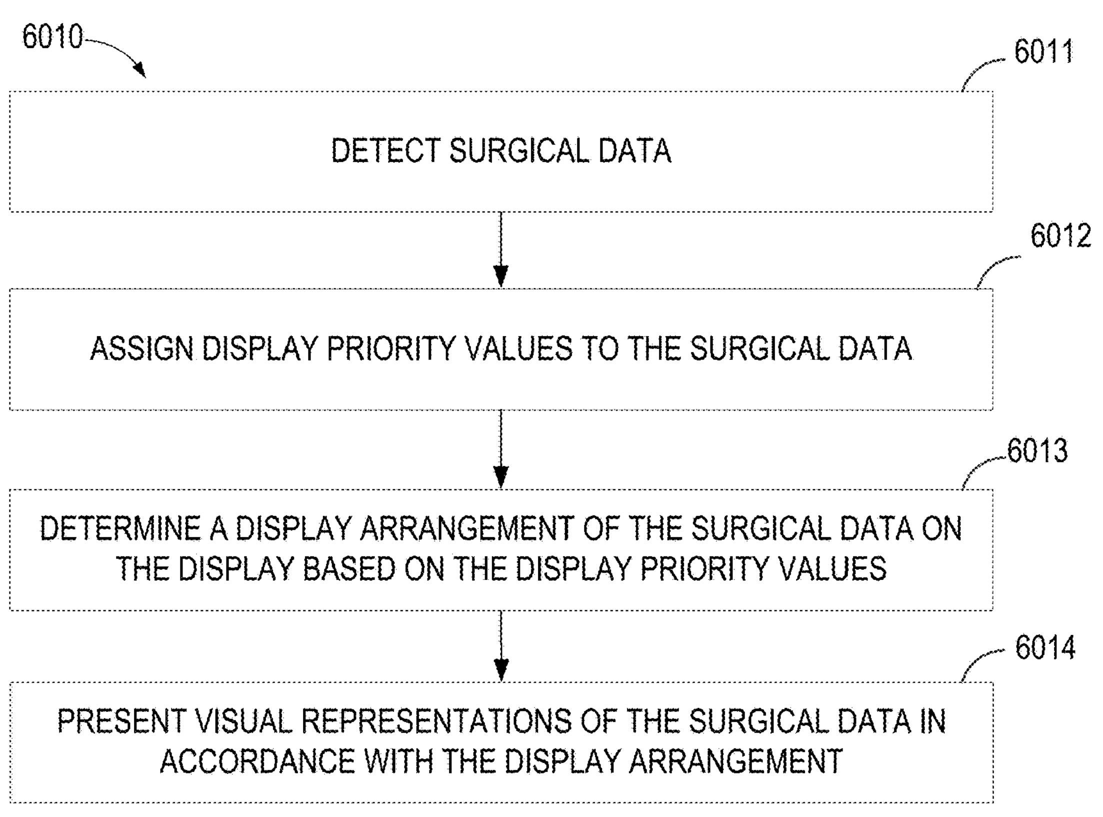
FIG. 13 is a flowchart showing operations of an example method for determining a display arrangement of surgical data competing for presentation onto a display, in accordance with at least one aspect of this disclosure.

FIG. 13 is a flowchart showing operations of an example method 6010 for determining a display arrangement of surgical data competing for presentation onto a display such as the display 6005. The method 6010 includes detecting 6011 surgical data, assigning 6012 display priority values, or display priority statuses, to the surgical data, and determining 6013 a display arrangement of the surgical data on the display based on the display priority values. The method 6010 may further include presenting 6014, by displaying, or overlaying onto the livestream of the surgical field, for example, visual representations of the surgical data in accordance with the display arrangement.

In some implementations, the surgical data is detected 6011 by the control module 6001. The surgical data can be detected 6011 by receiving the surgical data from one or more sources such as, for example, components of the computer-implemented interactive surgical system 1 via one or more wireless and/or wired communication interfaces. In at least one example, the surgical data may include data received from one or more of the surgical instrument 21. In another example, the surgical data includes contextual information ascertained by the situational awareness module 6006.

In certain exemplifications, the surgical data comprise control data, biomarker measurements, and/or other operational indicators of operations and/or outcomes associated with a surgical instrument 21. In certain exemplifications, the surgical data can be any data indicative of a higher propensity of malformed staples and poorly sealed tissue. In certain instances, the surgical data can be associated with tissue flow, clamping force, firing force, among other tissue and/or instrument parameters, which can be monitored and displayed to the clinician in multiple ways in real time to allow for adjustments to the firing process or to alert the surgeon of a potentially malformed staple region.

In some implementations, the display priority values are assigned based on the surgical data and/or contextual information regarding the surgical procedure developed by the situational awareness module 6006. In some implementations, the display priority values are assigned based on a triggering event, a condition, or a characteristic of the surgical data. In some implementations, assigning 6012 a display priority value includes changing a previously-assigned display priority value. For example, the detection of a triggering event, a condition, and/or a characteristic of the surgical data may cause a change in previously-assigned display priority value to a higher value or a lower value.

In certain exemplifications, the processor 85 employs a predetermined equation and/or formula in determining the display priority values of the surgical data. Various relevant factors can be considered and assigned different weights in calculating the display priority values. Additionally, or alternatively, one or more databases or tables listing surgical data and corresponding display priority values can be utilized by the processor 85 in assigning the display priority values.

In various implementations, the assigned 6012 display priority values comprise various levels of display priority such as, for example, a low display priority level, a medium display priority level, and/or a high display priority level. In some implementations, the display priority values are display priority statuses such as, for example, a high priority status, a neutral priority status, and/or a low priority status.

Figure 14:
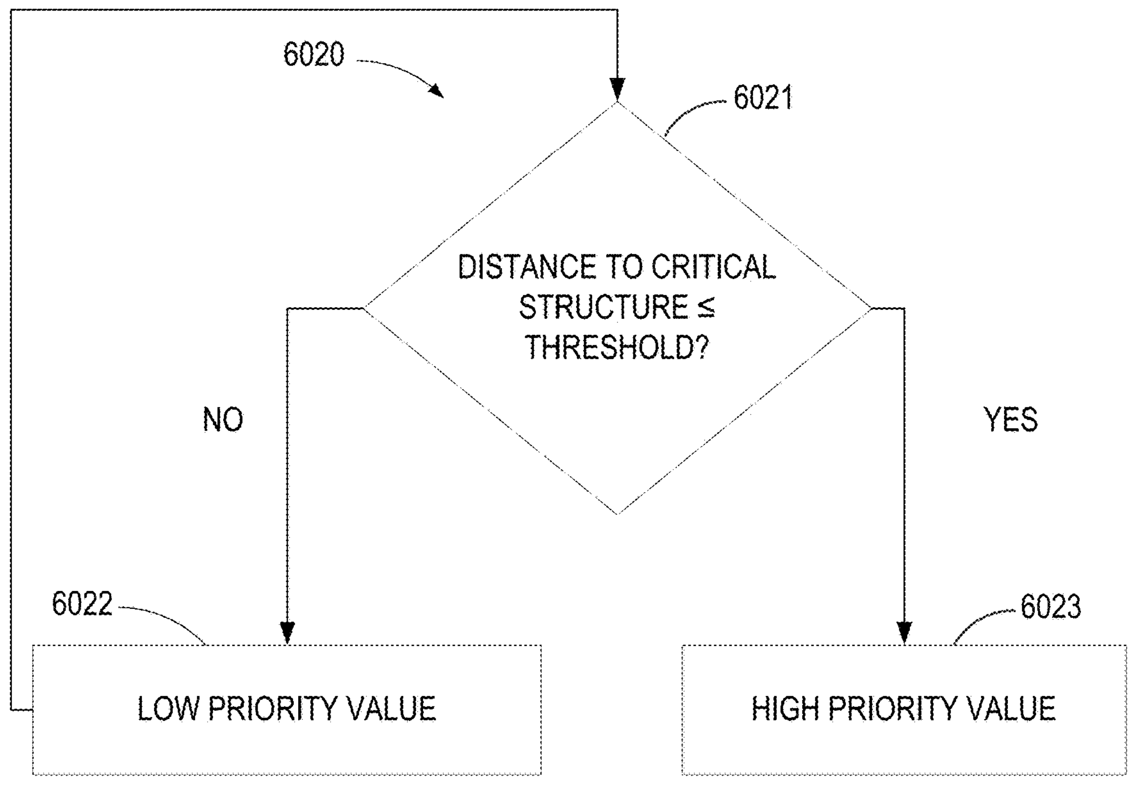
FIG. 14 is a flowchart showing operations of an example method 6020 for determining display priority values of the surgical data detected 6011, in accordance with the method of FIG. 13.

FIG. 14 is a flowchart showing operations of an example method 6020 for determining display priority values of the surgical data detected 6011, in accordance with the method 6010 of FIG. 13. In certain implementations, the display priority values depend on the surgical data. In the illustrated example, a display priority value is assigned based on proximity of a surgical instrument being utilized in the surgical procedure to a critical anatomical structure associated with the surgical procedure. The display priority value is based on a relationship between the received proximity data and a predetermined proximity threshold. For example, if 6021 the distance between the surgical instrument and the anatomical structure is greater than the predetermined threshold, the proximity data is assigned 6022 a low display-priority value. If 6021, however, the distance is less than or equal to the predetermined proximity threshold, the proximity data is assigned 6023 a high display-priority value.

In some implementations, the system 6000 employs the situational awareness module 6006 to identify the type of the surgical procedure to be performed. The type of surgical procedure can be determined from a user input, for example. Alternatively, or additionally, it can be determined from an inventory list of devices selected for use with the surgical procedure, which are unique to, or characteristic of, the surgical procedure type. The system 6000 may further identify a critical structure associated with the surgical procedure from a database and/or a user input, for example. In some implementations, the system 6000 can detect the critical structure in a livestream of the surgical field as captured by the imaging device. Moreover, the system 6000 may further detect a surgical instrument 21 in the surgical field, and may track proximity of the surgical instrument 21 to the critical structure. A display priority value of the proximity data can be determined, as discussed in connection with FIG. 14.

In some implementations, identification of the critical structure and/or the surgical instrument in the livestream of the surgical field can be attained through various suitable object recognition, object tracking, object labeling, and/or other image processing techniques such as one discussed in U.S. patent application Ser. No. 16/729,807, titled STRUCTURED MULTI SPECTRAL COMPUTATIONAL ANALYSIS, which is incorporated by reference in its entirety. For example, previously-stored images of the surgical instruments and/or the critical structure can be utilized to identify surgical instruments and/or critical structures in the surgical field.

A low anterior resection (LAR) surgical procedure is a common surgery for rectal cancer. This procedure involves the removal of the rectum. The colon is then attached to the remaining section of the rectum to allow for normal bowel movement. A circular stapler is generally used in a low LAR procedure. Initially, as the surgeon begins to set up the structures to create the anastomosis, certain parameters such as parameters of tissue tension and anastomosis tissue pressure are not relevant, and can be distracting if overlaid or emphasized too soon on the livestream. In certain instances, to avoid the distraction and/or reduction of the display space available for the livestream, such parameters are overlaid and/or emphasized onto the display 6005 per a display arrangement in accordance with the method 6010.

In some implementations, display priority values are assigned to the parameters of tissue tension and anastomosis tissue pressure based on a triggering event associated with the relevance of the parameters to the surgical procedure. The triggering event can, for example, be the detection of a connection of the anvil of the circular stapler to the circular stapler trocar. The detection can be achieved automatically by employing one or more object recognition, object tracking, object labeling, and/or other image processing algorithms of the livestream and/or through one or more sensors in the anvil and/or the trocar that are triggered by the connection or the proximity of the anvil to the trocar, for example.

In some implementations the triggering event is associated with an increased criticality or risk level. In certain instances, the triggering event can yield a warning and/or an immediate pausing of a surgical activity such as, for example, pausing the staple firing of a surgical instrument 21. The triggering event can yield a transition to a pending failure mode, for example, where a series of instructions are provided to remedy, or reduce, the cause of the failure. As described below in greater detail, the triggering event can be, for example, a buttress plowing, tissue cutting without tissue sealing, and/or broken anvil. In some implementations, these triggering events are visually detected automatically through object recognition, object tracking, object labeling, and/or other suitable image processing techniques of image frames of the livestream, for example, or through various suitable wired and/or wireless communication schemes.

In some implementations, the failure mode is caused by buttress plowing, a condition that may occur where a buttress is utilized in a tissue stapling by a surgical instrument 21. In response to detecting the buttress plowing, the control module 6001, for example, causes the surgical instrument 21 to stop a firing sequence of the surgical instrument. For example, the control module 6001 may communicate a firing-stop command to the surgical instrument 21 through a wireless, or wired, interface. Additionally, the control module 6001 may cause a warning, and/or a series of instructions that remedy the failure by applying tension to tissue during firing, for example, to be displayed, or overlaid onto a livestream of the surgical field.

Alternatively, the failure can be caused by detecting tissue cutting without tissue sealing. For example, the control module 6001 may detect a failure of staples to be deployed into tissue grasped by an end effector of the surgical instrument 21, as a cutting member of the surgical instrument 21 is advanced, which leads to a tissue cutting without tissue sealing failure. In response to detecting the failure, the control module 6001 may cause a warning, and/or a series of instructions that remedy the failure, to be displayed, or overlaid onto a livestream of the surgical field. The instructions may suggest clamping surrounding blood supply, preparing a material to stop bleeding before releasing the tissue from the jaws of the end effector of the surgical instrument 21.

Figures 15, 16:
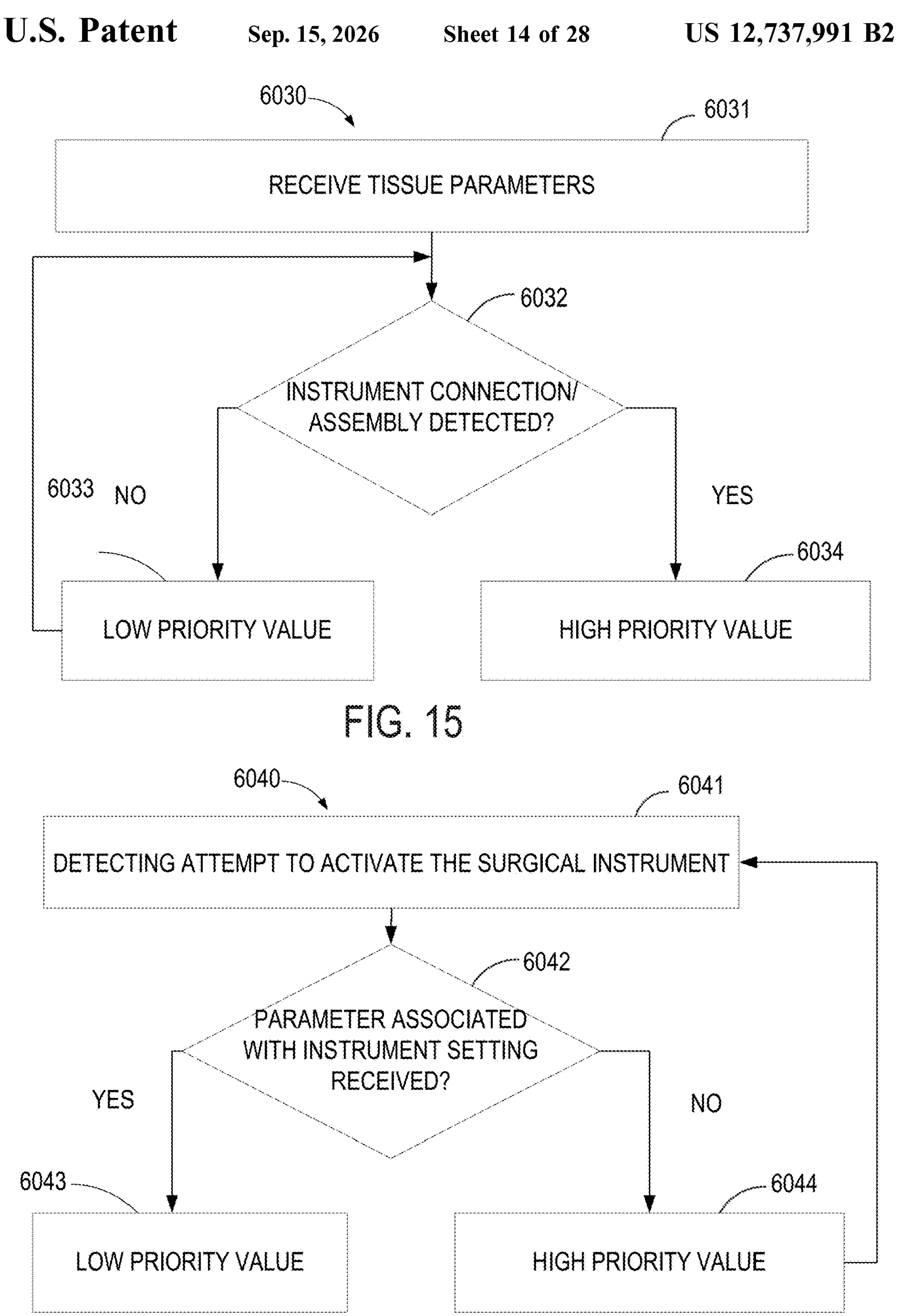
FIG. 15 is a flowchart showing operations of a method for determining display priority values of tissue tension and/or pressure parameters within a surgical anastomosis, in accordance with at least one aspect of this disclosure.
FIG. 16 is a flowchart showing operations of a method for determining display priority values based on a triggering event, in accordance with at least one aspect of this disclosure.

FIG. 15 is a flowchart showing operations of an example method 6030 for determining display priority values of tissue tension and/or pressure parameters within a surgical anastomosis. The method 6030 includes receiving 6031 the tissue parameters and assigning display priority values to the parameters based on a triggering event such as the detection of a connection between the anvil and the trocar of the circular stapler. For example, if 6032 the trocar-anvil connection is not detected, a low display-priority value is assigned 6033 to the parameters. If 6032, however, the trocar-anvil connection is not detected, a high display-priority value is assigned 6034 to the parameters.

While the method 6030 provides an example that utilizes detection of the connection of components of a circular staple as a triggering event for determining display priority values, the connection of other components of other instruments 21 can be utilized as triggering events for determining display priority values. For example, the attachments of a cartridge reload, an end effector, and/or a shaft can represent a triggering event for determining display priority values. In some implementations, the assembly of surgical instrument components, surgical robotic components, and/or any suitable surgical systems can be utilized as triggering events for determining display priority values.

FIG. 16 is a flowchart showing operations of an example method 6040 for determining display priority values based on a triggering event. In the illustrated example, the triggering event is an activation of a surgical instrument 21 prior to receiving a parameter needed to perform an adjustment of a setting of the surgical instrument 21 for optimal operation thereof. In some implementations, the system 6000 can be configured to detect the surgical instrument 21 in the livestream of the surgical field, and await a user input of the required parameter.

In some implementations, the parameter can be a required user input. The parameter can be associated with a tissue characteristic or a disease state. Certain device settings can be adjusted, prior to utilizing the device to treat a tissue, based on the condition of the tissue and/or a disease state. These adjustments may include lowering a firing speed for a surgical stapling instrument to better ensure a seal. For surgical energy device, the surgeon may adjust the power in response to the new tissue characteristics, for example, to provide a better seal of the tissue.

As illustrated in FIG. 16, the method 6040 includes detecting 6041 an attempt by the user to activate the surgical instrument 21. If 6042 the needed parameter is received, a low display-priority value is assigned 6043. If 6042, however, the trocar-anvil connection is not detected, a high display-priority value is assigned 6044 to the parameters.

In some implementations, the parameter is a sensor parameter, which can be an internal sensor of the surgical instrument 21, or any other sensor, configured to measure a parameter needed for proper operation of the surgical procedure. The detection of a triggering event, such as activation of the surgical instrument 21 prior to receiving the parameter, may cause the system 6000 to assign a high priority value to visual content, for example in the form of an overlay, requesting a permission to ignore, or proceed without, the missing parameter, or requesting entry of the missing parameter, for example.

In some implementations, the triggering event is a sensor parameter that deviates from an acceptable predetermined range or threshold. The sensor parameter can be a tissue impedance parameter measureable by a surgical instrument grasping tissue in the surgical field, for example by performing impedance spectroscopy. If the grasped tissue is highly saturated with saline, the measured tissue impedance will deviate from an acceptable predetermined range or threshold, triggering the system 6000 to assign a high display-priority value to a warning regarding the detected deviation, a user override request and/or a user override request.

In some implementations, the triggering event can be a detection of a mismatch between a selected surgical instrument 21 and the surgical procedure to be performed by the surgical instrument 21. The mismatch can be detected by the system 6000 and/or the computer-implemented interactive surgical system 1, for example. The type of the surgical procedure and an inventory list of surgical instruments 21 to be utilized in the surgical procedure can be entered through a user interface and/or can be detected through object recognition, object tracking, object labeling, and/or other suitable image processing techniques of image frames of the livestream, for example, or through various suitable wired and/or wireless communication schemes. The situational awareness module 6006 may compare the inventory list detected or entered by the user to a previously-stored inventory list that is historically associated with the surgical procedure type detected or entered by the user. The detection of a mismatch causes the system 6000 to assign a high display-priority value to a warning regarding the mismatch, a user override request, and/or a confirmation request.

In at least one example, detecting the selection of a circular stapler for use in a hysterectomy causes the system 6000 to assign a high display-priority value to a warning regarding the mismatch, a user override request, and/or a confirmation request. The system 6000 may require the staff to confirm the need for the circular stapler or to eliminate it from the current active list or correct the procedural plan mismatch.

In some implementations, the triggering event can be the detection of incompatible components of a surgical instrument assembly. Various surgical instruments 21 utilize interchangeable components such as, for example, interchangeable cartridges, reloads, end effectors, shafts, handles, motors, and/or batteries. Utilizing incompatible components may cause the surgical instrument 21 to function improperly, which may cause harm to the patient and/or interfere with the surgical procedure outcome. They system 6000 may assign display priority values based on the detection of incompatible components.

The computer-implemented interactive surgical system 1 can detect incompatible components through authenticity checks or integrity checks. Unsuccessful authenticity and/or integrity validations can indicate incompatible components. In certain implementations, various components are equipped with sensors that can detect a proper connection indicating a proper compatibility between connected components. In such implementations, sensor signals, or the lack thereof, can indicate incompatible components.

In at least one example, upon installation of an interchangeable component in a surgical instrument 21, the surgical instrument 21 may interrogate the interchangeable component for identification information that can be compared to recognized identification information stored in a database, for example. The database can be kept on a storage medium of the surgical instrument 21, a hub 22, and/or the remote server 13 of the cloud-based system 4, for example. Failure to authenticate the identification information causes the system 6000 to assign a high display-priority value to a warning regarding the incompatible components, a user override request, and/or a confirmation request. The computer-implemented interactive surgical system 1 may also inhibit certain capabilities of the surgical instrument 21, or lockout the surgical instrument 21, to protect the patient and/or the surgical procedure outcome.

In some implementations, the triggering event is a detection of a tissue condition such as a biological anomaly that can negatively affect a proper use of a surgical instrument 21 in the surgical procedure under standard settings. For example, an extremely high Body Mass Index “BMI” necessitates adjustments to various settings of surgical instruments 21 in a sleeve gastrectomy. The BMI level can be detected by the situational awareness module 6006, for example, from perioperative data.

Detection of a BMI level that deviates from an acceptable predetermined threshold may cause the system 6000 to assign a high display-priority value to a warning regarding the BMI level, a user override request, and/or a confirmation request. Moreover, the system 6000 may further assign a high display-priority value to a recommended surgical instrument setting such as, for example, a lower firing speed of a surgical stapler utilized in the sleeve gastrectomy. The system 6000 and/or the computer-implemented interactive surgical system 1 can be configured to automatically determine the recommended surgical instrument setting based on perioperative data.

In various aspects, determining 6013 a display arrangement of the surgical data on the display 6005 includes changing a characteristic of a visual representation of the surgical data. In some implementations, the surgical data can be in the form of a sensor reading that can be overlaid onto the livestream of the surgical field on the display 6005. The sensor reading can be highlighted in a color that changes in accordance with the significance of the sensor parameter reading to the surgical procedure. In some implementations, the sensor reading can be visually represented in a first color, while the sensor reading is within normal bounds of a predetermined standard, and the sensor reading can be visually represented in the second color, different from the first color, while the sensor reading is outside the normal bounds.

For example, the sensor reading can be a temperature reading that can be visually represented in a green color while the temperature reading is less than, or equal, to a predetermined temperature threshold. If the temperature reading exceeds the predetermined threshold, the temperature reading can then be visually represented in a yellow, or red, color, for example, indicative of the significance of the current temperature to the surgical procedure.

In some implementations, the change in the characteristic of the visual representation of the surgical data can be a gradual transition. For example, the temperature reading can be gradually transitioned from yellow to red as the temperature rises to reflect the severity of the change in the temperature. In some implementations, other characteristics of the visual representation can also be changed such as, for example, size, shape, display time, display location, display three dimensional arrangement (e.g. foreground, background), display blinking, highlighting, and/or font.

In various aspects, determining 6013 a display arrangement of the surgical data on the display 6005 includes removing, or changing, a characteristic of the visual representation of the surgical data in a manner that reflects a reduction in significance and/or an inactive status, for example. In some implementations, the surgical data comprises a temperature of a surgical energy device utilized to seal tissue in the surgical field of a surgical procedure. In response to activation of the surgical energy device, a visual representation of the temperature is overlaid onto the livestream of the surgical field on the display 6005. The visual representation signifies that the surgical energy device is “hot”, in an effort to provide a warning for careful handling of the surgical energy device while in the active status. In some implementations, the visual representation may comprise a characteristic indicative of a high-priority status to ensure grabbing the attention of a clinician using the surgical energy device and/or other OR staff.

As the clinician uses the surgical energy device, the visual representation of the temperature may be assigned a lower-priority status, even though the surgical energy device continues to be hot. This is in order to reduce distraction to the clinician and/or shift the clinician’s attention to another visual representation of higher-priority surgical data. For example, the visual representation of the temperature can be changed to a neutral color, reduced in size, and/or changed into a different shape.

Once the surgical energy device is inactive, if the temperature is at, or exceeds, a predetermined threshold, a high-priority status is reassigned to the temperature causing its visual representation to change providing a warning to draw attention or highlight that even inactive the surgical energy device is still above a temperature threshold that could cause injury. In response to the temperature dropping below the predetermined threshold, the visual representation of the temperature is changed again to a lower-priority status. In some implementations, the temperature of the surgical energy device can be monitored using one or more temperature sensors on, or near, an end effector of the surgical energy device. The sensor readings can be communicated wirelessly, or through a wired communication, to the system 6000.

In various aspects, determining 6013 a display arrangement of the surgical data includes transferring a visual representation of the surgical data between a first display and a second display. The transfer permits the system 6000 to timely present surgical data to an appropriate user at an appropriate time and location. In some implementations, the first display is a set-up display, nurse display, or preparation display, and the second display is a surgical field or surgeon display such as, for example, a display 6005. In such implementations, the transfer can be triggered by a detection of the completion of the setup. In certain instances, a user input can indicate the completion of the setup, which triggers the transfer. The setup may include checking surgical devices against an inventory list to ensure presence of the surgical devices necessary to perform the surgical procedure. The setup may further include testing the surgical devices to ensure successful wireless communication operation, and/or any other suitable testing.

In some implementations, the control module 6001 is configured to assign a high display-priority value to the surgical data at the first display and a low display-priority value to the same surgical data at the second display until the detection of a triggering event. In response to the detection, the control module 6001 is configured to assign a low display-priority value to the surgical data at the first display and a high display-priority value to the same surgical data at the second display. The switching of priorities causes the surgical data to be transferred to the second display. In some implementations, the switching causes a visual representation of the surgical data to be dimmed out at the first display, and to appear at the second display. Then, after a predetermined time period has passed, the visual representation of the surgical data can be completely removed from the first display.

Figure 17:
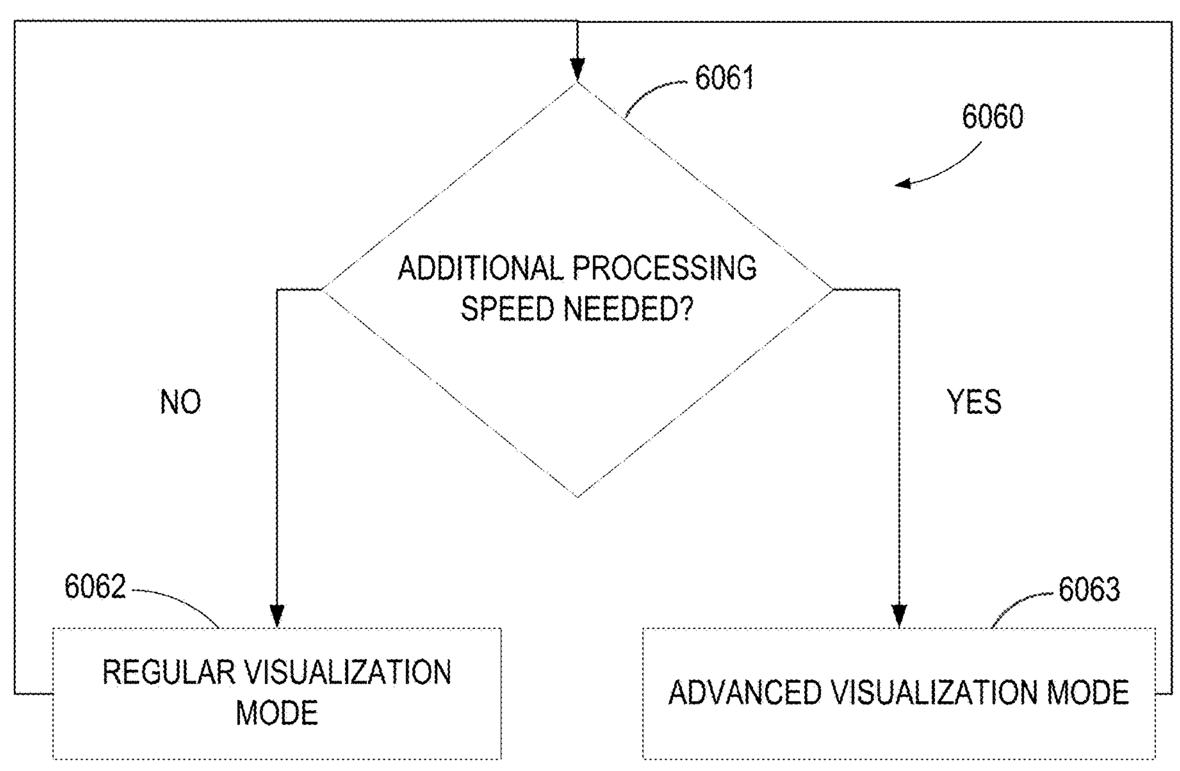
FIG. 17 is a flowchart showing operations of a method, in accordance with at least one aspect of this disclosure.

In various aspects, a determined 6013 display arrangement may require additional processing capabilities such as, for example, one that involves developing a spectral view and/or tacking a surgical end effector in the surgical field and overlaying surgical data on the surgical end effector. FIG. 17 is a flowchart showing operations of an example method 60600 for responding to a need for additional processing speed during a surgical procedure performed by the computer-implemented interactive surgical system 1. In instances where additional processing capabilities are needed 6061, the control module 6001 may utilize a field programmable gate array (FPGA). Additional high speed calculations for key variables can be assigned to the FPGA in an advanced visualization mode 6063, for example, as illustrated in a method 6060 in FIG. 17. When the advanced visualization mode 6063 is enabled, the FPGA is dynamically re-purposed to maximize visualization (e.g. spectral) processing capabilities. After completion of the high speed calculations, the FPGA can be returned to normal operation, in a regular visualization mode 6062.

In some implementations, a transfer between the regular visualization mode 6062 and the advanced visualization mode 6063 can be triggered by the surgical task. The control module 6001 may detect an upcoming, or current, surgical task based on contextual information generated by the situation awareness module 6006. The control module 6001 may consult a database, which can be stored in the memory 6003, for the visualization mode associated with the surgical task. If the surgical task requires an advanced visualization mode 6063, the control module 6001 repurposes the FPGA to aid in the high speed calculations associated with the advanced visualization mode 6063. When the surgical task is completed, the control module 6001 then triggers a return to the regular visualization mode 6062, effectively switching the FPGA to performing regular tasks.

In certain implementations, detecting 6011 the surgical data includes receiving two separate surgical data competing for a user's attention. For example, detecting 6011 the surgical data can include receiving a first surgical data and a second surgical data, wherein the first surgical data and the second surgical data are both relevant to the current surgical task and/or are associated with one, or more, active surgical devices. In such implementations, the method 6010 can include assigning 6012 display priority values to the first surgical data and second surgical data based on their comparative criticality to the success of the surgical and/or severity of failures that can be caused by ignoring them. For example, if the first surgical data comprises a higher criticality than the second surgical data, the method 6010 assigns 6012 a higher display-priority value to the first surgical data than the second surgical data. Additionally, or alternatively, if a first failure associated with the first surgical data is more severe than a second failure associate with the second surgical data, the method 6010 assigns 6012 assigns a higher display-priority value to the first surgical data than the second surgical data.

In some implementations, display priority values and corresponding criticalities and/or failure severities associated with various surgical data can be stored in any suitable format, e.g. a table or a database, in a storage medium such as the memory 6003. The processor 85 of the control module 6001 can be configured to assign 6012 display priority values based on such stored information.

Additionally, or alternatively, display priority values can be assigned 6012 based on predetermined user preferences and/or user-specific surgical context. In some implementations, surgical data associated with an active surgical instrument 21 can be selectively displayed onto a display associated with a clinician using the surgical instrument 21. Accordingly, the method 6010 may include assigning 6012 different display priority values to the same surgical data for different displays.

In one exemplification, a surgical data associated with a first surgical device, being utilized by a clinician, is simultaneously assigned 6012 a high display-priority value with respect to a first display selected by, or otherwise associated with, the clinician, and a low display-priority value with respect to other displays not selected by, or associated with, the clinician. In another exemplification, a first surgical data associated with a first surgical device, being utilized by a clinician, is assigned a high display-priority value with respect to a first display selected by, or otherwise associated with, the clinician, while a second surgical data associated with a second surgical device, not being utilized by the clinician, is assigned a low display-priority value with respect to the first display.

In various instances, the control module 6001 receives contextual information from the situational awareness module 6006 that can be utilized in the aforementioned pairing of surgical data of a particular surgical device with a display associated with a clinician using the surgical device. The contextual information can be generated by the situational awareness module 6006 based on perioperative data.

In some implementations, a database or table may store the pairing information. In other instances, the clinician may wear a unique identifier that can be detected by the surgical device when the clinician holds the surgical device. When a positive identification is made, the control module 6001 can then assign high display-priority values to surgical data associated with the surgical device with respect to a display selected, or otherwise associated, with the clinician. In one exemplification the unique identifier can be an RFID in the clinician's glove, which is detected by a corresponding RFID scanner in the handle of the surgical device.

In certain instances, such as during a colorectal procedure, the system 6000 is configured to automatically switch a display (e.g. display 6005) from showing a first livestream of a first surgical field to a second livestream of a second surgical field. The automatic switching can be triggered by the completion of a surgical task in a surgical procedure. In one example, a predetermined surgical cue, indicative of the completion of the surgical task, can be utilized as a trigger for the automatic switching between the livestreams. The predetermined surgical cue may include, for example, detecting a completion of a staple firing into tissue by a surgical instrument 21, detecting a completion of a tissue sealing by a surgical instrument 21, and/or detecting the release of a tissue from the jaws of an end effector of a surgical instrument 21, for example by opening the jaws.

The predetermined surgical cue may also include detecting an activation of a surgical instrument 21 followed by a deactivation of the surgical instrument 21, which indicates completion of a surgical task by the surgical instrument 21. In some implementations, the control module 6001 leverages readings from one or more sensors of the surgical instruments 21 and/or other components of the computer-implemented interactive surgical system 1 to detect the predetermined surgical cue. In some exemplifications, predetermined surgical cue is detected based on contextual information generated by the situational awareness module 6006.

In a colorectal procedure a clinician uses a circular stapler and a liner stapler to complete various tasks of the procedure. The colorectal procedure involves operating at two discrete surgical fields, an internal surgical field where diseased tissue is excised and an external surgical field where the circular stapler is utilized. In some implementations, the first livestream focuses on the internal section where tissue excision is taking place, and the second livestream focuses on the external section where the circular stapler is applied. In such implementations, the automatic switching can be triggered by completion of the tissue excision by the linear stapler, which can be detected by deactivation of linear stapler and/or removal of the linear stapler from the first surgical field, for example. The control module 6001 may employ various object recognition, object tracking, and/or object labeling algorithms, and/or other image processing techniques of image frames of the livestream, for example, to detect removal of the linear stapler from the surgical field.

Figure 18:
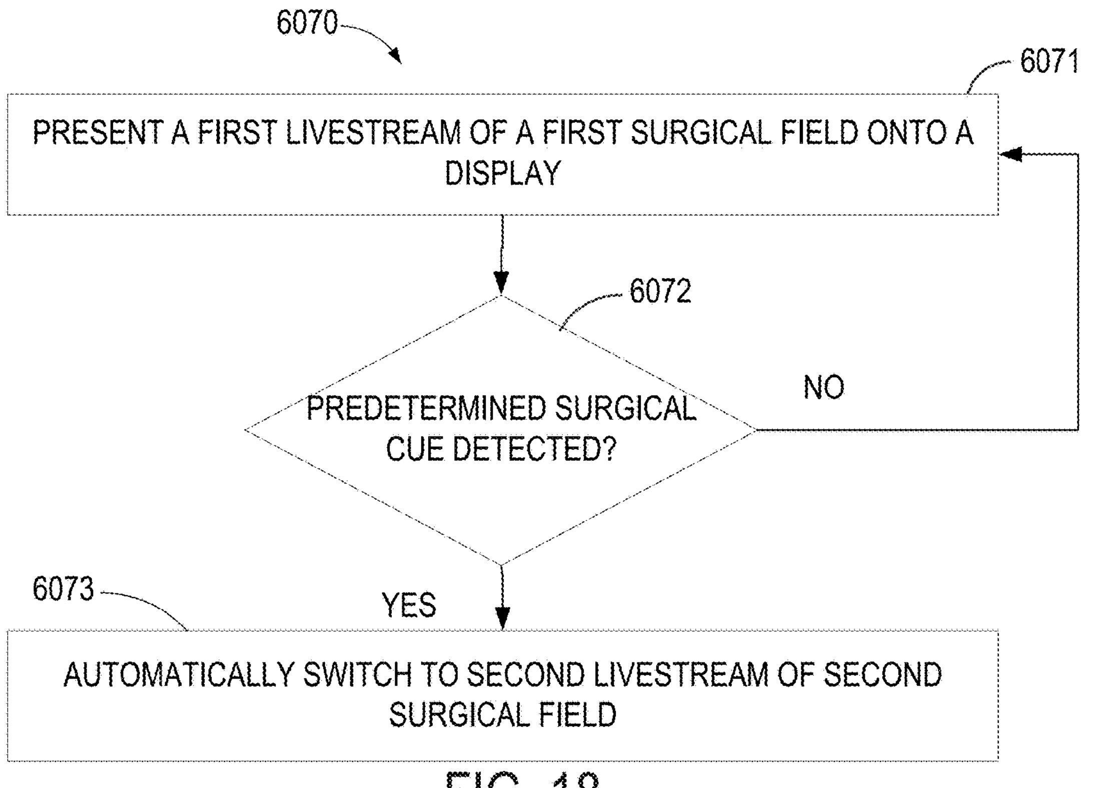
FIG. 18 is a flowchart showing operations of a method for automatic switching between livestreams of surgical fields in a surgical procedure, in accordance with at least one aspect of this disclosure.

FIG. 18 is a flowchart showing operations of an example method 6070 for automatic switching between livestreams of surgical fields in a surgical procedure. In some implementations, the method 6070 can be executed by the computer-implemented interactive surgical system 1, for example. The method 6070 includes presenting 6071 a first livestream of a first surgical field onto a display (e.g. display 6005). If 6072 a predetermined surgical cue, indicative of completion of a surgical task at the first surgical field is detected, automatically switch 6073 from presenting the first livestream of the first surgical field onto the display to presenting a second livestream of the second surgical field onto the display. In some exemplifications, the second surgical field is associated with a second surgical task that follows the first surgical task in the surgical procedure.

During a surgical procedure, various components of the computer-implemented interactive surgical system 1 may compete for available system resources such as power, current, and/or processing resources. Additionally, or alternatively, the operation of certain components of the computer-implemented interactive surgical system 1 may interfere with, or negatively affect, the operation of other components of the computer-implemented interactive surgical system 1. Various methods and systems are described herein to ensure the components function successfully by maintaining a balance in system resources and/or components operations.

Figure 19:
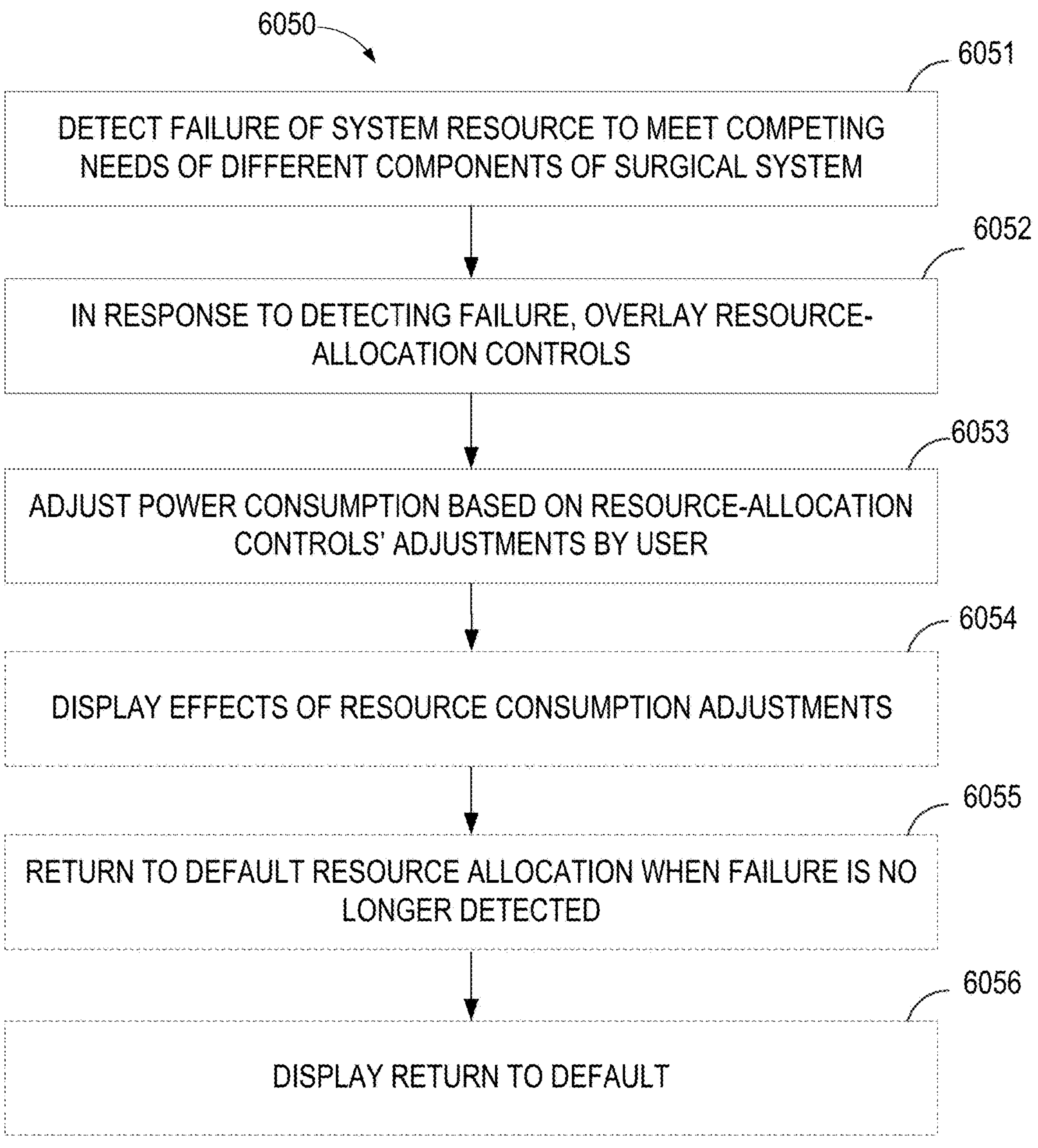
FIG. 19 is a flowchart showing operations of a method for balancing system resources during a surgical procedure, in accordance with at least one aspect of the present disclosure.

FIG. 19 is a flowchart showing operations of an example method 6050 for balancing system resources during a surgical procedure performed by the computer-implemented interactive surgical system 1. The method 6050 includes detecting 6051 a failure of a system resource to meet competing needs of different components of the computer-implemented interactive surgical system 1. The method 6050 further includes displaying resource-allocation controls of the system resource, in response to detecting the failure, for example by overlaying 6052 the resource-allocation controls on a livestream of a surgical field of the surgical procedure. Additionally, the method 6050 may further include displaying recommended adjustments to the resource-allocation controls.

Further to the above, the method 6050 includes adjusting 6053 power consumption of one or more of the different components based on resource-allocation controls' adjustments by the user. The method 6050 may further include returning 6055 to a default resource allocation, or removing resource consumption restrictions, when the failure is no longer detected. The method 6050 may further include displaying 6054 visual content representative of the effects of the adjustments to resource allocations and/or displaying 6056 visual content representative of a return to a default mode, for example by overlaying the visual contents onto a livestream of a surgical field on a display of the computer-implemented interactive surgical system 1.

In some implementations, detecting 6051 the failure includes reaching and/or exceeding a predetermined threshold such as, for example, a power threshold, a current threshold, a processing threshold, and/or a maximum utilization threshold. The predetermined threshold can be selected to ensure that detecting 6051 the failure is achieved prior to reaching a point where power consumption is beyond available power resources to avoid malfunctions during the surgical procedure. In some implementations, the predetermined threshold is stored in a storage medium such as the memory 6003, which is accessed by the processor 85 and compared to a monitored value (e.g. total consumption, consumption rate).

In some implementations, the failure is detected 6051 when the control module 6001 detects competing tasks being performed during a surgical procedure with a total estimated resource consumption (e.g. power consumption) or a resource consumption rate at, or greater than, the predetermined threshold. In some implementations, the failure is detected 6051 when the control module 6001 detects a simultaneous utilization of multiple components of the computer-implemented interactive surgical system 1 with a total estimated resource consumption (e.g. power consumption) or a resource consumption rate at, or greater than, the predetermined threshold. In one example, a database, stored for example in the memory 6003, may include a listing of resource consumption estimates associated with various components of the computer-implemented interactive surgical system 1 and/or various tasks performed by the computer-implemented interactive surgical system 1. The processor 85 may calculate a resource consumption value based on the information in the database, and compare the calculated value to the predetermine threshold for the purpose of determining whether the failure is detected 6051.

In some implementations, the system resource is power and the components of the computer-implemented interactive surgical system 1 competing for the power resource are the system 6000, or any other visualization system of the computer-implemented interactive surgical system 1, and the generator 27. During a surgical tissue sealing procedure, for example, the computer-implemented interactive surgical system 1 can be configured to perform two tasks that collectively require a power consumption that reaches, or exceeds, the predetermined threshold. The first task can be a visualization task, e.g. providing a spectral view, of the surgical field, and the second task can be energizing a surgical energy device to seal tissue grasped by the surgical energy device in the surgical field, for example. The generator module 27 can be configured to power the surgical energy device to seal the tissue by application of therapeutic energy to the tissue.

In such implementations, the failure is detected 6051 by monitoring power consumption by the system 6000 and the generator module 27. If the power consumption reaches and/or exceeds a predetermined threshold, the control module 6001 issues a user alert by causing an overlay 6052 of power-allocation controls onto the livestream of the surgical field on the display 6005. The control module 6001 may then adjust power consumption in accordance with the user adjustments of the power-allocation controls.

In certain instances, the control module 6001 reduces power requirements of one or more systems to implement the user adjustments. For example, the control module 6001 may reduce the brightness of the display 6005 in response to a user input that selects a reduction of power allocation to the system 6000 in favor of maintaining power allocation to the generator module 27. Additionally, or alternatively, the control module 6001 may slow, delay, or suspend certain tasks, such as secondary image processing tasks, performed by the system 6000 in response to a user input that selects a reduction of power allocation to the system 6000 in favor of maintaining power allocation to the generator module 27.

In certain instances, the user adjustments of the power-allocation controls can favor power allocation to the system 6000 over the generator module 27. This may occur where the user is at a critical step that requires optimal visualization, for example sealing a vessel, and where an adequate operation of the energy device can still be achieved at a lower power level, perhaps by increasing tissue sealing time. In such instances, the control module 6001 may cause the surgical energy device and/or the generator module 27 to adjust one or more of their settings to reduce power draw in favor of the system 6000.

In some implementations, the control module 6001 automatically intercedes to make the power allocation adjustments, in response to detecting the failure, without user input. In such implementations, the control module 6001 only alerts the user to the changes caused by the automatic changes to the power consumption. For example, the control module 6001 may overlay on the livestream on the display 6005 an alert to a change in brightness of the display 6005 and/or a temporary suspension of an overlay of visual content such a surgical data overlay due, for example, to the temporary suspension of the image processing yielding the overlay. The overlay can be reintroduced upon completion of tissue sealing by the surgical energy device. Alternatively, the overlay can be intermittently displayed rather than being continuously displayed to reduce power consumption of the system 6000 in favor of the generator module 27.

In some implementations, the user adjustments to the power-allocation controls are implemented via one or more active discrete current limiting circuits that are configured to prevent one or more systems from exceeding a max fuse limit threshold, for example.

In some implementations, the system resource is power and the components of the computer-implemented interactive surgical system 1 competing for the power resource are the system 6000, or any other visualization system of the computer-implemented interactive surgical system 1, and the smoke evacuator module 26 (FIG. 3). During a surgical tissue sealing procedure, for example, the computer-implemented interactive surgical system 1 can be configured to perform two tasks that collectively require a power consumption that reaches, or exceeds, the predetermined threshold. The first task can be a visualization task, e.g. providing a spectral view, of the surgical field, and the second task can be extracting smoke from the surgical field, for example. The smoke is a byproduct of the tissue sealing process by an energy device.

In such implementations, if the failure is detected 6051, the control module 6001 may then issue a user alert, for example by causing an overlay 6052 of power-allocation controls onto the livestream of the surgical field on the display 6005, as discussed previously. The control module 6001 may then adjust power consumption in accordance with the user adjustments of the power-allocation controls. In certain instances, the control module 6001 may recommend an adjustment of the smoke evacuation module 26 to a lower setting, for example by overlaying visual content representing the recommended adjustment onto the livestream of the surgical filed on the display 6005. Additionally, the control module 6001 may also cause visual content representative of slowdown of the smoke evacuation to be overlaid. Presenting such visual contents in the manner indicated affords a user of the surgical energy device an opportunity to slow down the sealing process by adjusting the surgical energy device to a lower setting that produces less smoke. When the additional power requirements of the system 6000 ceases, for example due to a completion of the image processing associated with the spectral view, the control module 6001 causes an overlay of visual content representative of an alert to inform the user that the smoke evacuation module 26 is returning to its original setting.

In various instances, methods similar to the method 6050 can be implemented to address other failures, e.g. overheating and/or noise, which can negatively influence a surgical procedure performed using the computer-implemented interactive surgical system 1. In such instances, failure detection can be achieved based on readings of one or more internal and/or external sensors of one or more components of the computer-implemented interactive surgical system 1. The sensor readings can then be compared to predetermined thresholds to detect a failure. For example, an overheating failure can be detected if one or more temperature sensor readings are at, or greater, than a predetermined temperature threshold. In response to the failure, the control module 6001 may overlay virtual controls onto a livestream of the surgical field of the surgical procedure on the display 6005, thereby presenting the user with an opportunity to change settings of one or more of the components of the computer-implemented interactive surgical system 1 to address the overheating. Similar methods can be utilized to address noise levels.

In various instances, the display arrangement, in accordance with the method 6010, includes a segmentation of the display 6005 to accommodate visual representations of the surgical data. Size, shape, display time, display location, display three dimensional arrangement (e.g. foreground, background), display blinking, highlighting, and/or font of concurrently displayed segments can depend on a number of factors including the nature, complexity, and/or criticality of the surgical data. In some implementations, pairing information of surgical data configured to be displayed simultaneously can be provided in a database or table stored on a storage medium such as the memory 6003. The processor 85 of the control module 6001 may determine whether multiple surgical data are to be displayed simultaneously based on the stored information.

In some implementations, visual representations of two different surgical data are configured to be displayed simultaneously in a segmented mode onto the display 6005, but only one of the visual representations is ready for display. In such implementations, the unready visual representation can be represented as a blank area in its assigned segment. Additionally, as described supra, the control module 6001 can be configured to repurpose FPGA for additional processing speed to aid in readying the unready visual representation. Alternatively, the unready visual representation can be displayed at a lower quality to ensure that the surgical data are displayed simultaneously.

In certain instances, visual representations of multiple surgical data are configured to be displayed simultaneously, for example in the segmented mode, onto the display 6005, but the system 6000 lacks sufficient processing capabilities to simultaneously display all of the different surgical data. In response to detecting a deficiency in its processing capabilities, the system 6000 may prioritize the display of higher priority surgical data over lower priority surgical data, based on assigned display-priority values of the surgical data, for example.

In other instances, the display issue can be a lack of sufficient display area at the display 6005 to simultaneously display visual representations of multiple surgical data in the segmented mode. In such instances, a display arrangement implemented by the control module 6001 may comprise a picture-in-picture type display arrangement, wherein a first visual representation is displayed inside a second visual representation. In other words, the first visual representation may appear in the foreground, and may be smaller in size than the second visual representation appearing in the background. Additionally, through any suitable user interface 6007, the clinician may toggle between the two visual representations by selectively causing one of the visual representations to move to the foreground, and the other to the background.

The control module 6001 can be configured to detect a lack of sufficient display area based on a predetermined display size of the display 6005, and a calculated display size of the visual representations of the surgical data. In some implementations, a predetermined equation can be utilized in the calculation. In other instances, where the visual representations are the same, or similar, in size, the lack of sufficient display is detected where the number of visual representations of the surgical data is equal to, or greater than, a predetermined threshold.

In various instances, the display arrangement, in accordance with the method 6010, comprises a transition between display modes such as, for example, a static, or passive, display mode and a dynamic, or active, display mode. In some implementations, the control module 6001 is configured to transition a visual representation of a surgical data from the static mode to the dynamic mode. The control module 6001 can be configured to implement the transition in response to a predetermined trigger such as, for example, a change in the priority, criticality, and/or risk associated of the surgical data. For example, a surgical data initially assigned 6012 a low display priority value can be displayed, or overlaid onto a livestream of a surgical field, in a static display mode that is later transitioned into an active display mode due to an increase in the display priority value of the surgical data to a higher display priority value.

Further to the above, in some implementations, the static mode includes displaying, or overlaying, a static visual representation of the surgical data associated with a surgical instrument 21 onto a side, or corner, of a display 6005, for example. In contrast, the active mode may include overlaying an active visual representation of the surgical data onto a part of the surgical instrument 21 in the livestream of the surgical field and/or moving highlighted areas in the static visual representation, for example. In various implementations, the static display mode differs from the active display mode in one or more of size, shape, display time, display location, display three dimensional arrangement (e.g. foreground, background), display blinking, highlighting, and/or font, for example.

In some implementations, the transition from the static display mode to the active display mode is based on an actuation of, or activation of, a surgical instrument 21, which signals a technique sensitive step that requires a real-time dynamic display. For example, the actuation of, or activation of, a surgical instrument 21 in a subsequent staple firing into the tissue, which requires a specific angle of firing with respect to a previous firing, can trigger a transition into the active display mode. First, certain display elements such as visual representations of the surgical data (e.g. various firing and/or tissue parameters) can be displayed, or overlaid, in the static display mode. Then, in response to the actuation of, or activation of, a surgical instrument 21, in a subsequent firing, the control module 6001 causes a transition into the dynamic display mode, where display elements are highlighted and/or moved, for example. In various instances, the subsequent firing that triggers the transition involves a staple firing that also deploys a tissue adjunct (e.g. tissue thickness compensator).

In some implementations, the control module 6001 is configured to cause display elements in the static display mode to become smaller in size, become less highlighted, and/or disappear overtime. Various operational parameters of a surgical instrument 21 can initially be presented in the dynamic display mode, then transitioned into the static display mode, as the significance level of such parameters changes. In certain exemplifications, certain display elements are assigned predetermined locations onto a display 6005, for example, in the static display mode, which are then changed in the active display mode.

In some implementations, a visual representation of surgical data, e.g. a biomarker, is presented in a static display mode, e.g. solid color not highlighted, while values associated with the biomarker remain within a predetermined range, or below a predetermined threshold. If, however, the values move beyond the predetermined range, or beyond the predetermined threshold, the visual representation of the surgical data can be transitioned into the dynamic display mode by causing certain display elements of the visual representation to change in size, shape, display time, display location, display three dimensional arrangement (e.g. foreground, background), display blinking, highlighting, and/or font, for example.

Figure 19A:
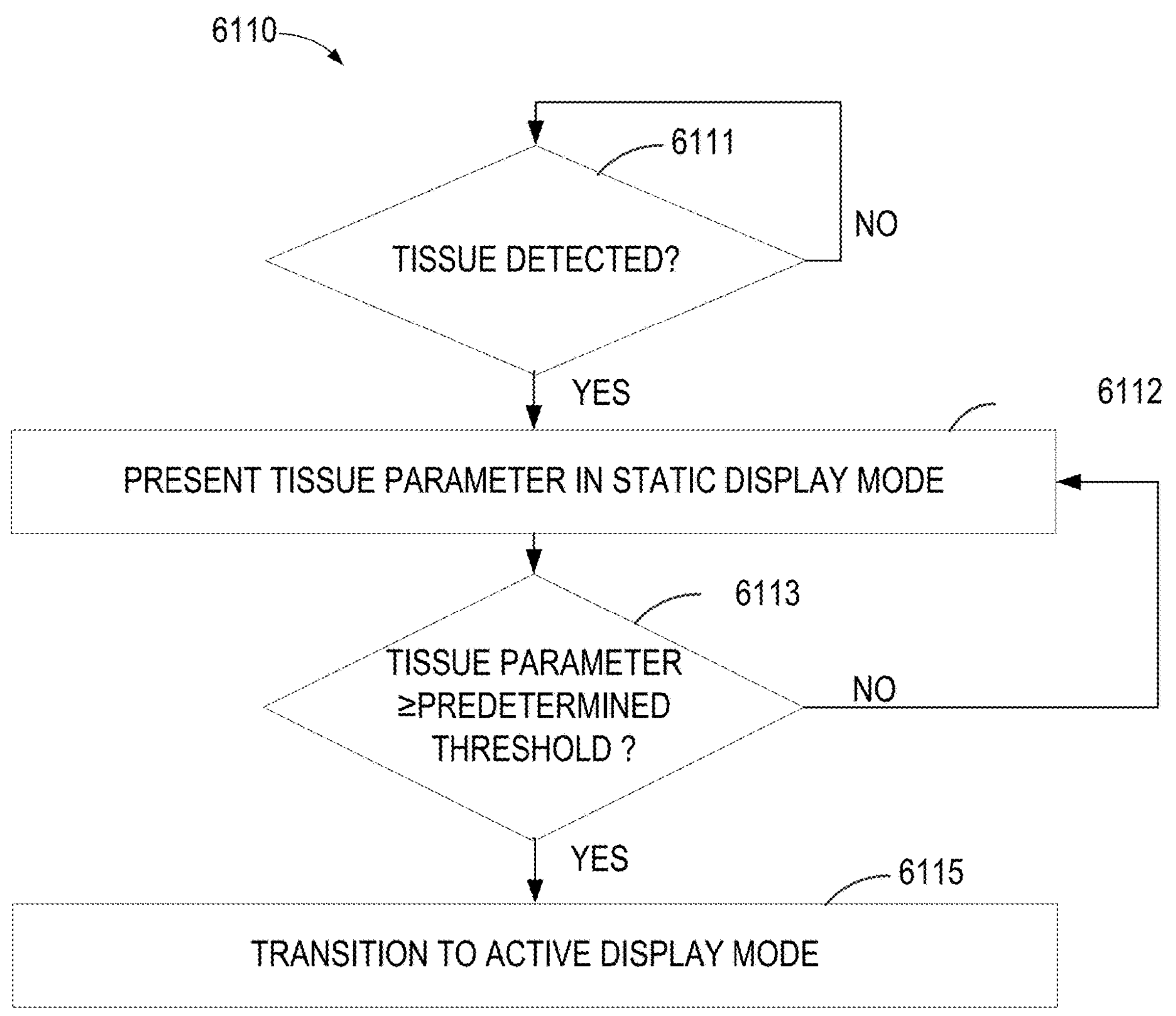
FIG. 19A is a flowchart showing operations of a method for transitioning between the static display mode and the active display mode based on the surgical data, in accordance with at least one aspect of the present disclosure.

FIG. 19A is a flowchart showing operations of an example method 6110 for transitioning between the static display mode and the active display mode based on the surgical data. In some implementations, the method 6110 can be executed by the computer-implemented interactive surgical system 1, for example. In the illustrated example, the surgical data comprises a tissue parameter. The tissue parameter is tissue impedance. Other tissue parameters such as, for example, tissue thickness, tissue pressure, tissue conductance, and/or tissue compression can be similarly presented.

Further to the above, the method 6110 includes detecting 6111 tissue between the jaws of an end effector of a surgical instrument 21. In certain instances, tissue detection 6111 can be achieved automatically through object recognition, object tracking, and/or object labeling algorithms, and/or other image processing techniques of image frames of the livestream, for example. Alternatively, the surgical instrument 21 can be configured to detect 61111 the presence of the tissue between the jaws based on signal readings of one or more sensors in the jaws. For example, a tissue can be detected 6111 when a non-therapeutic signal passed through the tissue yields an acceptable tissue impedance.

In response to detecting 6111 the tissue, the method 6110 presents 6112 the tissue parameter in the static display mode, for example, by displaying, or overlaying onto a livestream of the surgical field, a visual representation of the tissue parameter. If 6113, however, the tissue parameter reaches, or exceeds, a predetermined threshold, or becomes outside a predetermined range, the method 6110 further causes a transition 6115 of one or more display elements of the visual representation of the tissue parameter to the active display mode.

In some implementations, the surgical instrument 21 is an energy device configured to seal tissue grasped by the end effector of the surgical instrument 21. At the outset of the treatment, upon detecting 6111 the tissue, tissue impedance is presented in the static display mode. The surgical instrument 21 may communicate to the control module 6001, through a wired, or wireless, interface, surgical data indicative of the tissue impedance to display onto the display 6005, for example, in the static display mode. As energy application to the tissue commences, the tissue impedance changes. If, however, the tissue impedance reaches, or exceeds, a predetermined threshold, or becomes outside a predetermined range, this can be an indication of an immersion of the end effector in a fluid, an electrical short, or merely a low impedance tissue. In any event, a transition 6115 to the active display mode is triggered to alert the clinician to investigate.

In various instances, the control module 6001 determines various surgical information associated with a surgical procedure such as, for example, steps of the surgical procedure, surgical instruments 21 to be utilized in each step, and various risks and/or techniques associated with each of step. Such determination can be based on contextual information generated by the situational awareness module 6006, for example. The control module 6001 can then cause the surgical information to be displayed, or overlaid onto a surgical field of the surgical procedure, in a display arrangement utilizing one or more of the methods described by the present disclosure. For example, a current step, the surgical instruments 21 associated with the current step, risks associated with the current step and/or techniques associated with the current step can be presented in the active display mode, while previous and/or following steps are presented in the static display mode. When a following step becomes a current step, it is transitioned into the active display mode.

Further to the above, the transition 6115 from the static display mode to active display mode can be employed to reflect changes to a procedure plan, reflecting a new layout, for example. In various instances, the surgical information can be segmented for presentation by the control module 6001 into stages of access, separation and/or mobilization, resection, and/or repair and/or augmenting relevant data to surgeon, for example.

In various instances, the transition of a visual representation of a surgical data between the static display mode and the active display mode is based on changes in the use of a surgical instrument 21 linked to, or associated with, the surgical data. The surgical data can be initially presented in the static display mode. If, however, a predetermined change is detected in the use of the surgical instrument 21, a transition of the visual representation of the surgical data to the active display mode is affected.

Figure 19B:
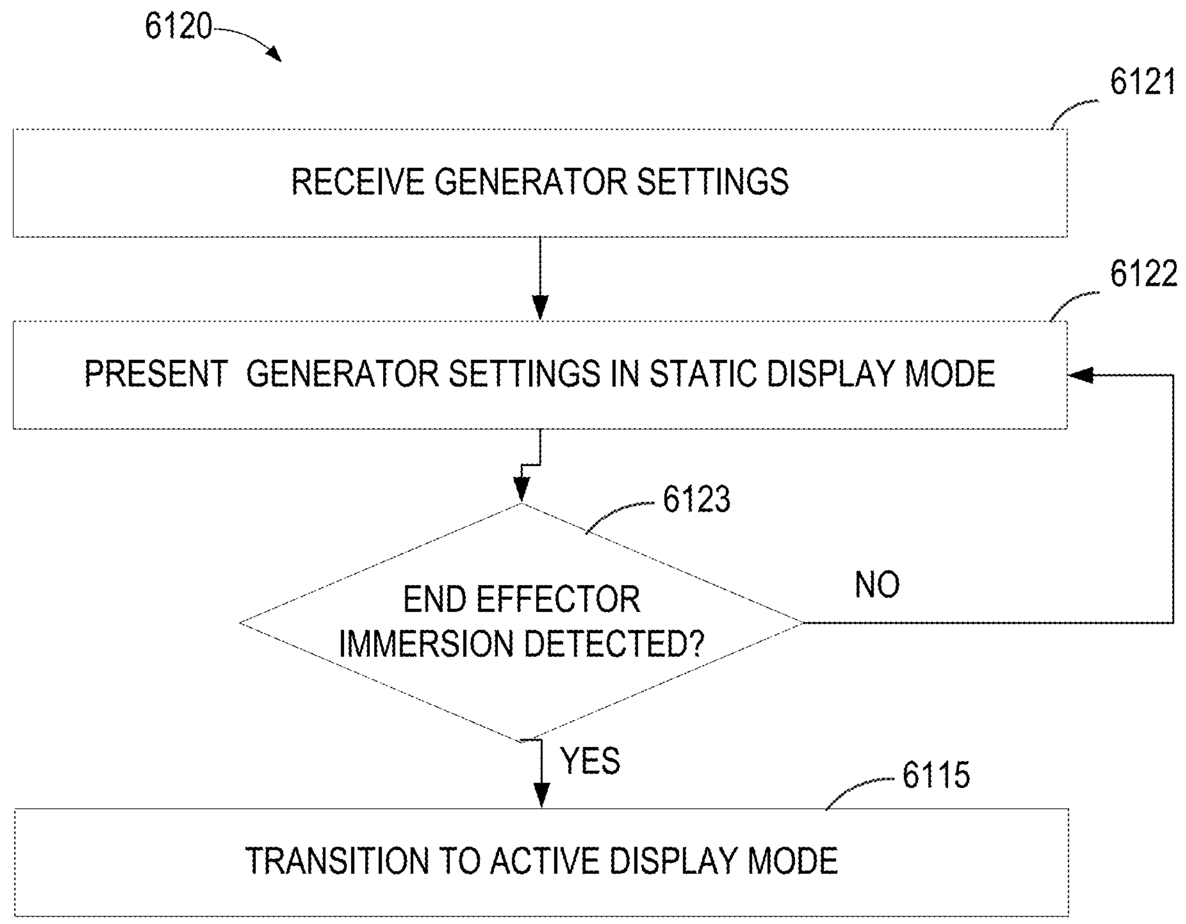
FIG. 19B is a flowchart showing operations of a method for transitioning of a visual representation of a surgical data between the static display mode and the active display mode, in accordance with at least one aspect of the present disclosure.

FIG. 19B is a flowchart showing operations of an example method 6120 for transitioning of a visual representation of a surgical data between the static display mode and the active display mode. The transition is based on, or triggered by, changes in the use of a surgical instrument 21 linked to, or associated with, the surgical data. In some implementations, the method 6120 can be executed by the computer-implemented interactive surgical system 1, for example.

In the illustrated example, the surgical instrument 21 is an ultrasonic surgical instrument configured to coagulate tissue grasped by its end effector in a surgical procedure. The surgical instrument 21 is utilized with a generator in preset generator setting that are received 6121 by the control module 6001 for display, or overlay onto a surgical field of the surgical procedure. The method 6120 further includes presenting 6122 the preset generator settings in the static display mode. If 6123, however, during the surgical procedure, an immersion of the end effector in blood is detected due to an attempted coagulation of a blood vessel that is semi-immersed in blood, for example, new generator settings are presented in the active display mode. The new generator settings may comprise an increase in the transducer power level in response to the end effector immersion in blood. The display, or overlay onto the livestream of the surgical field, of the new generator settings alerts the user of the surgical instrument 21, and affords an opportunity for the user to adjust the position of the end effector if the increased power levels are not desirable.

In some implementations, detecting the immersion of the end effector in blood is achieved by one or more sensors. In one example, a non-therapeutic current can be passed. If a short circuit is detected, the short circuit is indicative of the immersion in blood. In response, surgical data indicative of the immersion is communication wirelessly, or through a wired interface, to the control module 6001.

In various instances, a display arrangement in accordance with the method 6010 includes initially presenting a visual representation of the surgical data in the static display mode. Then the method 6010, in response to a change in a status of a surgical instrument 21 associated with the surgical data, causes a change in one or more display elements of the visual representation such as, for example, values associated with the surgical data. The changes includes, for example, encountering a staple cartridge lockout, activation of an advanced energy device, a transition between an open and a closed configuration of an end effector of a surgical instrument 21.

As described previously, the change in the one or more values associated with the surgical data can be performed in the static display mode. Alternatively, in some implementations, the change can be accompanied by a transition from the static display mode to the active display mode to provide an additional alert. Such implementations include, for example, various adaptation techniques such as, for example, pausing to allow for tissue creep and/or tissue compression, detecting unbalanced tissue in the jaws of an end effector of the surgical instrument 21, and/or detecting that the clamp of the jaws is inducing inappropriate tissue tension.

In various instances, a display arrangement in accordance with the method 6010 includes a transition from a first dynamic display mode to a second dynamic display mode, wherein the second dynamic display mode comprises, or represents, a higher priority, risk, and/or criticality than the first dynamic display mode. In one example, blood pressure is tracked during a surgical procedure via a blood pressure monitoring device that may communicate its readings to the control module 6001, for example, using a wireless, or wired, interface. A visual representation of the blood pressure can then be presented in a first dynamic display mode, due to the importance of the blood pressure data. If, however, during the surgical procedure, an increase is detected in blood pressure data beyond acceptable limits, a transition is made to elevate the blood pressure data to a second dynamic display mode, for example, to ensure an appropriate alert is delivered.

In various implementations, one or more characteristics of visual representations of surgical data such as, for example, the size, shape, display time, display location, display three dimensional arrangement (e.g. foreground, background), display blinking, highlighting, and/or font of the visual representations can be based on the assigned 6012 display-priority values. In certain instances, the assigned 6012 display-priority values can yield a display arrangement with a display conflict. For example, determining a display arrangement based on assigned display priority values may yield more than one visual representation of the surgical data with the same location on a display 6005, for example.

Figure 20:
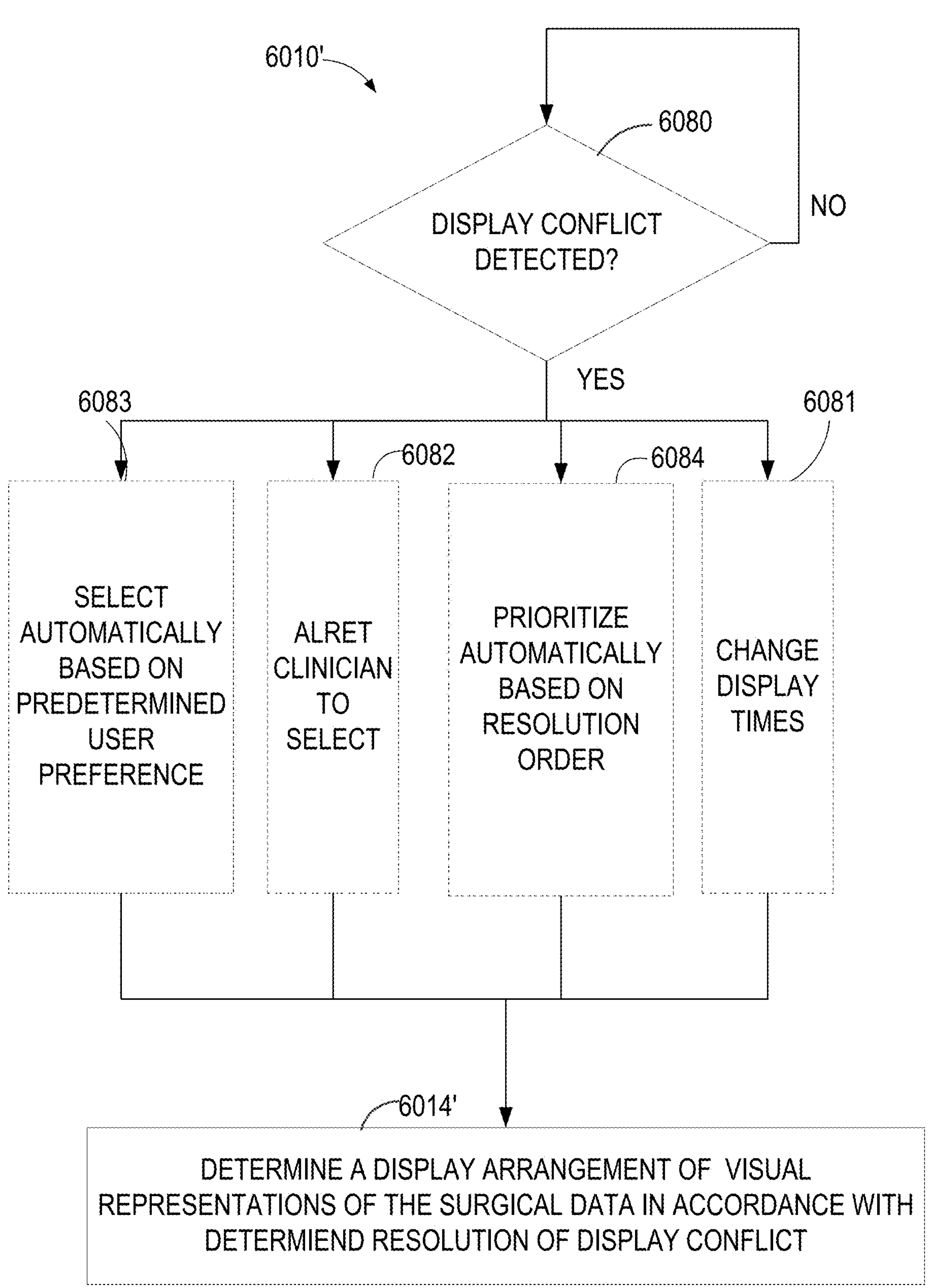
FIG. 20 is a flowchart showing operations of a method for resolving display conflicts in a display arrangement, in accordance with at least one aspect of the present disclosure.

FIG. 20 is a flowchart showing operations of an example method 6010' for resolving display conflicts in a display arrangement. The method 6010' is similar in many respects to the method 6010. Common details between the two methods are not repeated herein for brevity. In certain instances, as illustrated in FIG. 20, a detected 6080 display conflict can be resolved by changing 6081 one or more display times of competing visual representations to resolve the conflict. Alternatively, the clinician can be made aware of the conflict, and can be offered a choice, on the display 6005, to select 6082 between the different surgical data. Alternatively, the selection 6083 can be made automatically based on a predetermined preference of the clinician, which can be based on user-input or contextual information generated by the situational awareness module, for example 6006.

In some implementations, detecting 6080 a display conflict between a first surgical data and a second surgical data includes retrieving, by the processor 85, for example, display priority information for the first surgical data and the second surgical data from the memory 6003, for example. The processor 85 may then compare the display priority information of the first surgical data and the second surgical data to determine whether a display conflict is detected 6080.

In certain implementations, the control module 6001 is configured to respond to a detected 6080 display conflict by simultaneously showing visual representations of competing surgical data that are smaller in size than a default size, for example. A clinician is permitted to select between the visual representations though a user interface 6007, for example. In response, the control module 6001 removes the unselected visual representation, and increases the size of the selected visual representation to the default size.

In certain implementations, a detected 6080 display conflict can be resolved by automatically prioritizing 6084 based on a resolution order determined based on the surgical data presenting the display conflict. In some implementations, the resolution order is determined based on an order of the surgical steps associated with the surgical data and/or urgencies of risks and/or issues reported by the surgical data.

In certain exemplifications, a display conflict is detected 6080 between a first surgical data and a second surgical data, both presenting high priority issues and/or risks. Moreover, a second resolution associated with the second surgical data cannot be performed until a first resolution associated with the first surgical data is implemented. In such exemplifications, a first visual representation of the first surgical data is automatically prioritized 6084 over a second visual representation of the second surgical data based on the resolution order.

In certain exemplifications, a display conflict may arise between a first surgical data associated with a lockout preventing actuation of a surgical instrument 21 and a second surgical data associated with a suboptimal tissue thickness of a tissue being treated by the surgical instrument. In such exemplifications, a predetermined resolution order can be employed to resolve the conflict in favor of the lockout, since the tissue thickness issue, while a high priority, cannot be resolved while the surgical instrument 21 is in a lockout state.

In certain instances, the resolution order can be stored on a storage medium (e.g. the memory 6003) in the form of a database, a table, or any other suitable form. The stored information can list various surgical data and corresponding resolution order. The processor 85 may consult the stored information to identify a resolution order between competing surgical data to resolve a display conflict. In some implementations, the resolution order is based on an order of surgical tasks that will be initiated, or completed, based on the competing surgical data.

In some exemplifications, the control module 6001 may receive first surgical data indicating that a detected staple cartridge (e.g. one loaded onto a surgical instrument 21) has been previously fired. A controller of the surgical instrument 21 may interrogate the staple cartridge by requesting firing information stored on a chip of the staple cartridge, for example, and may determine that the staple cartridge has been previously fired based on the retrieved firing information. First surgical data comprising the firing information can then be communicated to the control module 6001, wirelessly or through a wireless communication. In addition, the control module 6001 may receive second surgical data associated with a closure of the end effector of the surgical instrument 21 onto a tissue being stapled in a surgical procedure involving the surgical instrument 21 that is loaded with the previously-fired staple cartridge. For example, the second surgical data may relate to tissue thickness and/or tissue position between jaws of the end effector.

Further to the above, the control module 6001 detects 6080 a display conflict as the first surgical data, previously-fired staple cartridge, and the second surgical data, end effector closure onto tissue, both comprise high priority statuses. To determine a display arrangement of visual representations of the first and second surgical data onto the display 6005, for example, the processor 85 checks a resolution order information stored on a storage medium (e.g. the memory 6003) in the form of a database, a table, or any other suitable form. In the present example, the first issue, previously-fired staple cartridge, presented by the first surgical data, must be resolved before a second issue, end effector closure onto tissue, presented by the second surgical data. This is because resolving the end effector closure onto tissue is immaterial if the previously-fired staple cartridge cannot be used to treat the tissue.

Once the display conflict is resolved, the method 6010' proceeds with displaying 6014' visual representations of the first surgical data and second surgical data in accordance a display arrangement selected based on the resolution order. For example, a first visual representation of the first surgical data can be displayed prior to a second visual representation of the second surgical data. Other suitable display arrangements, as described elsewhere in the present disclosure, can be employed.

In various aspects, a surgical procedure involves stapling a tissue using a surgical instrument 21 such as, for example, a surgical stapler. The surgical procedure typically includes positioning an end effector of the surgical instrument 21 in a surgical field, and actuating the end effector to grasp tissue between jaws of the end effector. The jaws place the grasped tissue under compression. Since the tissue comprises water, the grasped tissue gradually changes in response to being compressed by the jaws of the end effector in process known as tissue creep, until the tissue reaches the steady state. Moreover, the gap between the jaws and the tissue thickness may also change until the tissue reaches the steady state. Also, tissue flow, or tissue motion, may occur until the tissue reaches the steady state. In some implementations, for a successful stapling, the tissue is allowed a wait-time to achieve the steady state. Parameters associated with the previously-described tissue changes such as wait-time parameters, tissue-thickness parameters, and/or instrument gap parameters are important for properly assessing when a tissue steady-state is reached.

Figure 21:
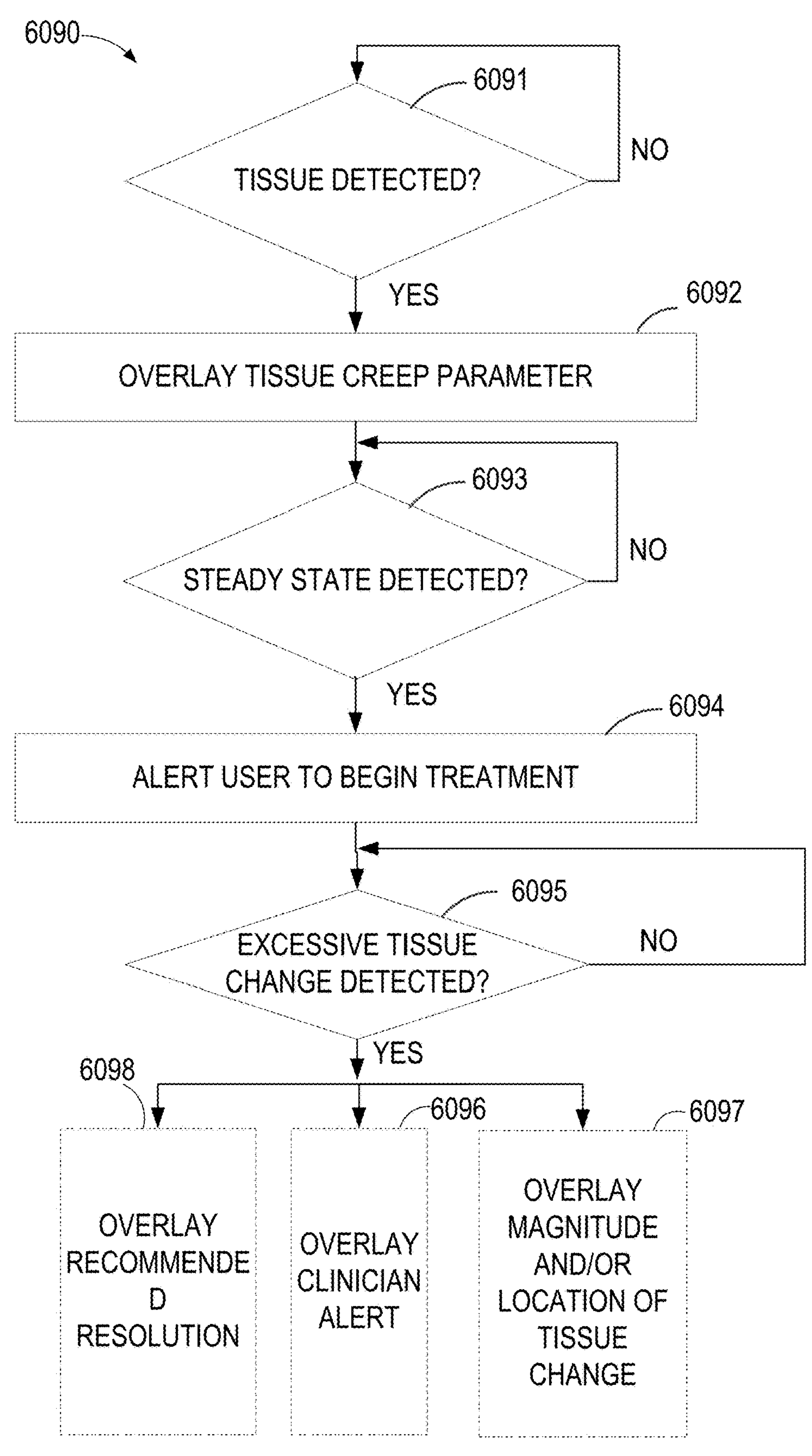
FIG. 21 is a flowchart showing operations of a method for addressing tissue changes in a surgical procedure that employs a surgical instrument, in accordance with at least one aspect of the present disclosure.

FIG. 21 is a flowchart showing operations of an example method 6090 for addressing tissue changes (e.g. tissue creep, tissue flow, tissue compression) in a surgical procedure that employs a surgical instrument 21. In some implementations, the method 6090 includes detecting 6091 tissue between the jaws of an end effector of the surgical instrument 21. In certain instances, tissue detection 6091 can be visually achieved automatically through object recognition, object tracking, and/or object labeling algorithms, and/or other image processing techniques of image frames of the livestream, for example. Alternatively, the surgical instrument 21 can be configured to detect 6091 the presence of the tissue between the jaws based on signal readings of one or more sensors in the jaws. For example, a tissue can be detected 6091 when a non-therapeutic signal passed through the tissue yields an acceptable tissue impedance.

In response to detecting 6091 the tissue, the method 6090 may display, or overlay 6092 onto a livestream of the surgical field, at least one parameters of tissue change (e.g. tissue creep, tissue flow, tissue compression) and/or parameters of the surgical instrument gap distance between the jaws of the end effector, and/or wait-time. In certain implementations, the method 6090 further includes alerting 6094 the user of the surgical instrument 21 when the steady state has been reached to begin tissue treatment. In certain instances, the steady state is detected 6093 based on one or more of the tissue change parameters and/or one or more of the surgical instrument parameter. For example, the steady state can be detected 6093 when one or more of the tissue flow, tissue creep, tissue thickness, tissue compression, gap distance between the jaws of the end effector, and/or wait-time is at, or beyond, a predetermined threshold. Alternatively, the steady state can be detected 6093 If a rate of change of one or more of the tissue flow, tissue creep, the tissue thickness, tissue compression, gap distance between the jaws of the end effector, and/or wait-time is less than, or equal, to a predetermined threshold. Additionally, or alternatively, the steady state can be automatically visually detected 6093 based on object recognition, object tracking, and/or object labeling algorithms, and/or other image processing techniques that may monitor, for example, a change in the tissue.

Figure 26:
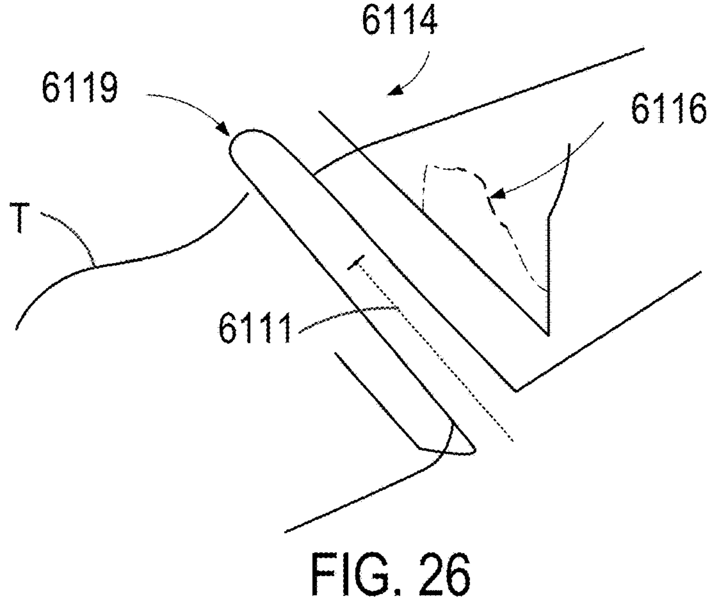
FIG. 26 illustrates a display arrangement, in accordance with methods of the present disclosure.

In some implementation, the method 6090 further includes automatically monitoring tissue change visually during the application of a treatment by the surgical instrument 21 by utilizing one or more suitable object recognition, object tracking, and/or object labeling algorithms, and/or other image processing techniques of image frames of the livestream, for example. In certain instances, the treatment can, for example, be the firing of staples into the grasped tissue. If 6095, during firing, the tissue change reaches an excessive level, the method 6090 may further include displaying, or overlaying 6096, an alert to the clinician. In certain instances, the method 6090 includes displaying, or overlaying 6097, a visual representation of the location and/or magnitude of the excessive tissue change, as illustrated in FIG. 26, for example. In some implementations, tissue change is automatically monitored visually by tracking size, location, color, and/or movement of one or more tissue targets of in the grasped tissue, for example.

The method 6090 may also include displaying, or overlaying 6098, a recommended resolution such as, for example, adjusting one or more parameters of the surgical instrument 21 such as one or more closure parameters (e.g. jaw clamping, jaw pressure, distal tip load) and/or firing parameters (e.g. firing speed, I-beam speed). In certain instances, the recommended resolution can be additional wait-time. In certain instances, the surgical instrument 21 is an ultrasonic instrument, and the recommended resolution is one that decreases a distal tip load of the end effector. In other instances, the surgical instrument 21 is a surgical stapler, and the recommended resolution is one that increases a distal tip load of the end effector.

In various instances, the tissue change, e.g. tissue flow, is affected, at least in part, by a tension suffered by the tissue grasped between the jaws. In certain instances, the tissue tension is due to a movement such as a rotation of the end effector from a neutral positon while grasping the tissue. In such instances, the overlaid 6098 resolution can be in the form of a recommended adjustment to a rotational position of the end effector. Excessive tissue tension can be automatically observed by utilizing one or more suitable object recognition, object tracking, and/or object labeling algorithms, and/or other image processing techniques of image frames of the livestream, for example.

In some implementations, position and/or orientation of the end effector can be determined using one or more sensors including an accelerometer, a gyro, a relative position sensor, and/or a three-dimensional magnetic sensor. In some implementations, the sensors can generate position information characterizing one or more position changes. The position information can be transmitted via a wired or wireless interface to the control module 6001.

In some implementations, the accelerometer may be a single, double, or triple axis accelerometer. The accelerometer may be employed to measure proper acceleration that is not necessarily the coordinate acceleration (rate of change of velocity). Instead, the accelerometer may see the acceleration associated with the phenomenon of weight experienced by a test mass at rest in the frame of reference of the accelerometer. Additionally, or alternatively, position and/or orientation of the end effector can be automatically observed by utilizing one or more suitable object recognition, object tracking, and/or object labeling algorithms, and/or other image processing techniques of image frames of the livestream, for example.

In response to detection of a tissue tension of the tissue grasped by the jaws of an end effector, the control module 6001 may display, or overlay onto the livestream of the surgical field, visual representations of the tissue tension, its magnitude, and/or the rotational orientation responsible for the tissue tension. In some implementations, as illustrated FIGS. 22A-22C, visual representations 6100, 6101, 6102 of tissue tension may provide positional information of the end effector in three dimensional space, for example. In some implementations, the positional information of the end effector is represented by a first axis (e.g. x-axis) extending centrally and longitudinally through the end effector, a second axis (e.g. y-axis) perpendicular to the first axis and extending in first plane with the first axis, and a third axis (z-axis) perpendicular to the first axis and extending in a second plane with the first axis, wherein the first plane intersects the second plane at the first axis.

Each of the coordinate axes can be presented in a first form (e.g. color, shape, size), while the end effector is in a neutral state with respect to the coordinate axes, as illustrated in FIG. 22A. In response to detecting an excessive deviation from the neutral state about one or more coordinate axes, the control module 6001 causes the one or more coordinate axes to change to a second form different than the first form. In other instances, the excessive deviation from the neutral state can be a first deviation, and can be based on a first predetermined threshold or range, while a second deviation can be more excessive than the first deviation, and can be based on a second predetermined threshold or range different than the first predetermined threshold or range, for example. In such instances, the neutral state can be presented in the first form, the first excessive deviation can be presented in the second form, and the second excessive deviation can be presented in a third form different than the first form and the second form. In certain implementations, the first form includes a green color, the second form includes a yellow color, and the third form includes a red color.

In illustrated example, a first excessive deviation from the neutral state is detected about the y-axis. In response, the control module 6001 causes the y-axis to be switched from the first form to the second form, while the x-axis and the z-axis remain in the first form, as illustrated in FIG. 22B. In the illustrated example, the first excessive deviation is greater than, or equal, to the first predetermined threshold. Then, as illustrated in FIG. 22C, a second excessive deviation, greater than or equal to the second predetermined threshold, is detected about the x-axis, while the first excessive deviation about the x-axis has been remedied. In response, the control module 6001 causes the Y-axis to return to the first form, and the x-axis to be changed to the third form.

In various instances, different deviations (e.g. the first and second excessive deviations) from the neutral state may comprise different severities, and can be presented in different forms indicative of the severities. For example, a first excessive deviation can be presented by a yellow color, while a second excessive deviation, more severe than the first excessive deviation, can be presented in a red color. In some implementations, deviations from the neutral state are determined based on ranges of angles of rotation about one or more of the coordinate axes. For example, the neutral state with respect to a first axis is detected where an angle of rotation of the end effector with respect to the first axis meets a range of about ±A°, the first excessive deviation is detected where an angle of rotation of the end effector with respect to the first axis meets a range of about ±B°, and the second excessive deviation is detected where an angle of rotation of the end effector with respect to the first axis meets a range of about ±C°. In the illustrated example, A, B, and C are integers, wherein A is less than B, and B is less than C.

Figure 23A:
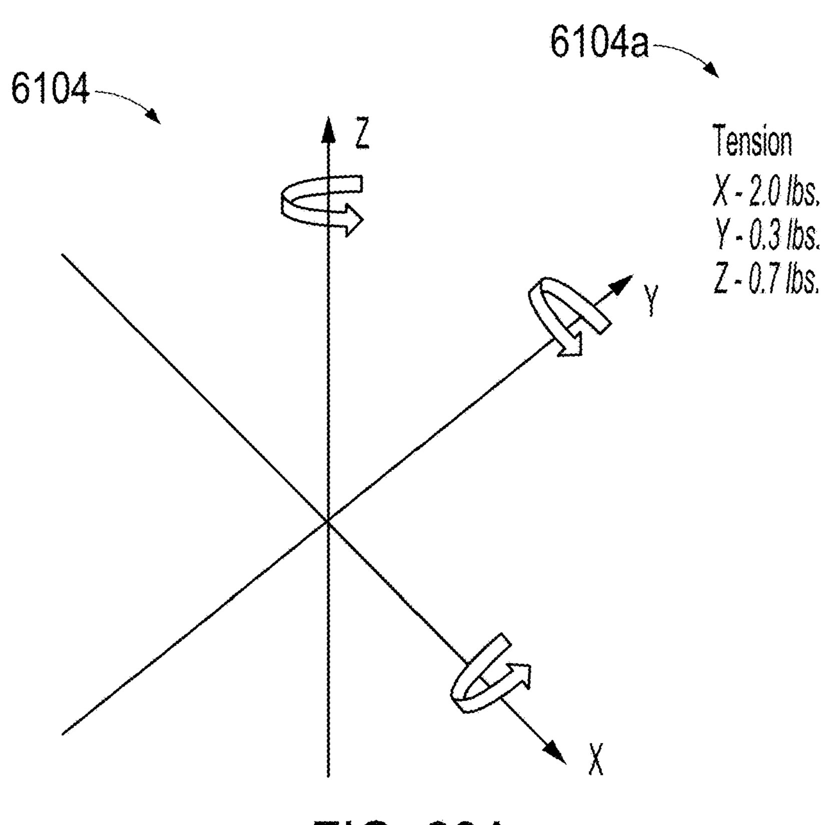
FIGS. 23A-23B illustrate display arrangements, in accordance with at least one aspect of the present disclosure.
Figure 23B:
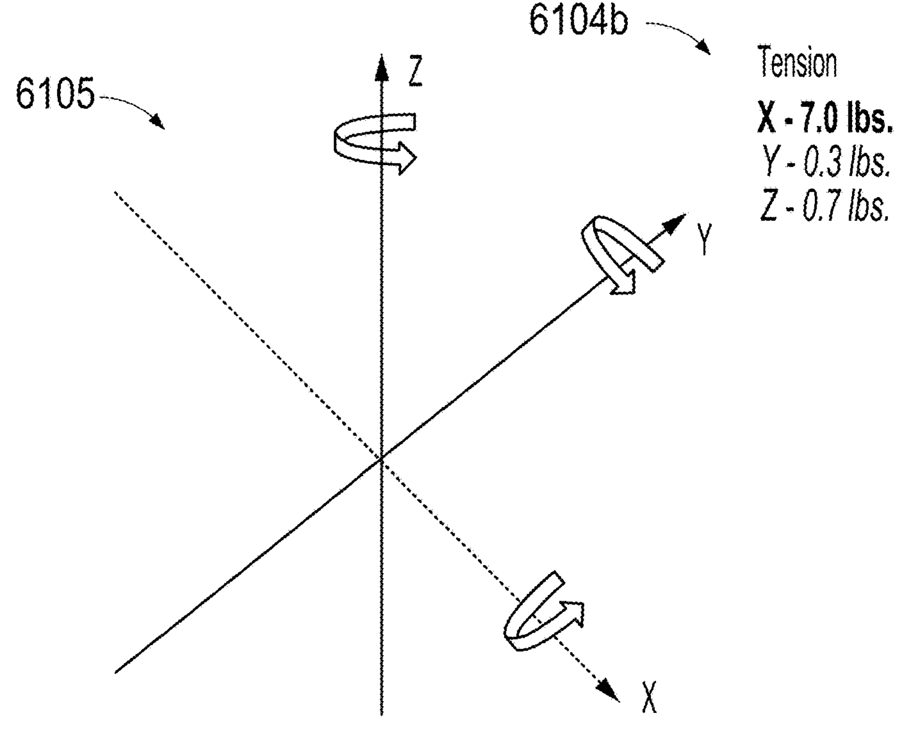

Referring to FIGS. 23A-23B, in some implementations, visual representations 6104, 6105 of the tissue tension may further include tissue tension measurements 6104*a*, 6105*a* associated with each of the coordinate axes. The control module 6001 may cause the tissue tension measurements to change form (e.g. color, size, and/or shape) in response to an excessive deviation in tissue tension (e.g. from 2.0 lbs. to 7.0 lbs.).

Figure 24:
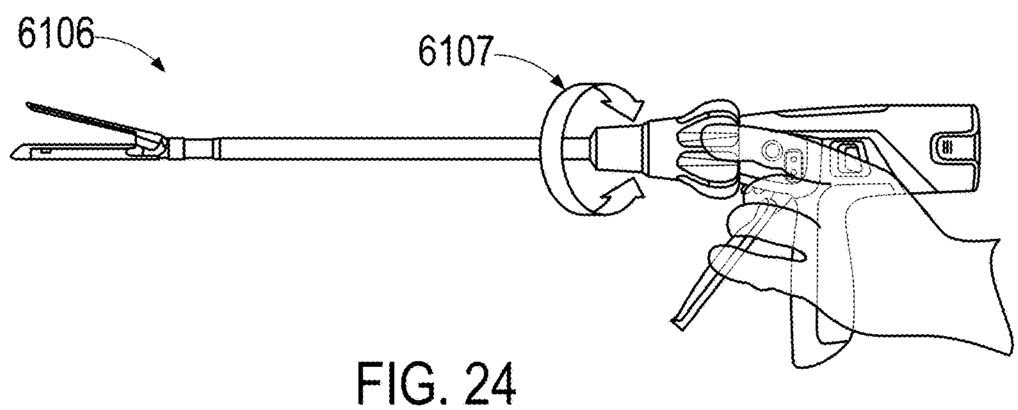
FIG. 24 illustrates a display arrangement, in accordance with at least one aspect of the present disclosure.

In some implementations, the control module 6001 may further cause a recommendation to be displayed, or overlaid onto the livestream of the surgical field, to address an excessive tissue tension. In some exemplifications, as illustrated in FIG. 24, the recommendation comprises a visual representation 2106 showing the surgical instrument 21 with an arrow 6107 representing the recommended rotation to transition the end effector of the surgical instrument 21 to the neutral state.

FIGS. 24-30 illustrate various display arrangements determined 6013 based on surgical data detected 6011, in accordance with the method 6010 and/or any other suitable method of the present disclosure. The display arrangements illustrated in FIGS. 24-30 are represented in the context of a surgical instrument 21 configured to staple and cut tissue. However, in other implementations, one or more of the display arrangements illustrated in FIGS. 24-30 can be similarly utilized with other surgical instruments in other types of surgical procedures.

A number of the display arrangements described by the present disclosure involve overlaying various visual representations of surgical data onto a livestream of a surgical field shown on a display such as, for example, the display 6005. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

Figure 25:
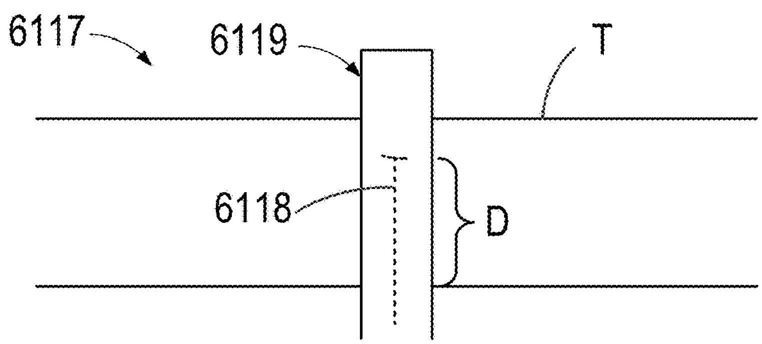
FIG. 25 illustrates a display arrangement, in accordance with at least one aspect of the present disclosure.

FIG. 25 illustrates a display arrangement 6117 that includes a mixed reality view presented by the control module 6001, for example, on a display 6005, for example. The display 6005 shows a livestream of a surgical field during a surgical procedure that utilizes a surgical instrument 21 to staple and cut tissue T grasped by an end effector 6119 of the surgical instrument 21. In the illustrated example, the display arrangement 6117 overlays a transection progress line 6118, or a staple firing progress line, on a channel of the end effector 6119. Moreover, the display arrangement 6117 overlays a distance D traveled by a firing member, or a cutting member, onto the channel of the end effector 6119 to aid a clinician in following the firing progress of the surgical instrument 21.

In some implementations, the control module 6001 detects a change in one or more parameters of the tissue grasped by the end effector 6119 and/or parameters of the surgical instrument 21, beyond a predetermine threshold, or beyond a predetermine range, for example. In at least one implementation, the parameter change is a change in firing speed equal to, or less than, a predetermined threshold. For example, the control module 6001 may receive surgical data indicative of the parameter change through a wired, or wireless, communication interface with the surgical instrument 21 and/or a surgical hub 6 (FIG. 1). In response to detecting the parameter change, the control module 6001 may cause a change in the transection progress line 6118, or a staple firing progress line, on a channel of the end effector 6119, including a change in color, size, shape, display time, display location, display frequency, highlighting, or a combination thereof.

Additionally, or alternatively, in response to detecting the parameter change, the control module 6001 may cause an overlay of a virtual channel, overlaid onto the end effector 6119, to change at least one color, size, shape, display time, display location, display frequency, highlighting, or a combination thereof, in accordance with a magnitude of the change, in accordance with a value of the parameter, or in accordance with a risk level associated with the parameter change.

FIG. 26 illustrates a display arrangement 6114 that is presented by the control module 6001, for example, on a display 6005, for example, in accordance with methods of the present disclosure. The display 6005 shows a livestream of a surgical field during a surgical procedure that utilizes a surgical instrument 21 to staple and cut tissue T grasped by an end effector 6119 of the surgical instrument 21. In the illustrated example, the display arrangement 6117 overlays a tissue marker 6116 indicative of tissue flow onto the tissue T. Excessive tissue flow can be detected as described in connection with the method 6090 of FIG. 21, for example. In the illustrated example, the display arrangement 6114 combines an overlay of the transection progress line 6118 and the tissue marker 6116. Other display arrangements may only comprise the tissue marker 6116.

Figures 27A, 27B, 27C:
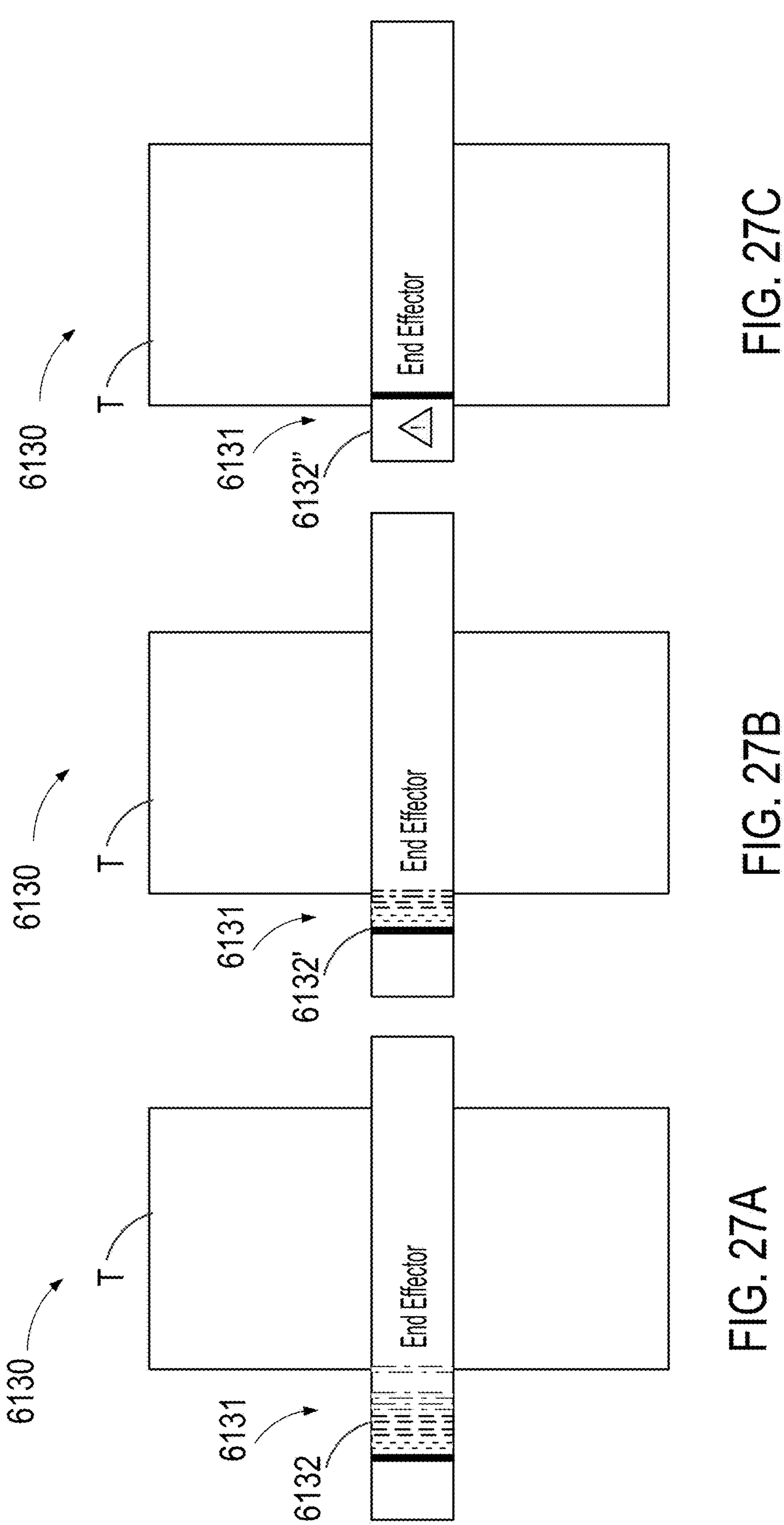
FIGS. 27A-27C illustrate a display arrangement, in accordance with methods of the present disclosure.

FIGS. 27A-27C illustrate a display arrangement 6130 that provides a visual representation 6131 of surgical data, in accordance with at least one aspect of the present disclosure. In some implementations, the display arrangement 6130 is presented by the control module 6001, for example, on a display 6005, for example, in accordance with methods of the present disclosure. In the illustrated example, the display arrangement 6130 presents a visual representation 6132, in the form of a translucent overlay 6133, indicative of a tissue flow during a firing sequence of a surgical instrument 21. During the firing sequence, the surgical instrument 21 is configured to deploy staples into a tissue T grasped by an end effector of the surgical instrument 21, and concurrently cut the tissue T. In the illustrated example, the display arrangement 6130 is presented in a dynamic display mode, wherein a change in a display element 6132 (FIG. 27A), 6133' (FIG. 27B), 6133" (FIG. 27C) of the visual representation 6131 is depicted.

The display element may track the tissue flow across the width of the end effector. Different locations can be presented in different forms (e.g. colors, shapes, and/or sizes), wherein the different forms represent different levels of tissue flow in the different locations. In the illustrated example, the display element 6132 represents an acceptable tissue flow condition, and the display element 6132' represents a low risk tissue flow condition. On the contrary, the display element 6132''' represents a high risk tissue flow condition.

Figure 28:
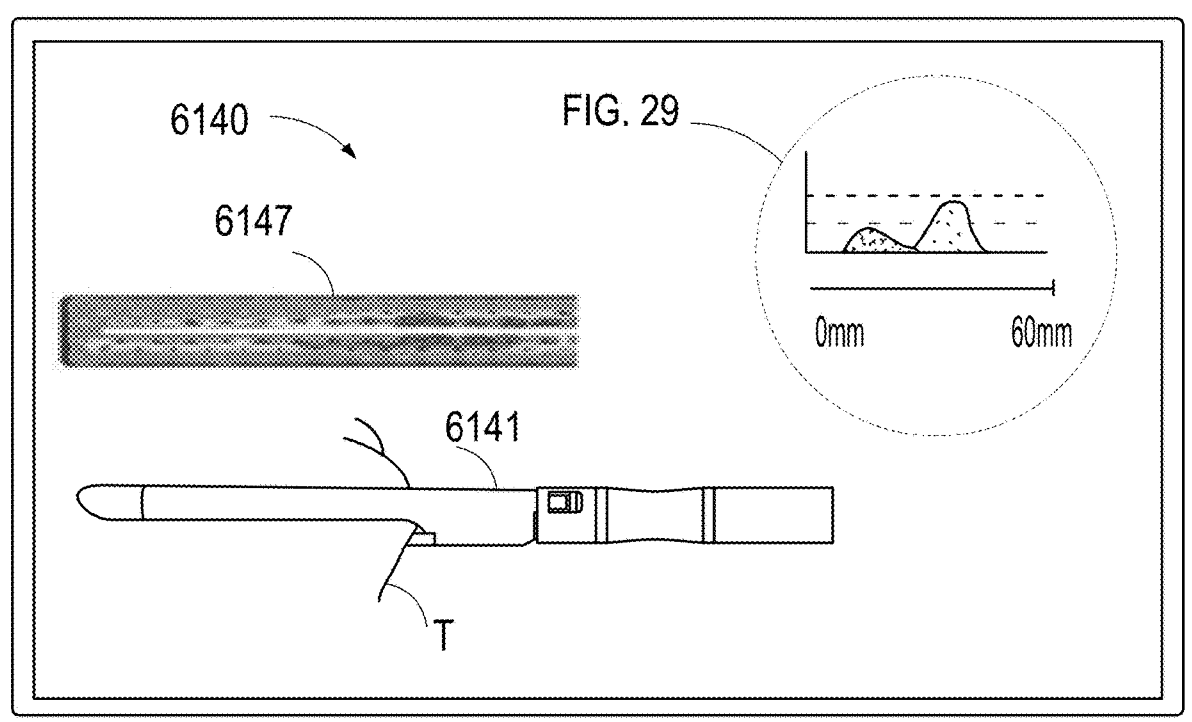
FIG. 28 illustrates a display arrangement, in accordance with methods of the present disclosure.
Figure 29:
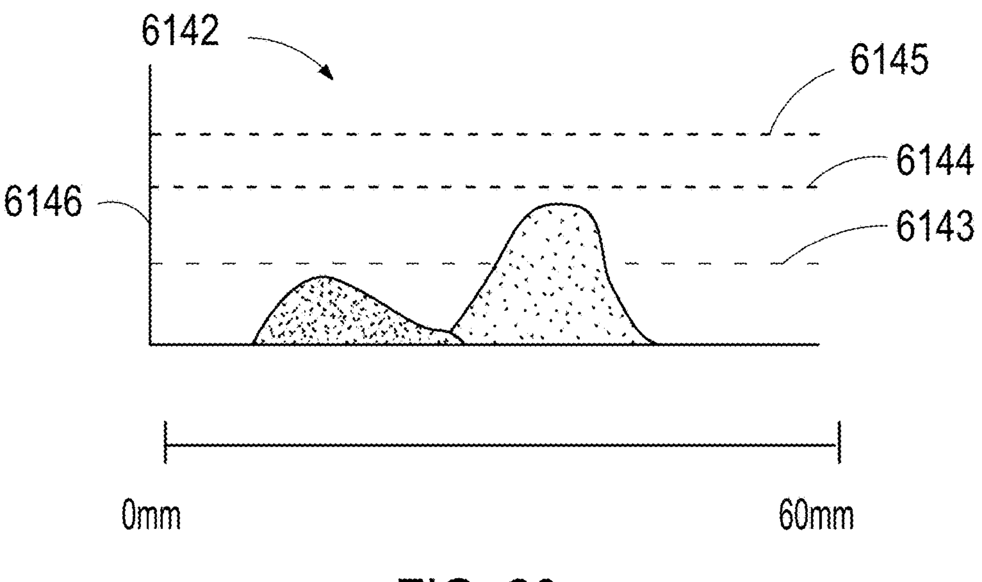
FIG. 29 illustrates a display arrangement, in accordance with methods of the present disclosure.

Referring to FIGS. 28 and 29, in some implementations, a display arrangement 6140 is presented by the control module 6001, for example, on a display 6005, for example, in accordance with methods of the present disclosure. The display 6005 shows a livestream of a surgical field during a surgical procedure that utilizes a surgical instrument 21 to staple and cut tissue T grasped by an end effector 6141 of the surgical instrument 21. In the illustrated example, the display arrangement 6140 overlays a performance parameter plot 6142 (FIG. 29) with history trace as a function of a firing member, cutting member, and/or knife position. The plot 6142 is overlaid adjacent to the end effector 6141, for example.

The plot 6142 presents risk severity associated with one or more parameters 6146 monitored during a firing sequence of the surgical instrument 21 such as, for example, an anvil gap, a tissue load, a firing speed, and/or a motor speed. Moreover, the plot 6142 further provides multiple thresholds, e.g. three thresholds 6143, 6144, 6145, each representing a severity level (e.g. low, medium, high) to provide a clinician with a visual indicator as to the severity of the risk associated with the measured parameter 6146.

Additionally, or alternatively, the display arrangement 6140 can be configured to utilize a color plot 6147 to present surgical data associated with a tissue parameter (e.g. tissue pressure, tissue compression, tissue flow, tissue thickness) of the tissue T. The tissue parameter values can be represented in different colors (e.g. green, yellow, red or light shading, intermediate shading, dark shading) that are in accordance with the values relations to one or more predetermined thresholds. In the illustrated example, green represents tissue portions with acceptable values, yellow represents tissue portions with low risk values, and red represents tissue portions with high risk values. The color plot 6147 provides a convenient and quick risk assessment tool that aids a clinician in determining whether to commence and/or continue a firing sequence, for example.

In various implementations, the tissue parameter values are measured by sensors dispersed in multiple locations across the width and along the length of the end effector 6141, for example. The tissue parameter values are then represented by coloring (e.g. green, yellow, red or light shading, intermediate shading, dark shading) areas on the color plot 6147 commensurate with the locations of the sensors on the end effector 6141, for example.

Figure 30:
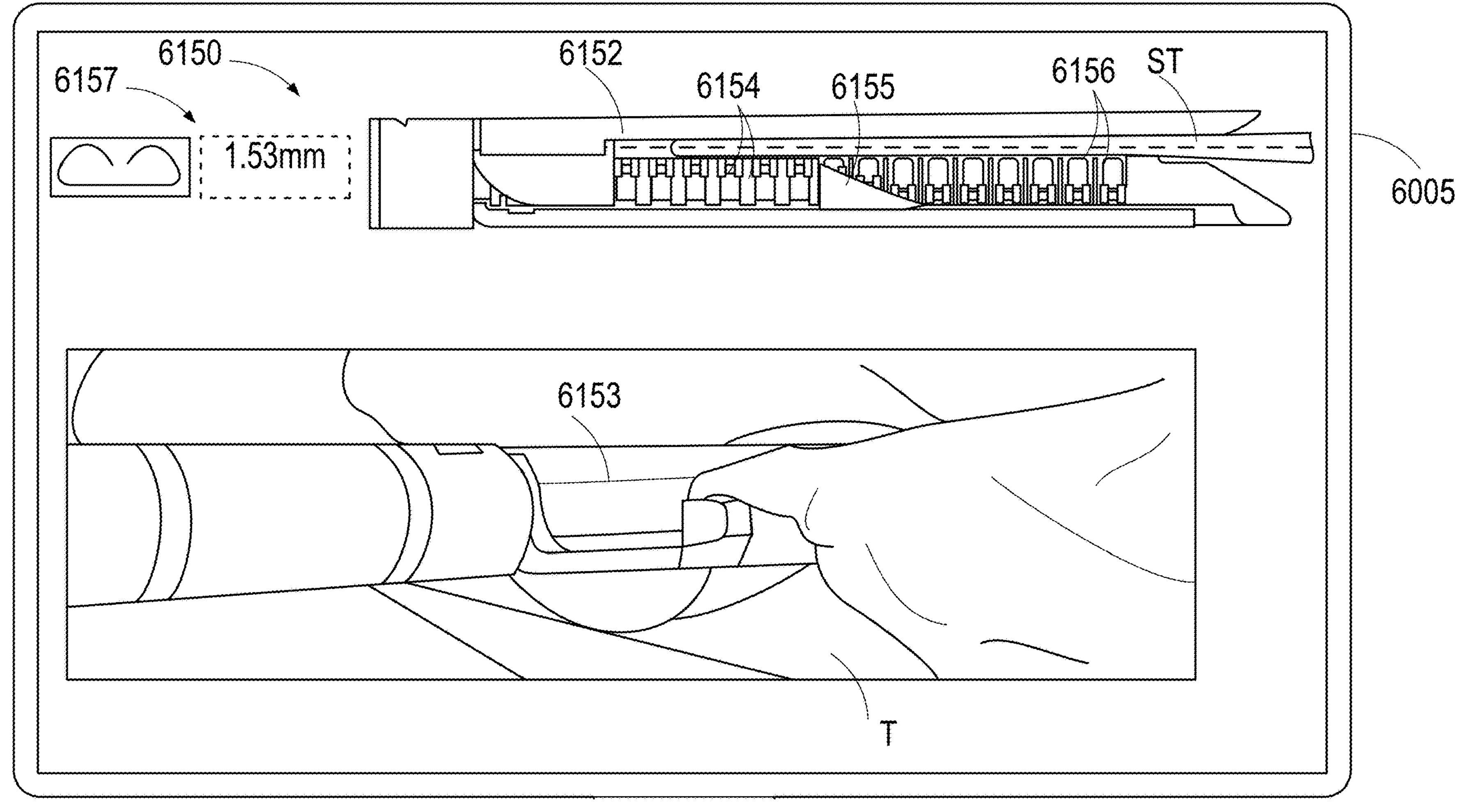
FIG. 30 illustrates a display arrangement, in accordance with methods of the present disclosure.

FIG. 30 illustrates a display arrangement 6150 that provides a visual representation of surgical data, in accordance with at least one aspect of the present disclosure. In some implementations, the display arrangement 6150 is presented by the control module 6001, for example, on the display 6005, for example, in accordance with methods of the present disclosure. In some implementations, the display arrangement 6150 is overlaid onto a livestream of a surgical field of a surgical procedure that utilizes a surgical instrument 21 to staple and cut tissue.

In some implementations, the display arrangement 6150 includes a simulated cross-sectional overlay 6152 an end effector 6153 of the surgical instrument 21 showing, and matching, positions and motions of one or more end effector components in real time, for example. Increased visualization can help the clinician better understand current statuses and risk-based feedback from the surgical instrument 21 (e.g. Clamping loads too high, force to fire too high, wait-time needed, etc).

In the illustrated example, the simulated overlay 6152 shows staples 6156, staple drivers 6154, and a firing member (e.g. sled 6155) configured to motivate the staple drivers 6154 to deploy staples 6156 into tissue. The position of the firing member in the simulated overlay 6152 mirrors the position of the firing member in the end effector 6153, and is indicative of the progress of the firing sequence, in real time. Moreover, in the illustrated example, the simulated overlay 6152 shows simulated tissue (ST), which can be presented in a manner reflective of tissue flow in areas where tissue flow is detected. While the illustrated example, only presents one row of staples 6156, in other examples, multiple rows can be shown.

In some implementations, the firing sequence is shown by the simulated overlay 6152 in a dynamic display mode. Moreover, the staple formation can, in some instances, be predicted based on one or more determined parameters such as, for example, tissue type, patient parameters, tissue flow, closure force, tissue creep stability, anvil gap, etc. For example, the control module 6001 may employ a predetermined equation, a database, and/or a table to predict the staple formation.

In the illustrated example, the display arrangement 6150 further includes a staple formation overlay 6157. The control module 6001 can be configured to predict staple formation, and update the staple formation overlay 6157 in real time, for example.

Figure 31:
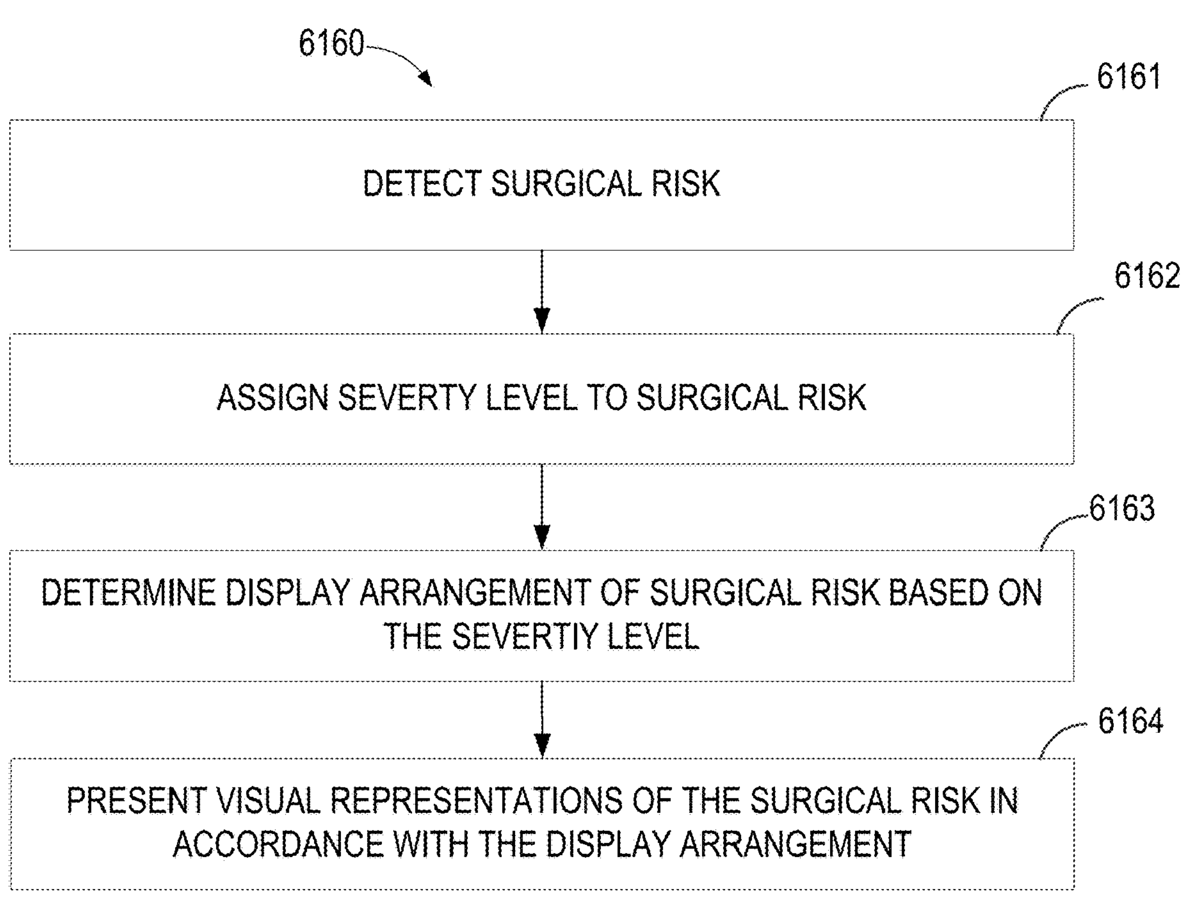
FIG. 31 is a flowchart showing operations of a method for risk-based manipulation of a display arrangement during a surgical procedure, in accordance with at least one aspect of the present disclosure.

FIG. 31 is a flowchart showing operations of an example method 6160 for risk-based manipulation of a display arrangement during a surgical procedure, in accordance with at least one aspect of the present disclosure. In some implementations, the method 6120 can be executed by the computer-implemented interactive surgical system 1, for example. In some implementations, the method 6160 is performed by a surgical system including a surgical instrument 21 configured to staple and cut tissue in a surgical field of a surgical procedure. The surgical system further includes a control module 6001, an imaging device 6004, and a display 6005 configured to show a livestream of the surgical field. The livestream is captured by the imaging device 6004, for example.

In some implementations, the method 6160 includes detecting 6161 a surgical risk, assigning 6162 a severity level to the surgical risk, and determining 6163 a display arrangement based on the severity level, wherein the display arrangement comprises overlaying an alert feature on the livestream. In some implementations, the method 6160 further includes presenting 6164 visual representations of the surgical risk, in accordance with the display arrangement.

In some implementations, the surgical risk is detected 6161 by the control module 6001. The surgical risk can be detected 6161 based one surgical data received from one or more sources such as, for example, components of the computer-implemented interactive surgical system 1 via one or more wireless and/or wired communication interfaces. In at least one example, the surgical data may include data received from one or more of the surgical instruments 21. In another example, the surgical data includes contextual information ascertained by the situational awareness module 6006.

In certain exemplifications, the surgical data comprise control data, biomarker measurements, and/or other operational indicators of operations and/or outcomes associated with a surgical instrument 21. In certain exemplifications, the surgical data can be any data indicative of a higher propensity of malformed staples and/or poorly sealed tissue. In certain instances, the surgical data can be associated with tissue flow, clamping force, firing force, among other tissue and/or instrument parameters, which can be monitored and displayed to the clinician in multiple ways in real time to allow for adjustments to the firing sequence or to alert the surgeon of a potentially malformed staple region.

In certain exemplifications, the processor 85 employs predetermined equations and/or formulas in determining the severity level of the surgical risk. Various relevant factors can be considered, and can be assigned different weights in calculating the severity level. Additionally, or alternatively, one or more databases or tables listing surgical data and corresponding severity levels can be utilized by the processor 85 in assigning 6162 the severity level. In various implementations, the assigned 6162 severity level comprises, for example, a low severity level, a medium severity level, or a high severity level.

Figure 32:
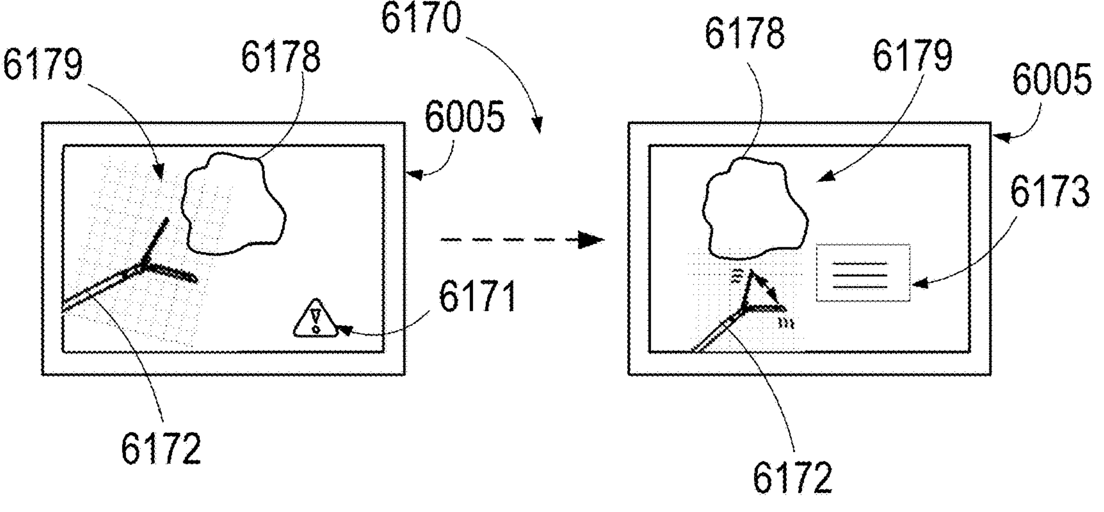
FIG. 32 illustrates a display arrangement, in accordance with at least one aspect of the present disclosure.

FIG. 32 illustrates an implementation of a display arrangement 6170, in accordance with at least one aspect of the present disclosure. In some implementations, the display arrangement 6170 is determined based on a severity level of the surgical risk detected 6161 in the method 6160, for example. In the illustrated example, the display arrangement 6170 includes overlaying, by the control module 6001, an alert feature 6171 in response to detecting 6161 the surgical risk. The alert feature 6171 is overlaid onto a livestream of a surgical field 6179 during the surgical procedure. In the illustrated example, the livestream of the surgical field 6179 shows an end effector 6172 of the surgical instrument 21 configured to manipulate a surgical structure 6178.

In the illustrated example, the alert feature 6171 is overlaid onto the livestream in a corner area, away from the end effector 6172 and/or away from any critical surgical structures, so as to not hinder a clinician's view of the surgical field. In other exemplifications, the alert feature 6171 can be moved to, or initially overlaid onto, a central area of the livestream, closer to the end effector 6172 and/or any critical surgical structures, for example, to signify a higher severity of the surgical risk.

Further to the above, the display arrangement 6170 includes a change in the alert feature 6171, in response to a user reaction. In the illustrated example, the change to the alert feature 6171 includes replacing the alert feature 6171 with information 6173 associated with the surgical risk. The information 6173 can include details about the surgical risk and/or recommended solutions.

In the illustrated example, the user reaction is a transition of the end effector 6172 between an open configuration and a closed configuration. In other implementations, the user reaction may include any other suitable gesture or motion by the end effector 6172. In yet other implementations, the user reaction may include a hand gesture or motion and/or eye gesture or motion, for example.

In other examples, the user reaction can be a compounded user reaction or a multi-factor reaction to ensure that incidental actions by the user will not be construed by the control module 6001 as user reactions for the purposes of manipulating the alert feature 6171. In some implantations, a user reaction recognizable by the control module 6001 may include two components such as, for example, an end effector gesture or motion followed by an eye movement of the user or a hand movement of the user.

Figure 33:
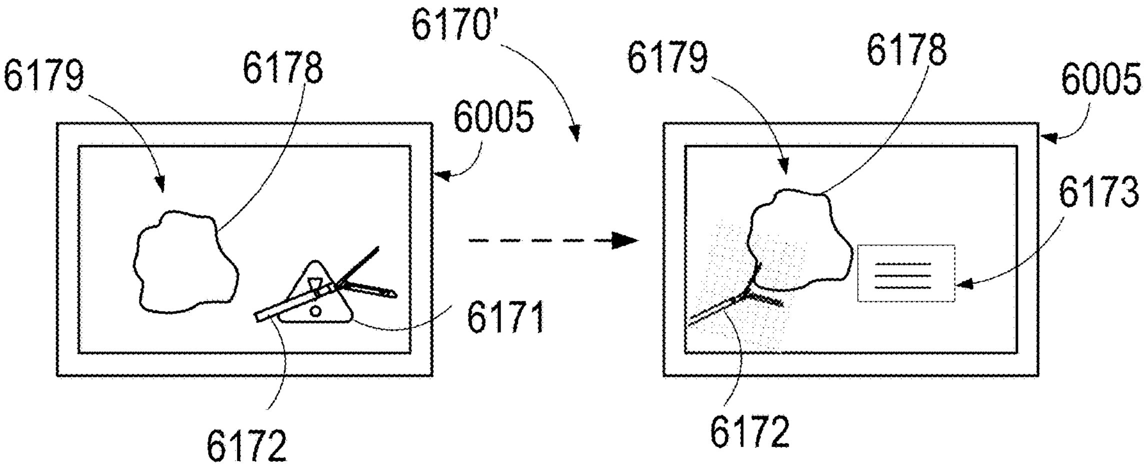
FIG. 33 illustrates a display arrangement, in accordance with at least one aspect of the present disclosure.

In some implementations, as illustrated in FIG. 33, a display arrangement 6170', which is similar in many respects to the display arrangement 6170, includes a different user reaction. In the illustrated example, the user reaction includes hovering the end effector 6172 over the alert feature 6171.

In some implementations, the user reaction is automatically detected through object recognition, object tracking, object labeling, and/or other suitable image processing techniques of image frames of the livestream, for example, or through various suitable wired and/or wireless communication schemes. Additionally, or alternatively, the user reaction can be automatically detected by receiving information, via suitable wired and/or wireless communication schemes, indicative of a user reaction. For example, a camera may monitor a body motion or a body gesture of the user such as, for example, a hand wave, an eye stare or a double blink. In another example, a clinician's glove can be tracked via one or more suitable sensors positioned on the glove. Sensor readings indicative of a predetermined hand motion, indicative of a predetermined user reaction, can be communicated to the control module 6001.

In some implementations, the display arrangement 6170 includes changing the alert feature 6171 based on a change in the severity of the surgical risk. The change can be implemented in a dynamic display mode, for example. In some exemplifications, the change to the alert feature 6171 includes a change in at least one of color, size, shape, display time, display location, display frequency, highlighting, or a combination thereof, in accordance with the severity level of the surgical risk. In some implementations, the alert feature 6171 is in the form of an alert icon, which changes color based on the severity level of the surgical risk, for example.

Figure 34:
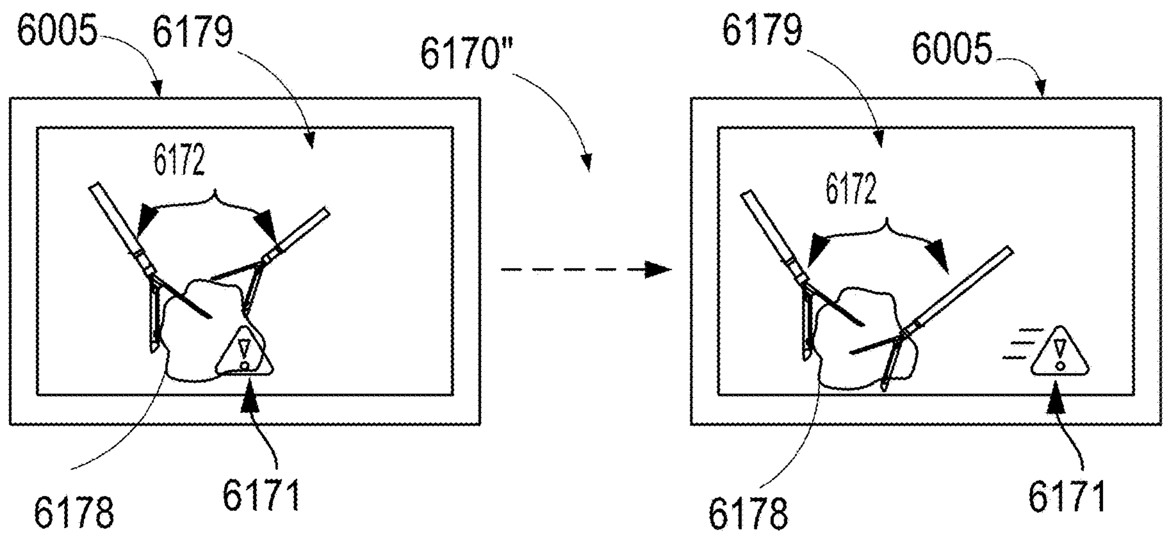
FIG. 34 illustrates a display arrangement, in accordance with at least one aspect of the present disclosure.

In some implementations, as illustrated in FIG. 34, a display arrangement 6170", which is similar in many respects to the display arrangement 6170, includes positioning the alert feature 6171 in a location that interferes with a clinician's view of a critical surgical structure 6178, to signify a high severity surgical risk, for example. Nonetheless, the display arrangement 6170" permits a user to move the alert feature 6171 away from the critical surgical structure 6178, by hovering the end effector 6172 over the alert feature 6171. In response to detecting that the end effector 6172 and the alert feature 6171 occupy the same location, the control module 6001 causes the alert feature to move to a different location on the livestream of the surgical field 6179, for example.

In other examples, a predetermined user reaction such as, for example, closing and opening the jaws of the end effector 6172 once, or twice, simulates grabbing the alert feature 6171. Moreover, the end effector 6172 can be moved to a corner of the display 6005, for example, causing the grabbed alert feature 6171 to move with it. A pause over the new location can signifies dropping the alert feature at the new location. Other suitable gestures and/or motions can be adopted to signify a user reaction to move the alert feature 6171 away from the critical surgical structure 6178. In some implementations, in a dynamic mode for example, the control module 6001 may automatically cause an alert feature 6171 to move away from an end effector 6172 and/or a critical surgical structure 6178, after an initial deployment that is determined to be less than, or equal to, an end effector 6172 and/or a critical surgical structure 6178, for example.

In various implementations, gestures and/or motions by the end effector 6172 can be automatically observed by utilizing one or more suitable object recognition, object tracking, and/or object labeling algorithms, and/or other image processing techniques of image frames of the livestream of the surgical field 6179, for example. In various instances, the end effector 6172 is visually recognized based on a characteristic reflectivity, color, and/or shaped. Additionally, or alternatively, gestures and/or motions by the end effector 6172 can be detected through sensor readings of sensors in the surgical instrument 21.

In some implementations, a change in the alert feature 6171, in response to the user reaction, includes a motion of the alert feature 6171 away from the end effector 6172 and/or a critical surgical structure 6178. In some exemplifications, the control module 6001, for example, is configured to track the positions of the end effector 6172 and/or the critical surgical structure 6178 with respect to the position of the alert feature 6171 on the display 6005. In addition, the control module 6001, for example, is configured to automatically change the position of the alert feature 6171 based on at least one of the positions of the end effector 6172 and the critical surgical structure 6178 to facilitate a clear view of the end effector 6172 and/or the critical surgical structure 6178.

In some implementations, the control module 6001, for example, is configured to correlate the alert feature 6171 to a source of the risk represented by the alert feature 6171. The correlation provides a clinician with an indication as to the nature of the risk without having to expand the alert feature 6171 to view details of the risk, for example. The correlation can be achieved through a common display characteristic such as, for example, a common color highlight and/or a common blink frequency. For example, where the risk is associated with a surgical instrument 21 comprising an end effector 6172 in the surgical field, the alert feature 6171 and the end effector 6172 can both be highlighted with a common color, for example. Additionally, or alternatively, the correlation can be achieved by causing the surgical instrument 21 to provide a sound and/or a haptic feedback that coincides with the presence of the alert feature 6171 on the display 6005, for example. Additionally, or alternatively, the correlation can be achieved by overlaying one or more color coded bubbles and/or arrows, separate from the alert feature 6171, which point to the end effector 6172, indicating that the risk represented by the alert feature 6171 is associated with the surgical instrument 21.

In some implementations, a display arrangement associated with a particular surgical instrument task, or a surgical step, can be changed in response to a detected completion of the surgical instrument task, or surgical step. For example, a surgical procedure such as a surgical sleeve procedure involves a predetermined number of firings of a surgical instrument 21 configured to staple and cut tissue. Each firing in the firing sequence deploys staples from a staple cartridge into the tissue. The staple cartridge is then replaced with a new staple cartridge for the following firing in the firing sequence. The control module 6001 can be configured to detect the number of firings by the surgical instrument 21, and to continue overlaying surgical data associated with the firing of the surgical instrument 21 until the predetermined number of firings is reached. In response to detecting the completion of the firings, the control module 6001 causes the overlay of the surgical data associated with the firing of the surgical instrument 21 to be collapsed or removed from the display 6005.

In some implementations, detecting the completion of the surgical instrument task, or surgical step, can be automatically achieved visually through object recognition, object tracking, object labeling, and/or other suitable image processing techniques of image frames of the livestream, for example, or through input from the surgical instrument 21 and/or a surgical hub 6, for example, via various suitable wired and/or wireless communication schemes.

In various instances, one or more functions of the aforementioned methods are executed by one or more components of the computer-implemented interactive surgical system 1 such as, for example, one or more components of the surgical visualization system 6000, for example. In certain instances, the components executing the one or more functions of the aforementioned methods communicate through wireless and/or wired communication interfaces. In various instances, a memory of the computer-implemented interactive surgical system 1, e.g. memory 6003, stores program instructions that, when executed by a processor (e.g. processor 85), cause the processor to effect one or more functions of the aforementioned methods. While the aforementioned functions are described in discrete methods, in some implementations, some functions of the aforementioned methods can be combined in any suitable form to yield different methods that yield different program instructions for execution by one or more components of the computer-implemented interactive surgical system 1, for example.

In various instances, to perform tracking, in accordance with one or more aspects of the present disclosure, an algorithm analyzes sequential video frames and outputs the movement of targets between the frames. Example algorithms include target representation and localization algorithms and filtering and data association algorithms. Target representation and localization algorithms include Kernel-based tracking and/or Contour tracking, for example. Filtering and data association algorithms include Kalman filters and Particle filters, for example.

Various additional aspects of the subject matter described herein are set out in the following numbered examples:

Example 1. A surgical visualization system comprising an imaging device, a display configured to show a livestream of a surgical field of a surgical procedure, wherein the livestream is captured by the imaging device, and a control module, configured to detect surgical data, assign display priority values to the surgical data, determine a display arrangement of the surgical data based on the display priority values, and present the surgical data on the display in accordance with the display arrangement.

Example 2. The surgical visualization system of Example 1, wherein the surgical data comprises first surgical data and second surgical data different than the first surgical data, wherein the first surgical data competes for presentation on the display with the second surgical data.

Example 3. The surgical visualization system of Example 2, wherein the display arrangement comprises an overlay arrangement of the first surgical data and the second surgical data onto the livestream based on the display priority values.

Example 4. The surgical visualization system of Examples 2 or 3, wherein the display priority values comprise a first display priority value assigned to the first surgical data and a second display priority value less than the first display priority value assigned to the second surgical data, and wherein the display arrangement comprises overlaying the first surgical data onto the livestream but not the second surgical data.

Example 5. The surgical visualization system of Examples 2 or 3, wherein the display priority values comprise a first display priority value assigned to the first surgical data and a second display priority value less than the first display priority value assigned to the second surgical data, and wherein the display arrangement comprises overlaying the first surgical data onto the livestream before the second surgical data.

Example 6. The surgical visualization system of any one of Examples 1-5, wherein the display arrangement comprises generating different visual representations of the surgical data based the display priority values.

Example 7. The surgical visualization system of any one of Examples 1-6, wherein the display arrangement comprises selecting, for one or more display elements of visual representations of the surgical data, a color, a size, a shape, a display time, a display location, a display frequency, a highlighting, or a combination thereof based on the display priority values.

Example 8. The surgical visualization system of any one of Examples 1-7, wherein at least one of the display priority values is based on a failure to receive a parameter associated with a setting of a surgical instrument utilized in the surgical procedure.

Example 9. The surgical visualization system of any one of Examples 1-8, wherein at least one of the display priority values is based on a detection of an assembly of components of a surgical instrument utilized in the surgical procedure.

Example 10. The surgical visualization system of any one of Examples 1-9, wherein at least one of the display priority values is based on a distance in the surgical field between a critical surgical structure and a surgical instrument.

Example 11. The surgical visualization system of any one of Examples 1-10, further comprising a situational awareness module configured to generate contextual information based on perioperative data, wherein the display arrangement of the surgical data on the display is further based on the contextual information.

Example 12. The surgical visualization system of any one of Examples 1-11, wherein the surgical visualization system comprises a communication interface, and wherein detecting the surgical data comprises receiving the surgical data via the communication interface.

Example 13. The surgical visualization system of any one of Examples 1-12, wherein the surgical visualization system comprises a processor, and wherein presenting the surgical data comprises automatically causing, by the processor, visual representations of the surgical data to be displayed onto the livestream of the surgical field.

Example 14. The surgical visualization system of any one of Examples 1-13, wherein the surgical visualization system comprises a processor and a memory, and wherein assigning display priority values to the surgical data comprises automatically retrieving, by the processor, the display priority values from the memory.

Example 15. The surgical visualization system of any one of Examples 1-14, wherein the surgical visualization system comprises a processor, and wherein the livestream of the surgical field is a first livestream of a first surgical field, and wherein determining the display arrangement comprises automatically selecting, by the processor, to switch from the first livestream to a second livestream of a second surgical field different than the first surgical field.

Example 16. A surgical visualization system comprising an imaging device, a display configured to show a livestream of a surgical field of a surgical procedure, wherein the livestream is captured by the imaging device, and a control module, configured to detect first surgical data, generate a first visual representation of the first surgical data for presenting the first surgical data on the display, detect second surgical data, generate a second visual representation of the second surgical data for presenting the second surgical data on the display, detect a display conflict between the first surgical data and the second surgical data, determine a resolution of the display conflict in favor of one of one of the first visual representation and the second visual representation based on at least one of the first surgical data and the second surgical data, and determine a display arrangement of the first visual representation and the second visual representation in accordance with the resolution.

Example 17. The surgical visualization system of Example 16, wherein the surgical visualization system comprises a communication interface, and wherein detecting the first surgical data comprises receiving the first surgical data via the communication interface.

Example 18. The surgical visualization system of Examples 16 or 17, wherein the surgical visualization system comprises a processor and a memory, and wherein generating the first visual representation comprises retrieving, by the processor, a template from the memory, and populating the template with at least one value based on the first surgical data.

Example 19. The surgical visualization system of any one of Examples 16-18, wherein the surgical visualization system comprises a processor and a memory, and wherein detecting the display conflict comprises retrieving display priority information for the first surgical data and the second surgical data from the memory.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical visualization system for use in a surgical procedure, the surgical visualization system comprising:

an imaging device;

a display configured to show a livestream of a surgical field of the surgical procedure, wherein the livestream is captured by the imaging device; and a control module, configured to:

detect surgical data;

assign display priority values to the surgical data;

generate a visual representation of the surgical data, wherein the visual representation comprises a display element having a characteristic;

determine a display arrangement of the visual representation of the surgical data over the surgical field based on the display priority values;

present the surgical data on the display based on the display arrangement;

determine an update to the surgical data;

generate an updated visual representation of the updated surgical data by changing the characteristic of the display element of the visual representation;

determine an updated display arrangement of the updated visual representation of the updated surgical data over the surgical field based on the display priority values; and present the updated surgical data on the display based on the updated display arrangement.

2. The surgical visualization system of claim 1, wherein the surgical data comprises first surgical data and second surgical data different than the first surgical data, wherein the first surgical data competes for presentation on the display with the second surgical data.

3. The surgical visualization system of claim 2, wherein the display arrangement comprises an overlay arrangement of the first surgical data and the second surgical data onto the livestream based on the display priority values.

4. The surgical visualization system of claim 2, wherein the display priority values comprise a first display priority value assigned to the first surgical data and a second display priority value less than the first display priority value assigned to the second surgical data, and wherein the display arrangement comprises overlaying the first surgical data onto the livestream but not the second surgical data.

5. The surgical visualization system of claim 2, wherein the display priority values comprise a first display priority value assigned to the first surgical data and a second display priority value less than the first display priority value assigned to the second surgical data, and wherein the display arrangement comprises overlaying the first surgical data onto the livestream before the second surgical data.

6. The surgical visualization system of claim 1, wherein the control module is further configured to select, for the characteristic of the display element of the visual representation of the surgical data, a color based on the display priority values.

7. The surgical visualization system of claim 1, wherein the control module is further configured to select, for the characteristic of the display element of the visual representation of the surgical data, a display time based on the display priority values.

8. The surgical visualization system of claim 1, wherein at least one of the display priority values is based on a failure to receive a parameter associated with a setting of a surgical instrument utilized in the surgical procedure.

9. The surgical visualization system of claim 1, wherein at least one of the display priority values is based on a detection of an assembly of components of a surgical instrument utilized in the surgical procedure.

10. The surgical visualization system of claim 1, wherein at least one of the display priority values is based on a distance in the surgical field between a critical surgical structure and a surgical instrument.

11. The surgical visualization system of claim 1, further comprising a situational awareness module configured to generate contextual information based on perioperative data, wherein the display arrangement of the surgical data on the display is further based on the contextual information.

12. The surgical visualization system of claim 1, wherein the visualization system comprises a communication interface, and wherein detecting the surgical data comprises receiving the surgical data via the communication interface.

13. The surgical visualization system of claim 1, wherein the visualization system comprises a processor, and wherein presenting the surgical data comprises automatically causing, by the processor, visual representations of the surgical data to be displayed onto the livestream of the surgical field.

14. The surgical visualization system of claim 1, wherein the visualization system comprises a processor and a memory, and wherein assigning display priority values to the surgical data comprises automatically retrieving, by the processor, the display priority values from the memory.

15. The surgical visualization system of claim 1, wherein the visualization system comprises a processor, and wherein the livestream of the surgical field is a first livestream of a first surgical field, and wherein determining the display arrangement comprises automatically selecting, by the processor, to switch from the first livestream to a second livestream of a second surgical field different than the first surgical field.

16. A surgical visualization system for use in a surgical procedure, the surgical visualization system comprising:

an imaging device;

a display configured to show a livestream of a surgical field of the surgical procedure, wherein the livestream is captured by the imaging device; and a control module, configured to:

detect first surgical data;

generate a first visual representation of the first surgical data for presenting the first surgical data on the display;

detect second surgical data;

generate a second visual representation of the second surgical data for presenting the second surgical data on the display;

detect a display conflict between the first surgical data and the second surgical data;

determine a resolution of the display conflict in favor of one of the first visual representation and the second visual representation based on a resolution order associated with an order of surgical tasks of the surgical procedure; and determine a display arrangement of the first visual representation and the second visual representation in accordance with the resolution over the surgical field.

17. The surgical visualization system of claim 16, wherein the surgical visualization system comprises a communication interface, and wherein detecting the first surgical data comprises receiving the first surgical data via the communication interface.

18. The surgical visualization system of claim 16, wherein the surgical visualization system comprises a processor and a memory, and wherein generating the first visual representation comprises retrieving, by the processor, a template from the memory, and populating the template with at least one value based on the first surgical data.

19. The surgical visualization system of claim 16, wherein the surgical visualization system comprises a processor and a memory, and wherein detecting the display conflict comprises retrieving display priority information for the first surgical data and the second surgical data from the memory.

20. The surgical visualization system of claim 1, wherein the control module is further configured to select, for one or more display elements of visual representations of the surgical data, a highlighting based on the display priority values.

* * * * *